United States Patent
Bakshi et al.

(10) Patent No.: US 6,350,760 B1
(45) Date of Patent: Feb. 26, 2002

(54) SUBSTITUTED PIPERIDINES AS MELANOCORTIN-4 RECEPTOR AGONISTS

(75) Inventors: Raman K. Bakshi, Edison, NJ (US); Khaled J. Barakat, Brooklyn, NY (US); Ravi P. Nargund, East Brunswick, NJ (US); Brenda L. Palucki, Belle Mead, NJ (US); Arthur A. Patchett, Westfield, NJ (US); Iyassu Sebhat, Hoboken, NJ (US); Zhixiong Ye, Princeton, NJ (US); Leonardus H. T. Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/585,111

(22) Filed: Jun. 1, 2000

Related U.S. Application Data

(60) Provisional application No. 60/137,477, filed on Jun. 4, 1999, and provisional application No. 60/169,209, filed on Dec. 2, 1999.

(51) Int. Cl.[7] ...................... A61K 31/44; A61K 31/395; C07D 205/00; C07D 223/16; C07D 217/12
(52) U.S. Cl. ............. 514/323; 514/210.16; 514/213.04; 514/307; 540/200; 540/476; 540/593; 540/594; 546/146; 546/200; 546/201
(58) Field of Search .................. 540/200, 476, 540/593, 594; 546/146, 200, 201; 514/210.16, 213.01, 307, 323 OR

(56) References Cited

U.S. PATENT DOCUMENTS

| | | |
|---|---|---|
| 5,492,920 A | 2/1996 | Chen |
| 5,536,716 A | 7/1996 | Chen |
| 5,559,128 A | 9/1996 | Chakravarty |
| 5,576,290 A | 11/1996 | Hadley |
| 5,578,593 A | 11/1996 | Chen |
| 5,674,839 A | 10/1997 | Hruby et al. |
| 5,714,576 A | 2/1998 | Hruby et al. |
| 5,721,251 A | 2/1998 | Chen |
| 5,731,408 A | 3/1998 | Hadley |
| 5,767,118 A | 6/1998 | Nargund |
| 6,051,555 A | 4/2000 | Hadley |

FOREIGN PATENT DOCUMENTS

| | | |
|---|---|---|
| WO | WO 97/34604 | 9/1997 |
| WO | WO 98/10653 | 3/1998 |
| WO | WO 98/25897 | 6/1998 |
| WO | WO 99/55679 | 11/1999 |
| WO | WO 99/64002 | 12/1999 |
| WO | WO 00/58361 | 10/2000 |
| WO | WO 01/00224 A1 | 1/2001 |
| WO | WO 01/05401 A1 | 1/2001 |
| WO | WO 01/10842 A2 | 2/2001 |

OTHER PUBLICATIONS

Wessells et al, "Effect of an Alpha–Melanocyte Stimulating Hormone Analog on Penile Erection and Sexual Desire in Men with Organic Erectile Dysfunction", Urology, vol. 56 (#4), pp. 641–646 (2000).

Wessells, H. et al., "Synthetic Melanotropic Peptide Initiates Erections in Men With Psychogenic Erectile Dysfunction: Double–Blind, Placebo Controlled Crossover Study", The Journal of Urology, vol. 160, pp. 389–393, (Aug. 1998).

Dorr, R., et al., "Evaluation of Melanotan–II, A Superpotent Cyclic Melanotropic Peptide in a Pilot Phase–I Clinical Study", Life Sciences, vol. 58, No. 20 pp. 1777–1784 (1996).

*Primary Examiner*—D. Margaret Seaman
(74) *Attorney, Agent, or Firm*—Philippe L. Durette; Melvin Winokur

(57) ABSTRACT

Certain novel substituted piperidine compounds are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction. Also provided are methods of treating sexual dysfunction with a compound that is a selective agonist of MC-4R over any other human melanocortin receptor.

25 Claims, No Drawings

SUBSTITUTED PIPERIDINES AS MELANOCORTIN-4 RECEPTOR AGONISTS

CROSS-REFERENCE TO RELATED APPLICATIONS

The present invention is related to provisional applications Ser. No. 60/137,477, filed Jun. 4, 1999, and 60/169,209, filed Dec. 2, 1999; the contents of both of which are hereby incorporated by reference.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified.

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (Huszar et al., *Cell*, 88, 131–141, 1997) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period.

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity. MC-5R is expressed in many tissues, including white fat, placenta, and exocrine glands. A low level of expression is also observed in the brain. MC-5R knockout mice reveal reduced sebaceous gland lipid production (Chen et al., *Cell*, 1997, 91, 789–798).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387–390 (1999)]. Only more recently have more viable treatment modalities become available, in particular orally active agents, such as sildenafil citrate, marketed by Pfizer under the brand name of Viagra®. Sildenafil is a selective inhibitor of type V phosphodiesterase (PDE-V), a cyclic-GMP-specific phosphodiesterase isozyme [see R.B. Moreland et al., "Sildenafil: A Novel Inhibitor of Phosphodiesterase Type 5 in Human Corpus Cavernosum Smooth Muscle Cells," *Life Sci.*, 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives*, 9: 572–575 (1996); "Oral Pharmacotherapy in Erectile Dysfunction," *Current Opinion in Urology*, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects-of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389–393 (1998); *Fifteenth American Peptide Symposium*, June 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH2, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

Because of the unresolved deficiencies of the various pharmacological agents discussed above, there is a continuing need in the medical arts for improved methods and compositions to treat individuals suffering from psychogenic and/or organic erectile dysfunction. Such methods should have wider applicability, enhanced convenience and ease of compliance, short onset of action, reasonably long duration of action, and minimal side effects with few contraindications, as compared to agents now available.

It is therefore an object of the present invention to provide compounds which are useful as melanocortin receptor agonists.

It is another object of the present invention to provide compounds which are useful as selective agonists of the melanocortin-4 (MC-4R) receptor.

It is another object of the present invention to provide pharmaceutical compositions comprising melanocortin receptor agonists.

It is another object of the present invention to provide compounds and pharmaceutical compositions useful for the treatment or prevention of obesity, diabetes mellitus, and male and/or female sexual dysfunction.

It is another object of the present invention to provide compounds and pharmaceutical compositions for the treatment or prevention of erectile dysfunction.

It is another object of the present invention to provide methods for the treatment or prevention of disorders, diseases, or conditions responsive to the activation of the melanocortin receptor in a mammal in need thereof by administering the compounds and pharmaceutical compositions of the present invention.

It is another object of the present invention to provide methods for the treatment or prevention of disorders, diseases, or conditions responsive to the selective activation of the melanocortin-4 receptor in a mammal in need thereof by administering the compounds and pharmaceutical compositions of the present invention.

It is another object of the present invention to provide methods for the treatment or prevention of obesity, diabetes mellitus, and male and/or female sexual dysfunction.

It is another object of the present invention to provide methods for the treatment of male and/or female sexual dysfunction by administering therapeutically effective amounts of a compound which is a selective melanocortin4 receptor agonist.

It is another object of the present invention to provide methods for the treatment of erectile dysfunction by administering therapeutically effective amounts of a compound which is a selective melanocortin-4 receptor agonist.

These and other objects will become readily apparent from the detailed description that follows

SUMMARY OF THE INVENTION

The present invention discloses novel 4-substituted piperidines of structural formula I:

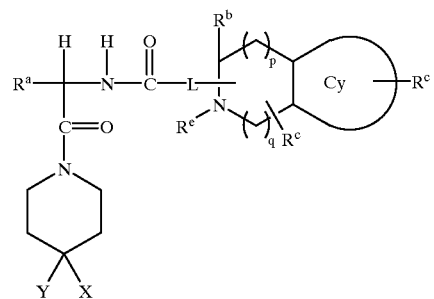

The compounds of Formula I are effective as human melanocortin receptor agonists and are particularly effective as selective human melanocortin-4 receptor (MC-4R) agonists. They are therefore useful for the treatment and/or prevention of disorders responsive to the activation of human MC-4R, such as obesity, diabetes as well as male and/or female sexual dysfunction, in particular, male erectile dysfunction.

The present invention also discloses methods for the treatment of male and/or female sexual dysfunction which comprises administering to the subject in need thereof a therapeutically effective amount of a compound which is a human MC-4R agonist wherein the compound binds to the human MC-4R with a binding affinity at least 10-fold higher than the compound binds to each of the human MC-1R, MC-2R, MC-3R, and MC-5R.

The present invention also discloses methods for the treatment of male and/or female sexual dysfunction which comprises administering to the subject in need thereof a therapeutically effective amount of a compound which is a human MC-4R agonist wherein the functional activity of the compound at the human MC-4R is characterized by an $EC_{50}$ at least 10-fold lower than the functional activity at each of the human MC-1R, MC-2R, MC-3R, and MC-5R.

The present invention also provides a method for the oral treatment of sexual dysfunction, in particular erectile dysfunction, in a male or female subject which comprises the oral administration to the subject in need thereof a therapeutically effective amount of a compound which is an agonist, in particular a selective agonist, of the human MC-4R.

The present invention also relates to pharmnaceutical compositions comprising the compounds of Formula I and a pharmaceutically acceptable canrier.

DETAILED DESCRIPTION OF THE INVENTION

The present invention provides compounds having the formula I:

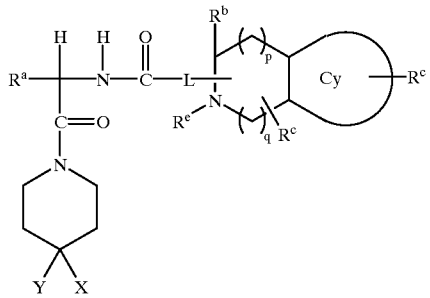

I or a pharmaceutically acceptable salt thereof; wherein
Cy is (1) aryl,
(2) 5- or 6-membered heteroaryl,
(3) 5- or 6-membered heterocyclyl, or
(4) 5-to 7-membered carbocyclyl;
L is $(CR^bR^b)_m$;
m is 0, 1 or 2;
n is 0, 1, 2, or 3;
p is 0, 1 or 2;
q is 0, 1 or 2;
$R^a$ is (1) hydrogen,
(2) $C_{1-8}$ alkyl,
(3) $(CHR^b)_n$—$C_{3-7}$cycloalkyl,
(4) $(CHR^b)_n$aryl,
(5) $(CHR^b)_n$heteroaryl, or
(6) $(CHR^b)_n$—$O(CHR^b)$aryl;
in which alkyl is optionally substituted with from 1 to 3 groups independently selected from Rg; aryl, heteroaryl and cycloalkyl are optionally substituted with 1 to 3 groups independently selected from $R^f$;
$R^b$ is (1) hydrogen,
(2) $C_{1-8}$alkyl,
(3) $(CH_2)_nC_{3-7}$cycloalkyl, or
(4) $(CH_2)_n$-aryl;
$R^c$ is (1) hydrogen or
(2) a group selected from $R^f$;
$R^d$ is (1) hydrogen,
(2) $C_{1-8}$alkyl,
(3) $(CH_2)_n$-aryl,
(4) $(CH_2)_nC_{3-7}$cycloalkyl or
(5) $(CH_2)_n$-heteroaryl;
wherein alkyl and cycloalkyl are optionally substituted with 1 to 3 groups selected from Rg; and cycloalkyl, aryl and heteroaryl are optionally substituted with 1 to 3 groups selected from $R^f$; or two $R^d$ groups together with the atoms to which they are attached form a 5- or 6- membered ring optionally containing an additional heteroatom selected from O, S, and $NR^b$;
$R^e$ is (1) a group selected from $R^d$,
(2) $COR^d$,
(3) $SO_2R^d$, or
(4) $COC(R^b)(R^b)N(R^d)(R^d)$;
$R^f$ is (1) a group selected from Rg or
(2) $C_{1-8}$ alkyl;
Rg is (1) $(CH_2)_n$-aryl,
(2) $(CH_2)_nC_{3-7}$cycloalkyl,
(3) $(CH_2)_n$-heteroaryl,
(4) halo,
(5) $OR^b$,
(6) $NHSO_2R^b$,
(7) $N(R^b)_2$,
(8) C≡N,
(9) $CO_2R^b$,
(10) $C(R^b)(R^b)N(R^b)_2$,
(11) $NO_2$,
(12) $SO_2N(R^b)_2$,
(13) $S(O)_mR^b$,
(14) $CF_3$, or
(15) $OCF_3$;
X is (1) hydrogen,
(2) $C_{1-8}$ alkyl,
(3) $(CH_2)_nC_{3-8}$cycloalkyl,
(4) $(CH_2)_n$aryl,
(5) $(CH_2)_n$heteroaryl,
(6) $(CH_2)_n$heterocyclyl,
(7) C≡N,
(8) $(CH_2)_nCON(R^dR^d)$,
(9) $(CH_2)_nC(O)OR^d$,
(10) $(CH_2)_nNR^dC(O)R^d$,
(11) $(CH_2)_nNR^dC(O)OR^d$,
(12) $(CH_2)_nNR^dC(O)N(R^d)_2$,
(13) $(CH_2)_nNR^dSO_2R^d$,
(14) $(CH_2)_nS(O)mR^d$,
(15) $(CH_2)_nSO_2N(R^d)(R^d)$,
(16) $(CH_2)_nOR^d$,
(17) $(CH_2)_nOC(O)R^d$,
(18) $(CH_2)_nOC(O)OR^d$,
(19) $(CH_2)_nOC(O)N(R^d)_2$,
(20) $(CH_2)_nN(R^d)(R^d)$,
(21) $(CH_2)_nNR^dSO_2N(R^d)(R^d)$, or
(22) $(CH_2)_nC(O)R^d$;
wherein the cycloalkyl, aryl and heteroaryl groups are optionally substituted with 1 to 3 groups selected from $R^f$; the heterocyclyl group is optionally substituted with 1 to 3 groups selected from $R^f$ and oxo; and the $(CH_2)_n$ and alkyl groups are optionally substituted with 1 to 3 groups selected from Rg;
Y is (1) hydrogen,
(2) $C_{1-8}$alkyl,
(3) $(CH_2)_nC_{3-8}$cycloalkyl,
(4) $(CH_2)_n$aryl,
(5) $(CH_2)_n$heterocyclyl, or
(6) $(CH_2)_n$heteroaryl;
wherein the cycloalkyl, aryl and heteroaryl groups are optionally substituted with 1 to 3 groups selected from $R^f$; the heterocyclyl group is optionally substituted with 1 to 3 groups selected from Rf and oxo; and the alkyl group is optionally substituted with 1 to 3 groups selected from Rg;

with the proviso that X and Y are not both simultaneously hydrogen.

In one subset of compounds of formula I, Cy is selected from benzene, pyridine, pyrazine, piperidine, imidazole and cyclohexane. Preferably, Cy is benzene, pyrazine, or cyclohexane; more preferably Cy is benzene. As substituent for Cy, Rc is preferably H, OH, $C_{1-4}$ alkoxy, halogen, or $S(O)_mR^b$; more preferably $R^c$ is H.

In another subset of compounds of formula I, L is $(CH_2)_m$ wherein m is 0, 1 or 2; preferably m is 0 or 1.

In another subset of compounds of formula I, $R^a$ is $CH(R^b)$-aryl, $CH(R^b)$—$OCH_2$aryl, or $CH(R^b)$-heteroaryl wherein the aryl or heteroaryl group is optionally substituted with one or two Rg groups. Preferably $R^a$ is $CH(R^b)$-aryl optionally substituted with one or two groups selected from Rg; more preferably $R^a$ is benzyl optionally substituted with one or two groups selected from halogen, $C_{1-4}$ alkyl, $C_{1-4}$ alkoxy, $CF_3$, and $OCF_3$. Even more preferred $R^a$ is 4-halobenzyl or 4-methoxybenzyl, with 4-chlorobenzyl and 4-fluorobenzyl being the most preferred.

In another subset of compounds of formula I, $R^b$ attached to the bicyclic ring is H or $C_{1-4}$ alkyl; preferably $R^b$ is H or $CH_3$.

In another subset of compounds of formula I, X is $C_{1-8}$alkyl, $(CH_2)_n$-$C_{3-7}$cycloalkyl, $(CH_2)_n$-aryl, $(CH_2)_n$-heteroaryl, $(CH_2)_n$-heterocyclyl, $(CH_2)_nC(O)N(R^d)(R^d)$, $(CH_2)_nC(O)OR^d$, $(CH_2)nOR^d$, $(CH_2)_nNHC(O)R^d$, $(CH)_nN(R^d)SO_2R^d$, or $(CH_2)_nSR^d$, wherein the cycloalkyl, aryl and heteroaryl groups are optionally substituted with 1 to 3 groups selected from $R^f$; heterocyclyl is optionally substituted with 1 to 3 groups selected from $R^f$ and oxo; and the $(CH_2)_n$ and alkyl groups are optionally substituted with 1 to 3 groups selected from $R^b$, halo, $S(O)mR^b$, $N(Rb)_2$, and $OR^b$.

In a preferred subset, X is $CH_2$-heteroaryl, $CH_2$-heterocyclyl, $NHC(O)R^d$, $C(O)OR^d$, $CH_2N(R^d)SO_2R^d$, or $C(O)N(R^d)(R^d)$, wherein heteroaryl is optionally substituted with 1 to 3 groups selected from $R^f$; heterocyclyl is optionally substituted with 1 to 3 groups selected from $R^f$ and oxo; and wherein $R^d$ is selected from H and $C_{1-6}$ alkyl optionally substituted with $OR^b$, $SR^b$, or $N(R^b)_2$, or 2 $R^d$ groups together with the nitrogen to which they are attached form a 5- or 6-membered ring optionally having an additional heteroatom selected from O, S and $NR^b$. More preferably, heteroaryl is selected from pyridyl, pyrazinyl, pyrimidinyl, triazolyl (all isomers), tetrazolyl, thiadiazolyl, oxadiazolyl, pyrazolyl and imidazolyl.

Representative X groups include, but are not limited to, carboxy, methyloxycarbonyl, ethyloxycarbonyl, propyloxycarbonyl, isopropyloxycarbonyl, n-butyloxycarbonyl, 2-(methylthio)ethyloxycarbonyl, 2-(dimethylamino)ethyloxycarbonyl, 2-methoxyethyloxycarbonyl, aminocarbonyl, methylaminocarbonyl, ethylaminocarbonyl, propylaminocarbonyl, isopropylaminocarbonyl, n-butylaminocarbonyl, t-butylaminocarbonyl, (2-methylthio)ethylaminocarbonyl, (2-hydroxy) ethylaminocarbonyl, 1-morpholinylcarbonyl, 1-thiomorpholinylcarbonyl, piperazinecarbonyl, 4-methanesulfonamido-1-piperazinecarbonyl, 4-methyl-1-piperazinecarbonyl, methylureido, 2-hydroxyethylureido, 2-(methylthio)ethylureido, isopropanoylamino, cyclohexanoylamino, propanoylamino, isobutanoylamino, isopropylsulfonamido, methylsulfonamido, phenylsulfonamido, isopropionyloxy, acetoxy, benzoyloxy, methoxycarbonylamino, n-butyl, ethoxymethyl, cyclopropylmethyl, 3-methylbutyl, benzyl, (ethoxycarbonyl)benzyl, (tetrazolyl)benzyl, 1-3 halo-substituted benzyl, pyridylmethyl, pyrimidylmethyl, indolylmethyl, 3-methyl-2-pyridylmethyl, phenylthio, pyridylthio, pyrimidylthio, thiazolylthio, methylthiazolylthio, thiazolylmethyl, methylthiazolylmethyl, 1,3,4-thiadiazolylmethyl, 5-methyl-1,3,4-thiadiazolylmethyl, 1,2,5-thiadiazolylmethyl, 3-methyl- 1,3,4-thiadiazolylmethyl, oxazolylmethyl, methyloxazolylmethyl, imidazolylmethyl, 2-methylimidazolylmethyl, 1,2,4-triazol-1-ylmethyl, 1,2,4-oxadiazolylmethyl, 3-methyl-1,2,4-oxadiazolylmethyl, tetrazolymethyl, N-methyltetrazolylmethyl, 1,2,3-triazolylmethyl, dihydro-1,2,4-triazol-3-one, and 2-methyl-dihydro-1,2,4-triazol-3-one.

In another subset of compounds of formula I, Y is $(CH_2)_nC_{3-7}$ cycloalkyl, $(CH_2)_n$-aryl, $(CH_2)_n$-heterocyclyl, or $(CH_2)_n$-heteroaryl wherein cycloalkyl, aryl and heteroaryl are optionally substituted with 1 to 3 groups selected from $R^f$, and heterocyclyl is optionally substituted with 1 to 3 groups selected from $R^f$ and oxo. Preferably, Y is cyclohexyl, cyclopentyl, cycloheptyl, cyclobutylmethyl, hexyl, tetrahydropyranyl, phenyl, naphthyl, pyridyl, thienyl or furanyl. More preferably, Y is cyclohexyl, tetrahydropyranyl, or phenyl, with the most preferred Y being cyclohexyl. Examples of Y include, but are not limited to, cycloheptyl, cyclopentyl, cyclohexyl, phenyl, tetrahydropyranyl, thienyl, furanyl, pyridyl, benzyl, pyridyl-methyl.

In compounds of formula I, preferably one of p and q is 1 and the other is 0 or 1; more preferably p and q are both 1.

In a preferred embodiment there are provided compounds of formula Ia:

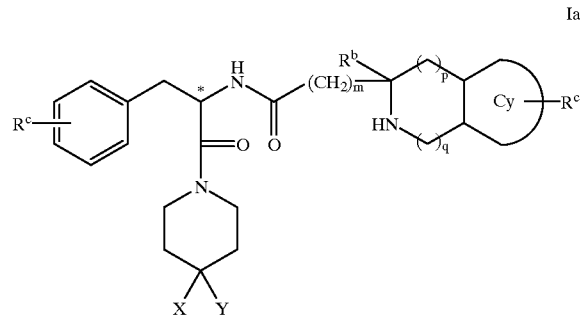

Ia or a pharmaceutically acceptable salt thereof, wherein
Cy is (1) phenyl,
  (2) pyridyl,
  (3) piperidinyl,
  (4) imidazolyl,
  (5) cyclohexyl, or
  (6) pyrazinyl;
m is 0 or 1;
n is 0 or 1;
p is 0 or 1;
q is 1 or 2;
$R^b$ is (1) hydrogen,
  (2) $C_{1-8}$alkyl, or
  (3) $C_{3-6}$cycloalkyl;
$R^c$ is (1) hydrogen, (2) halo,
(3) $C_{1-8}$alkyl, or
(4) $C_{3-6}$cycloalkyl,
(5) $OR^b$,
(6) $CF_3$,
(7) $OCF_3$,
(6) $S(O)_mR^b$, or
(7) $N(R^b)(R^b)$;

$R^d$ is (1) hydrogen,
(2) $C_{1-5}$alkyl, optionally substituted with $OR^b$, $NR^bR^b$, or $SR^b$,
(3) aryl,
(4) heteroaryl,
(5) $C_{5-6}$cycloalkyl, or
two $R^d$ together with the atoms to which they are attached form a 5- or 6-membered ring optionally containing an additional heteroatom selected from O, S and $NR^b$;

X is (1) hydrogen,
(2) $C(O)OR^d$,
(3) $C(O)N(R^d)(R^d)$,
(4) $NHC(O)R^d$,
(5) $NHC(O)NHR^d$,
(6) $NHC(O)OR^d$,
(7) $NHSO_2R^d$,
(8) $OC(O)R^d$,
(9) $C_{1-6}$alkyl,
(10) $CH_2$—$C_{3-7}$cycloalkyl,
(11) $(CH_2)_n$-aryl, optionally substituted with 1 to 3 groups selected from halogen, $C(O)OR^b$, and tetrazole,
(12) $(CH_2)_n$-heteroaryl, optionally substituted with $C_{1-3}$alkyl, $N(R^b)(R^b)$, or $OR^b$,
(13) $(CH_2)_n$-heterocyclyl optionally substituted with 1 to 3 groups selected from $C_{1-3}$ alkyl and oxo,
(14) $CH_2$—$OR^d$,
(15) $(CH_2)_nS(O)_mR^d$,
(16) $(CH_2)_nN(Rd)SO_2R^d$,
(17) $(CH_2)_nC(O)R^d$, or
(18) S-heteroaryl;

Y is (1) hydrogen,
(2) $C_{1-8}$alkyl,
(3) $C_{3-7}$cycloalkyl,
(4) $(CH_2)_n$aryl,
(5) $(CH_2)_n$heteroaryl, or
(6) $(CH_2)_n$heterocyclyl;
wherein the cycloalkyl, aryl, heteroaryl, or heterocyclyl group is optionally substituted with one or two halo groups;

with the proviso that X and Y are not both simultaneously hydrogen;

In a more preferred embodiment of compounds of formula Ia, the carbon atom marked with * has the R configuration.

In another more preferred embodiment of compounds of formula Ia, X is selected from the group consisting of:

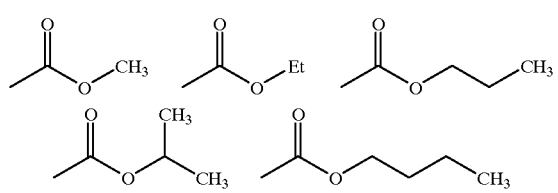

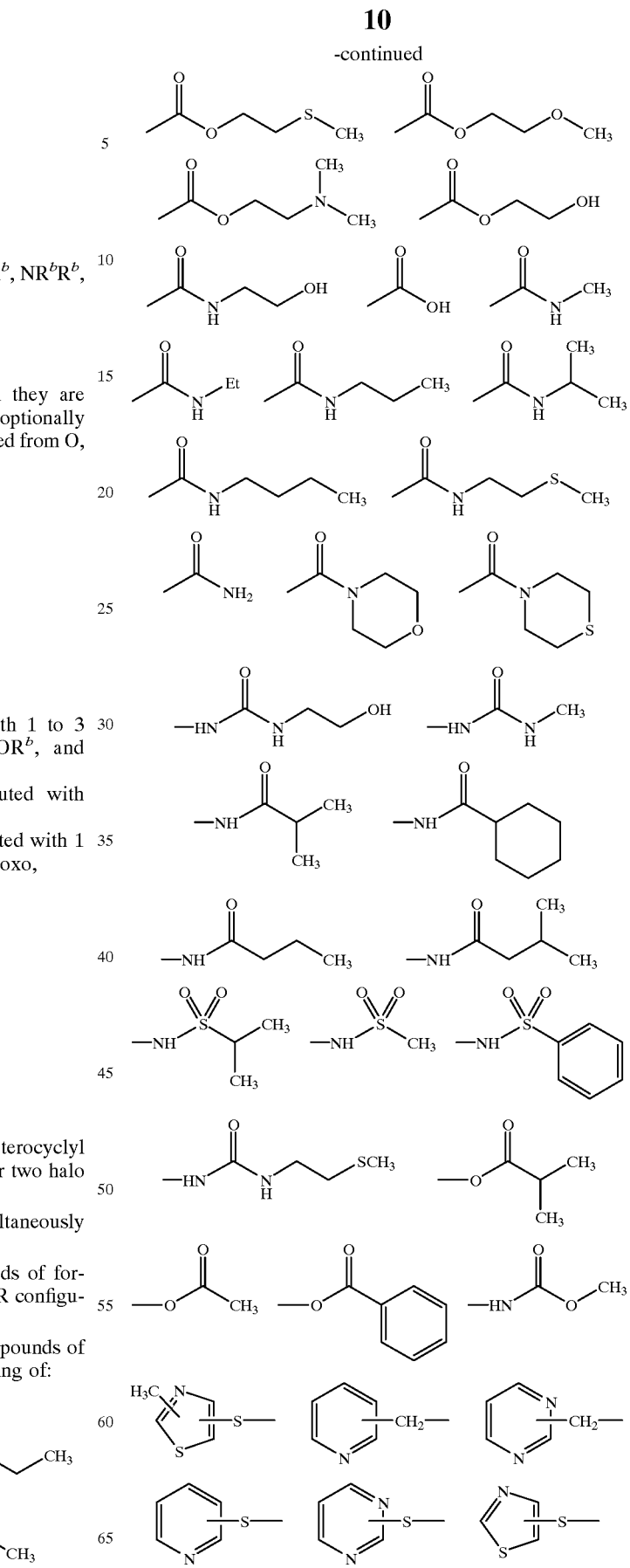

-continued
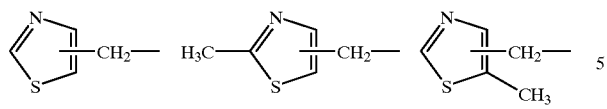
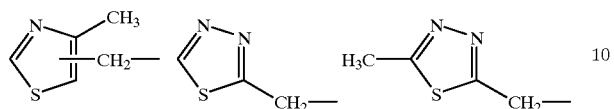
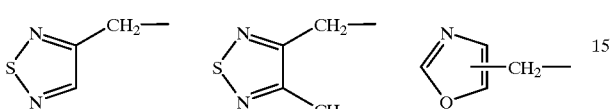
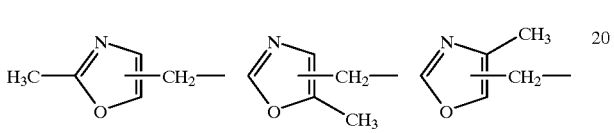
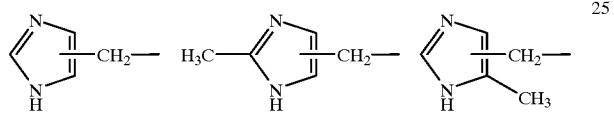
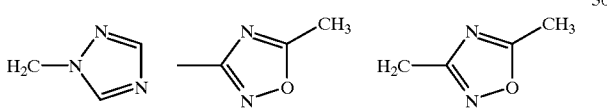
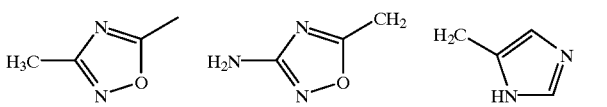
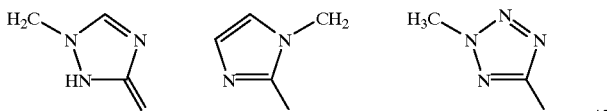
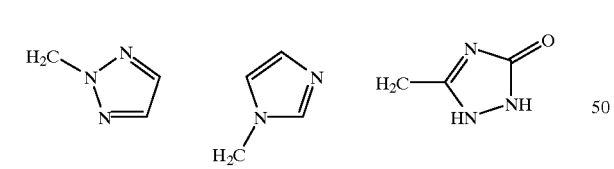
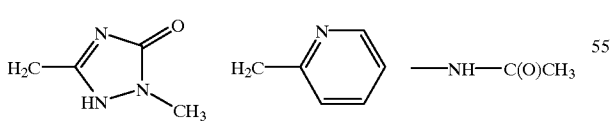
—C(O)N(CH$_3$)$_2$  —C(O)NH-t-Bu  —CH$_2$S(O)CH(CH$_3$)$_2$
—C(O)NHCH$_2$CH$_2$N(CH$_3$)$_2$   C(O)CH(CH$_3$)$_2$
—CH$_2$S(O)$_2$CH(CH$_3$)$_2$   —CH$_2$N(iPr)SO$_2$CH$_3$
-continued
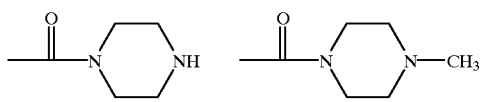
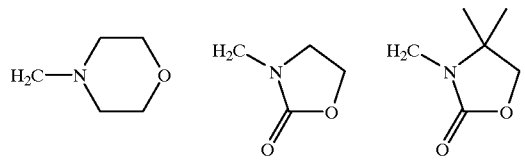
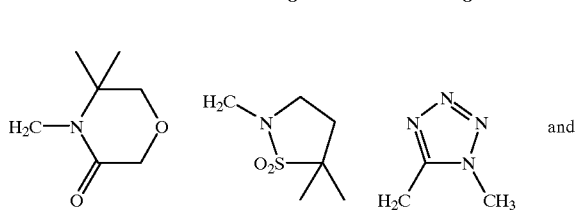
Representative compounds of formula I are as follows:
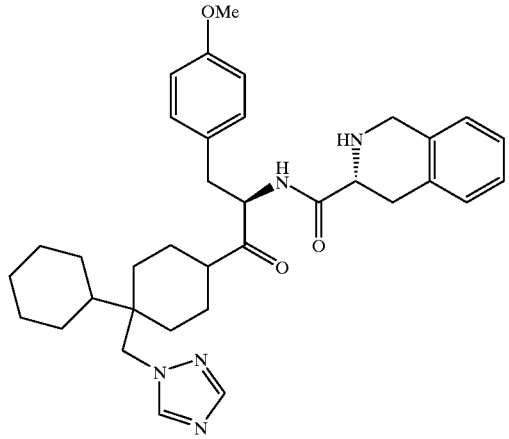
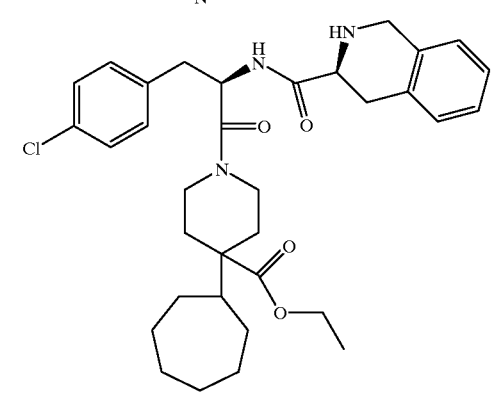

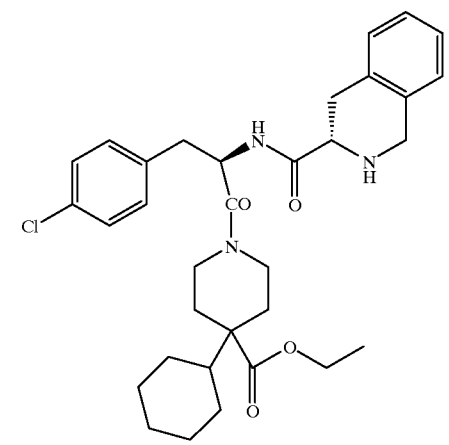
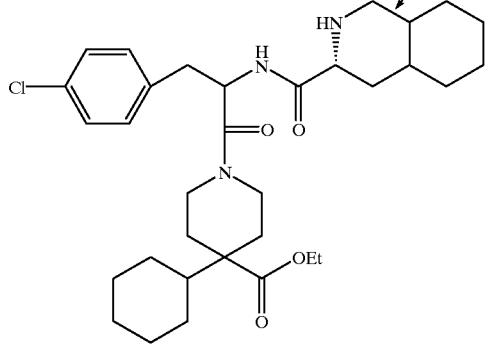
one diastereomer (d₁ or d₂)-cis ring junction
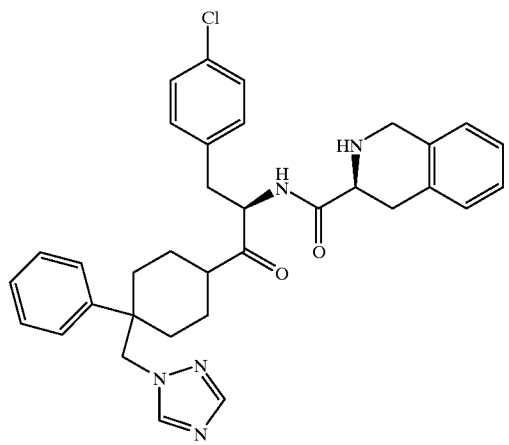
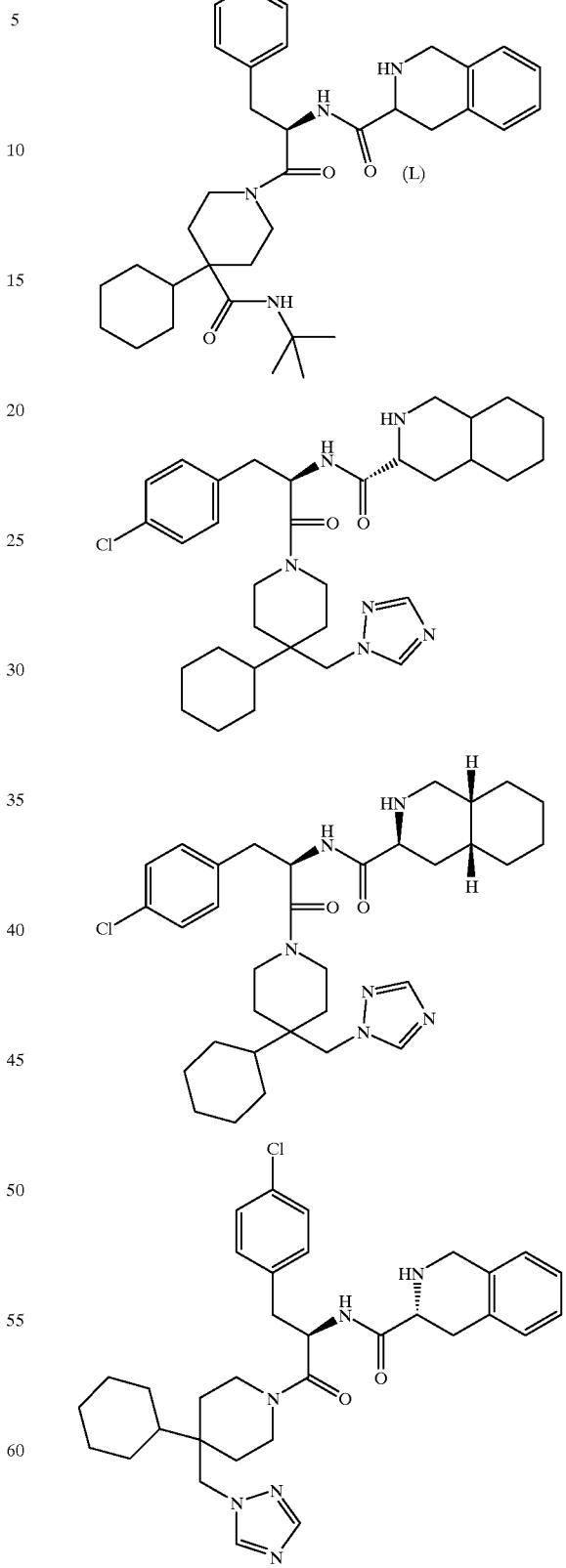

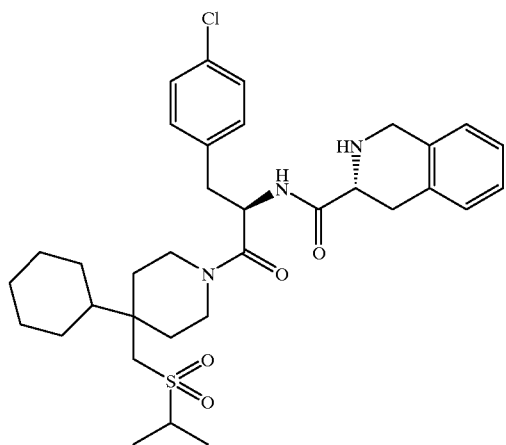
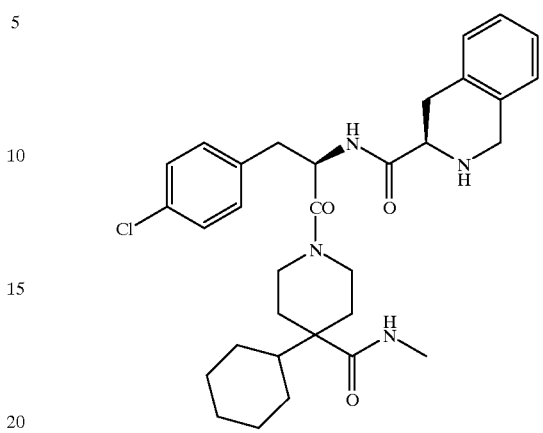
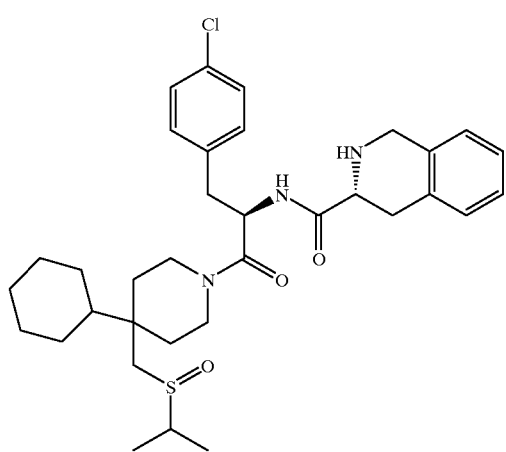
d₁ + d₂ diastereomeric at sulfur
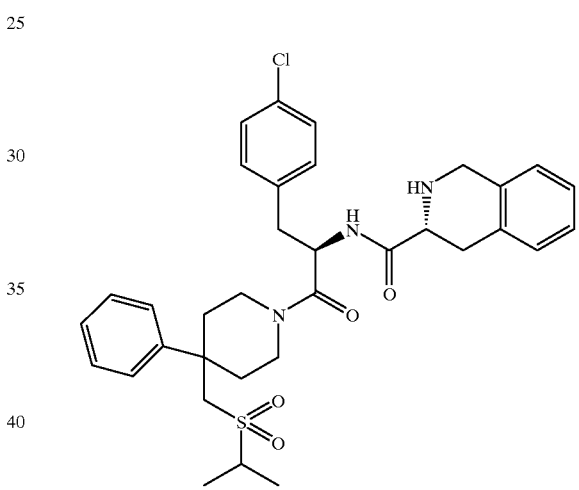
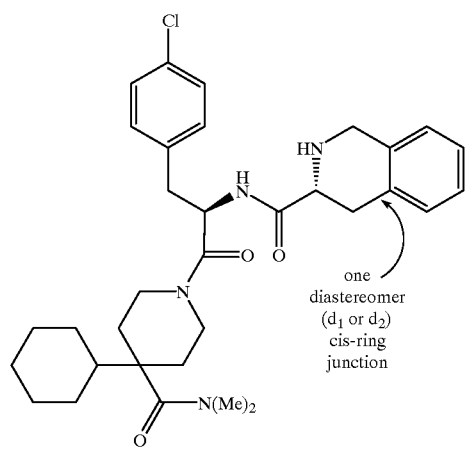
one diastereomer (d₁ or d₂) cis-ring junction
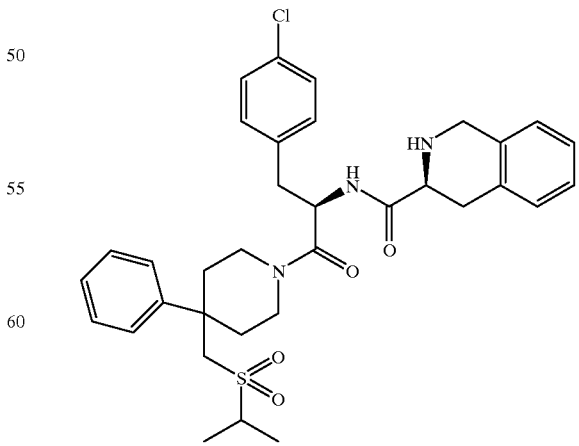

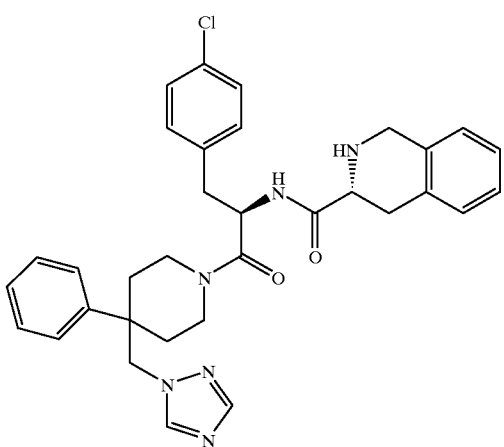
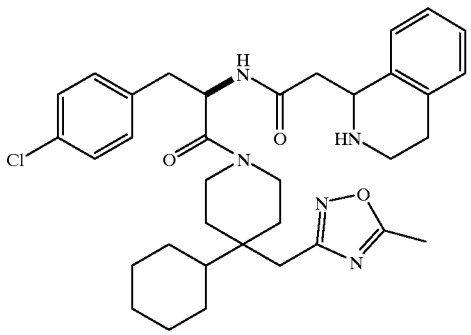
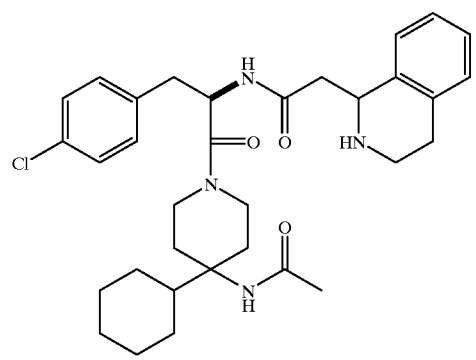
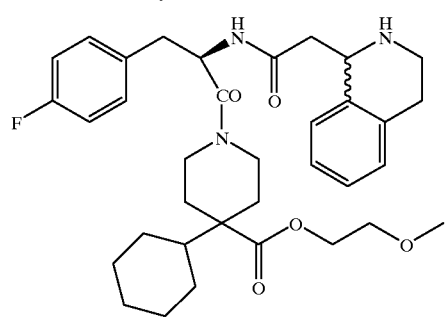
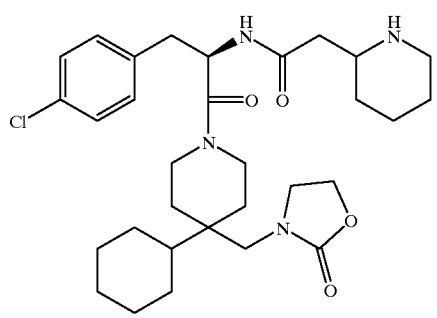
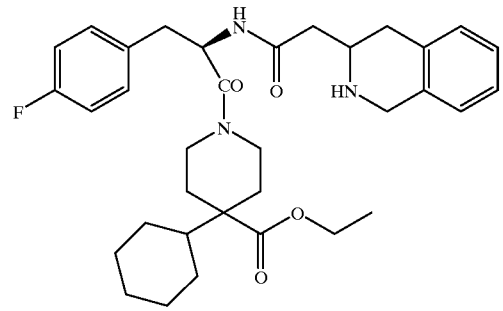
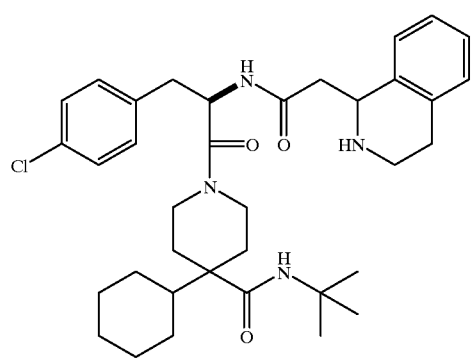
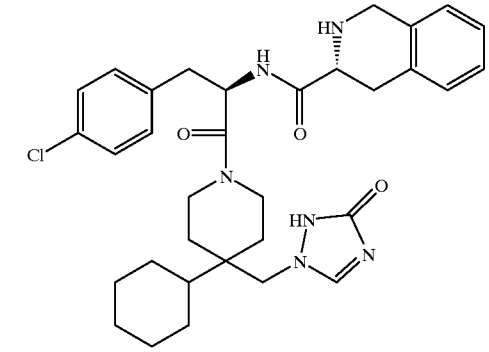
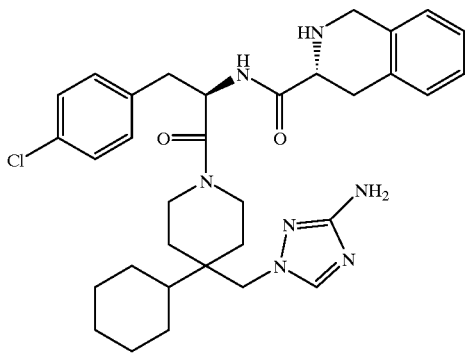

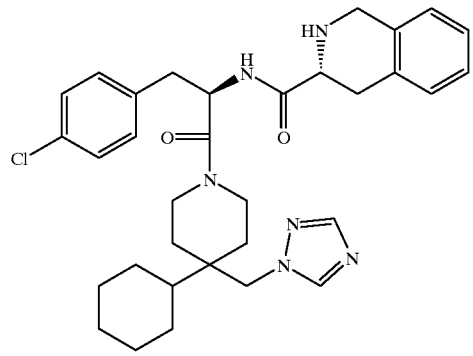
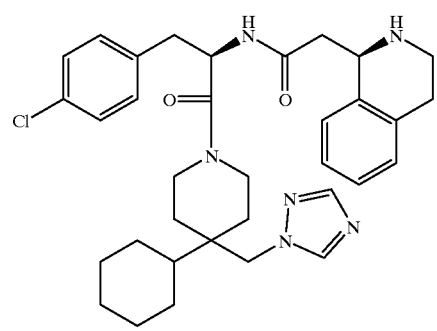
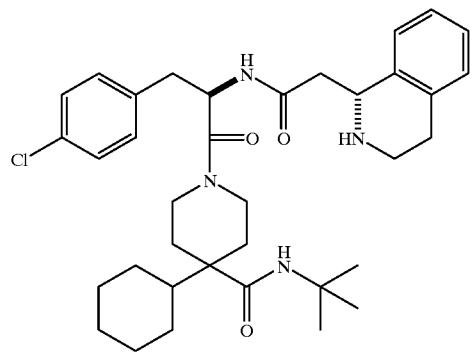
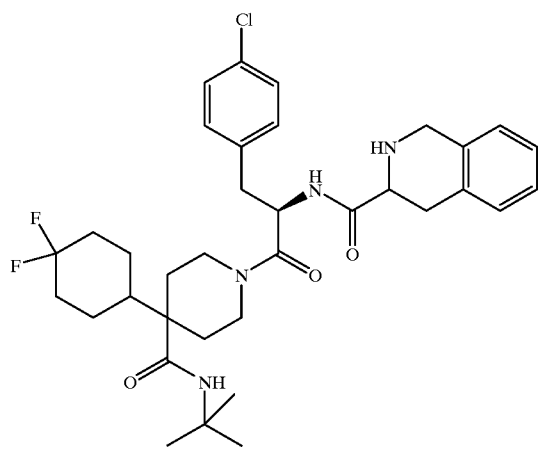
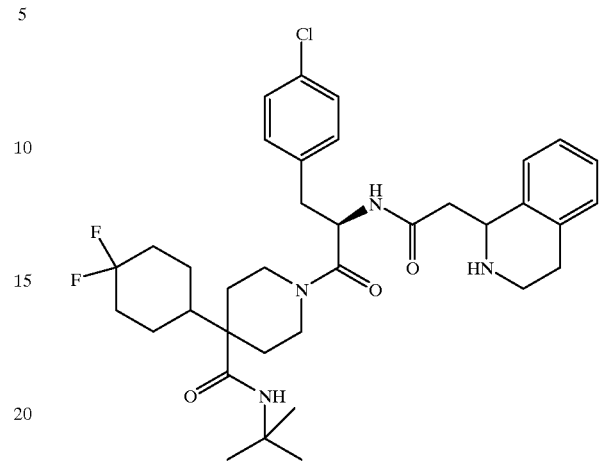
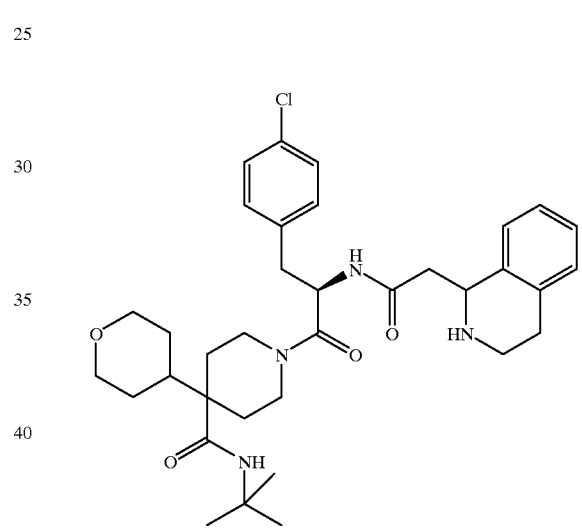
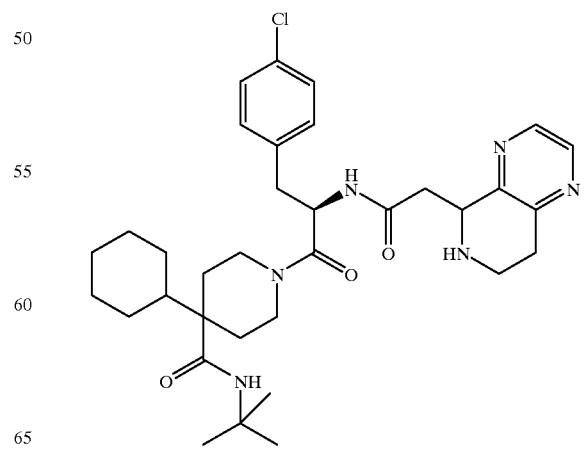

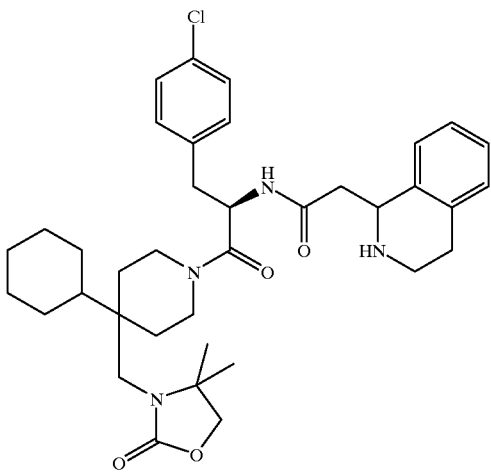

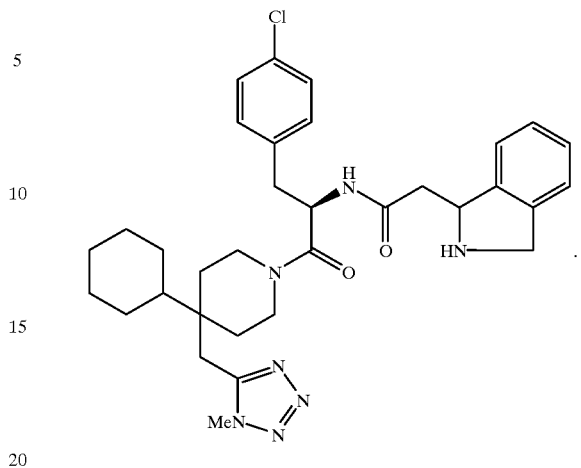

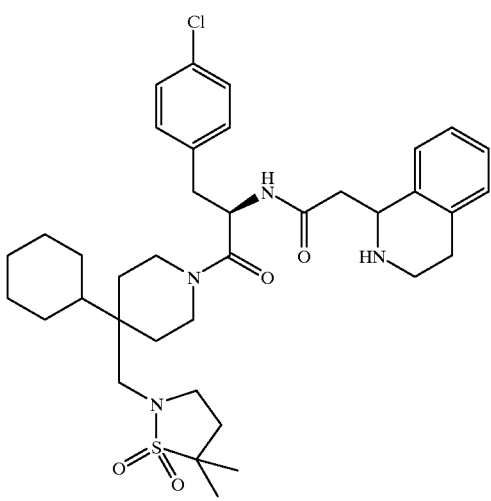

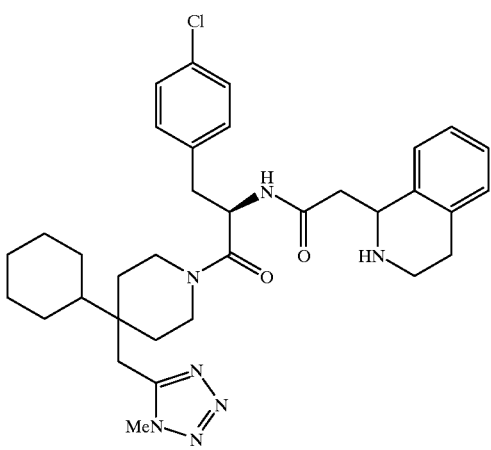

and

The compounds of Formula I are effective as melanocortin receptor agonists and are particularly effective as selective agonists of the human MC-4R. They are therefore useful for the treatment and/or prevention of disorders responsive to the activation of human MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal which comprises administering to said mammal an effective amount of a compound of formula I.

Another aspect of the present invention provides a method for the treatment or prevention of male or female sexual dysfunction including erectile dysfunction which comprises administering to a patient in need of such treatment or prevention an effective amount of a compound of formula I.

Another aspect of the present invention provides a method for the treatment of male or female sexual dysfunction including erectile dysfunction which comprises administering to a patient in need of such treatment an effective amount of a compound which is a selective agonist of the human melanocortin-4 receptor over each of the human MC-1R, MC-2R, MC-3R, and MC-5R, or any other human melanocortin receptor. In one embodiment of this aspect of the present invention, there is provided a method for the treatment of male or female sexual dysfunction which comprises administering to a patient in need of such treatment an effective amount of a compound which is a human MC-4R agonist wherein the compound binds to the human MC-4R with a binding affinity at least 10-fold higher than the compound binds to the human MC-1R, MC-3R, or MC-5R. In a class of this embodiment, the compound binds to the human MC-4R with a binding affinity at least 10-fold higher than the compound binds to the human MC-1R, MC-2R, MC-3R, and MC-5R. In a subclass of this class, the compound binds to the human MC-4R with a binding affinity at least 100-fold higher than the compound binds to the human MC-1R, MC-2R, MC-3R, and MC-5R.

In a second embodiment of this aspect of the present invention, the compound binds to the human MC-4R with a binding affinity at least 10-fold higher than the compound binds to any other human melanocortin receptor. In a class of this embodiment, the compound binds to the human MC-4R with a binding affinity at least 100-fold higher than the compound binds to any other human melanocortin receptor.

In a third embodiment of this aspect of the present invention, there is provided a method for the treatment of male or female sexual dysfunction which comprises administering to a patient in need of such treatment an effective amount of a compound which is a human MC-4R agonist wherein the functional activity at the MC-4R is characterized by an $EC_{50}$ at least 10-fold lower than the functional activity at the human MC-1R, MC-3R, or MC-5R. In a class of this embodiment, the functional activity at the human MC-4R is characterized by an $EC_{50}$ at least 10-fold lower than the functional activity at the MC-1R, MC-2R, MC-3R, and MC-5R. In a subclass of this class, the functional activity at the human MC-4R is characterized by an $EC_{50}$ at least 100-fold lower than the functional activity at the MC-1R, MC-2R, MC-3R, and MC-5R.

In a fourth embodiment of this aspect of the present invention, the functional activity at the human MC-4R is characterized by an $EC_{50}$ at least 10-fold lower than the functional activity at any other human melanocortin receptor. In a class of this embodiment, the functional activity at the human MC-4R is characterized by an $EC_{50}$ at least 100-fold lower than the functional activity at any other human melanocortin receptor.

In a further embodiment of this aspect of the present invention, there is provided a method for the treatment of male or female sexual dysfunction which comprises administering to a patient in need of such treatment an effective amount of a compound which is a human MC-4R agonist wherein the binding of the compound to the human MC-4R is characterized by an $IC_{50}$ less than 30 nanomolar (nM) and the binding of the compound to the human MC-1R, MC-3R, or MC-5R is characterized by an $IC_{50}$ greater than 30 nM. In a class of this embodiment, the binding of the compound to the human MC-1R, MC-2R, MC-3R, and MC-5R is characterized by an $IC_{50}$ greater than 30 nM. In a subclass of this class the binding of the compound to the human MC-1R, MC-2R, MC-3R, and MC-5R is characterized by an $IC_{50}$ greater than 100 nM. In a further subclass of this class, the binding of the compound to the human MC-1R is characterized by an $IC_{50}$ greater than 1000 nM, the binding to the human MC-2R and MC-3R by an $IC_{50}$ greater than 540 nM, and the binding to the human MC-5R by an $IC_{50}$ greater than 230 nM.

In yet a further embodiment, the binding of the compound to any other human melanocortin receptor is characterized by an $IC_{50}$ greater than 30 nM. In a class of this embodiment, the binding of the compound to any other human melanocortin receptor is characterized by an $IC_{50}$ greater than 100 nM. In a subclass of this class, the binding of the compound to any other human melanocortin receptor is characterized by an $IC_{50}$ greater than 500 nM.

Another aspect of the present invention provides a method for the oral treatment of male or female sexual dysfunction including erectile dysfunction which comprises the oral administration to the subject in need thereof a therapeutically effective amount of a compound which is an agonist of the human melanocortin-4 receptor. In one embodiment of this aspect of the present invention, the compound to be orally administered is a selective agonist of the human melanocortin-4 receptor. In another embodiment, the sexual dysfunction is erectile dysfunction. Generally, in man, the preferred route of administration of a drug is by the oral (PO) route, being the most convenient and avoiding the disadvantages associated with parenteral (such as subcutaneous, intravenous, and intramuscular) administration.

Yet another aspect of the present invention provides a pharmaceutical composition comprising a compound of formula I and a pharmaceutically acceptable carrier.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine, and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" are monocyclic heteroaromatic rings, examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^b R^b$ may represent $NH_2$, $NHCH_3$, $N(CH_3)CH_2CH_3$, and the like.

The term "composition", as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereoisomers—Geometric Isomers—Tautomers

Compounds of Formula I contain one or more asymmetric centers and can thus occur as racemates and racemic mixtures, single enantiomers, diastereoisomeric mixtures and individual diastereoisomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of Formula I.

Compounds of the Formula I may be separated into their individual diastereoisomers by, for example, fractional crystallization from a suitable solvent, for example methanol or ethyl acetate or a mixture thereof, or via chiral chromatography using an optically active stationary phase.

Alternatively, any diastereoisomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds of formula I show highly specific activity toward the melanocortin-4 receptor which makes them especially useful in the prevention and treatment of obesity, as well as male and female sexual dysfunction, including erectile dysfunction.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/ or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formnula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that are used in the treatment/prevention/ suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847;
(ii) biguanides such as metformin and phenformin;
  (b) insulin or insulin mimetics;
  (c) sulfonylureas such as tolbutamide and glipizide;
  (d) α-glucosidase inhibitors (such as acarbose),
  (e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;
  (f) PPARδ agonists such as those disclosed in WO97/28149;
  (g) antiobesity compounds such as fenfluramine, dexfenfluramine, phentermine, sibutramine, orlistat, or $\beta_3$ adrenergic receptor agonists;
  (h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
  (i) PPARα agonists such as described in WO 97/36579 by Glaxo;
  (j) PPARγ antagonists as described in WO97/10813;
  (k) serotonin reuptake inhibitors such as fluoxetine and sertraline;
  (l) growth hormone secretagogues such as MK-0677; and
  (m) agents useful in the treatment of male and/or female sexual dysfunction which include phosphodiesterase V (PDE-V) inhibitors, such as sildenafil and IC-351; $\alpha_2$-adrenergic receptor antagonists, such as phentolamine mesylate; and dopamine-receptor agonists, such as apomorphine.

Biological Assays

A. Binding Assay. The membrane binding assay was used to identify competitive inhibitors of $^{125}$I-NDP-alpha-MSH binding to cloned human MCRs expressed in L- or CHO-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 ml 10,000 unit/ml penicillin & 10,000 ug/ml streptomycin (Gibco/BRl); 10 ml 200 mM L-glutamine (Gibco/BRl); 1 mg/ml Geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 minutes or until cells sloughed off when flask was banged against hand.

The cells were harvested into 200 ml centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 minutes.

The pellets were resuspended in 0.2 mls/monolayer membrane prep buffer and aliquots were placed in tubes (500–1000 ul/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl2; 1 mM MgCl2; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred μl of membrane binding buffer containing 10–40 ug membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 ml per well) with room temperature of filter wash having the composition: 50 mM Tris-HCl pH 7.2 and 20 mM NaCl. The filter was dried, and the bottom sealed and 50 ul of Packard Microscint-20 was added to each well. The top was sealed and the radioactivity quantitated in a Packard Topcount Microplate Scintillation counter.

B. Functional assay. Functional cell based assays were developed to discriminate melanocortin receptor agonists from antagonists.

Cells (for example, CHO- or L-cells or other eukaryotic cells) expressing a human melanocortin receptor (see e.g. Yang-YK; Ollmann-MM; Wilson-BD; Dickinson-C; Yamada-T; Barsh-GS; Gantz-I; Mol-Endocrinol. 1997 Mar; 11(3): 274–80) were dissociated from tissue culture flasks by rinsing with Ca and Mg free phosphate buffered saline (14190–136, Life Technologies, Gaithersburg, Md.) and detached following 5 minutes incubation at 37° C. with enzyme free dissociation buffer (S-014-B, Specialty Media, Lavellette, N.J.). Cells were collected by centrifugation and resuspended in Earle's Balanced Salt Solution (14015–069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to 5×10$^6$/ml. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min., cells were lysed by incubation at 100° C. for 5 min. to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH at 10 μM which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min., and an EC50 dose (approximately 10 nM alpha-MSH) was added to the cells. The assay was terminated at 45 min. and cAMP quantitated as above. Percent inhibition was determined by comparing the amount of cAMP produced in the presence to that produced in the absence of test compound.

C. In vivo food intake models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

Preparation of Compounds of the Invention

The preparation of compounds of Formula I of the present invention may be carried out using sequential or convergent synthetic routes. Syntheses detailing the preparation of the compounds of Formula I in a sequential manner are presented in the following reaction schemes. The instant compounds are generally isolated in the form of their pharmaceutically acceptable salts, such as those described previously hereinabove.

The phrase "standard peptide coupling reaction conditions" means coupling a carboxylic acid with an amine using an acid activating agent such as EDC, DCC, and BOP in a inert solvent such as dichloromethane in the presence of a catalyst such as HOBT. The use of protecting groups for amine and carboxylic acid to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation with hydrogen in the presence of a noble metal or its oxide such as palladium on activated carbon in a protic solvent such as ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out in a solvent such as methylene chloride, methanol, or ethyl acetate, with a strong acid, such as trifluoroacetic acid, hydrochloric acid, or hydrogen chloride gas.

Abbreviations Used in the Description of the Preparation of the Compounds of the Present Invention:

| | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ESI-MS | electron spray ion-mass spectroscopy |
| Et | ethyl |
| EtOAc | ethyl acetate |
| HATU | N-[(dimethylamino)-1H-1,2,3-triazolo[4,5-b]pyridin-1-ylmethylene]-N-methylmethanaminium hexafluorophosphate N-oxide |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| Ms | methanesulfonyl |
| NMM | N-methylmorpholine |
| OIC | octahydroindole-2-carboxylic acid |
| Ph | phenyl |
| Phe | phenylalanine |
| Pr | propyl |
| prep. | prepared |
| PyBrop | bromo-tris-pyrrolidino-phosphonium hexafluorophosphate |
| TFA | trifluoroacetic acid |
| THF | tetrahydrofuran |
| Tic | 1,2,3,4-tetrahydroisoquinoline-3-carboxylic acid |
| Tic(OH) | 7-hydroxy-1,2,3,4-tetrahydroisoquinoline-3-carboxylic acid |
| TLC | thin-layer chromatography |

Intermediates of formula 3 may be synthesized as illustrated in Scheme 1 by coupling a protected amino acid of formula 1 (where Q is a protecting group) with a piperidine derivative of formula 2 under standard peptide coupling conditions. The protected amino acid derivatives 1 are commercially available or may be prepared by literature methods (Williams, R. M., *Synthesis of Optically Active α-Amino Acids*, Pergamon Press: Oxford, 1989). Similarly, piperidines of formula 2 are either commercially available, known in the literature, or may be prepared following literature methods described for analogous compounds. Some of these methods are illustrated in the subsequent schemes. Removal of the protecting group Q (CBZ, BOC, etc.) is accomplished using conventional methods. The skills required in carrying out the reaction and purification of the resulting reaction products are known to those in the art. Purification procedures include crystallization and normnal-phase or reverse-phase chromatography.

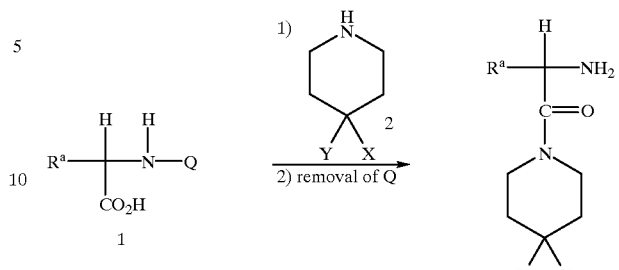

Scheme 1

Compounds of Formula I ($R^e$=H) may be prepared as shown in Scheme 2 by coupling intermediates of Formula 3 to protected amino acids of Formula 5 (Q=protecting group such as Boc, CBZ, FMOC, etc.) under standard peptide-type coupling reaction conditions. Amino acids 5 are either commercially available or can be synthesized by known methods such as those described later.

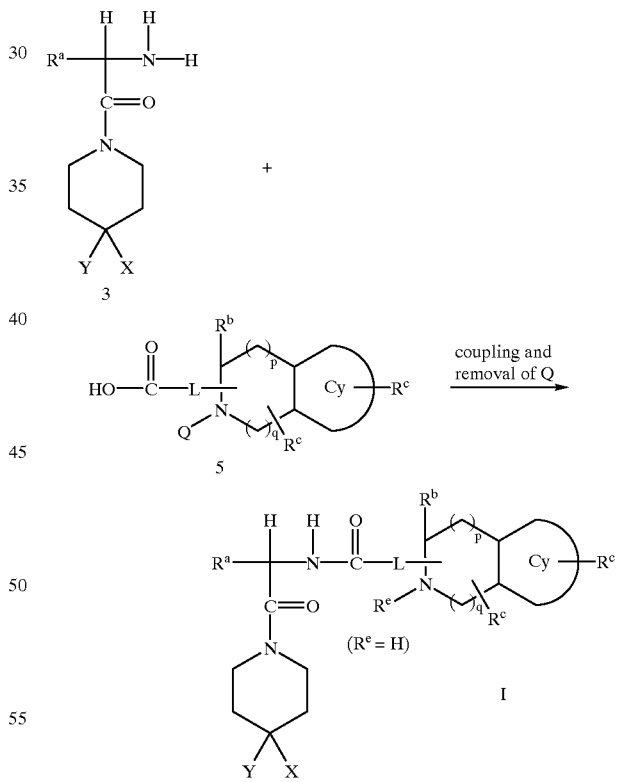

SCHEME 2

Compounds of Formula I, wherein $R^e$ is other than H, can be prepared from a compound of Formula I wherein $R^e$ is H as shown in Scheme 3 by reductive amination to introduce an alkyl or substituted alkyl group, or by acylation, sulfonylation or coupling with protected amino acids. If a protected amino acid is used, deprotection has to be carried out to liberate the amine functionality.

Scheme 3

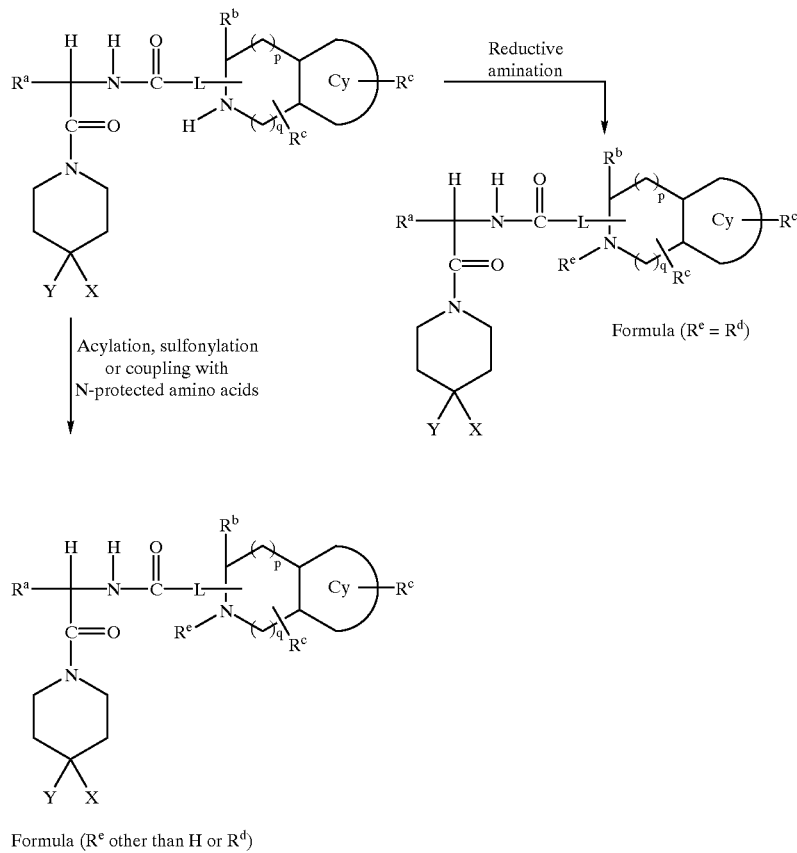

Formula ($R^e$ other than H or $R^d$)

Compounds of Formula I may also be prepared directly by coupling acids of formula 5a with intermediate 3 as shown in Scheme 4.

SCHEME 4

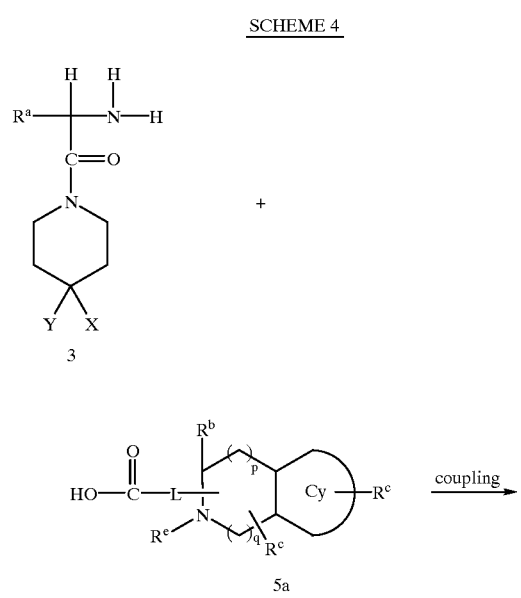

-continued

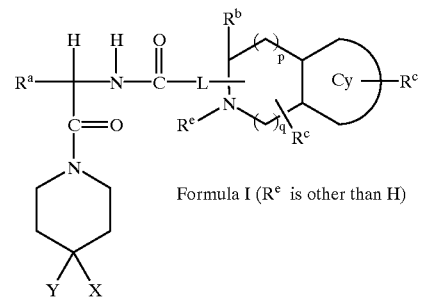

Formula I ($R^e$ is other than H)

Compounds of Formula I of the present invention may also be prepared in a convergent manner as described in Scheme 5. Amino acid ester intermediate 6, wherein Q' is a small alkyl such as methyl or ethyl or a benzyl or allyl unit, can be synthesized by well documented methods in the literature. Coupling of intermediates 5b (wherein T is an amino protecting group or non-H $R^e$ group) and 6 under standard peptide coupling conditions followed by removal of the ester group Q' yields the intermediate 7.

Scheme 5

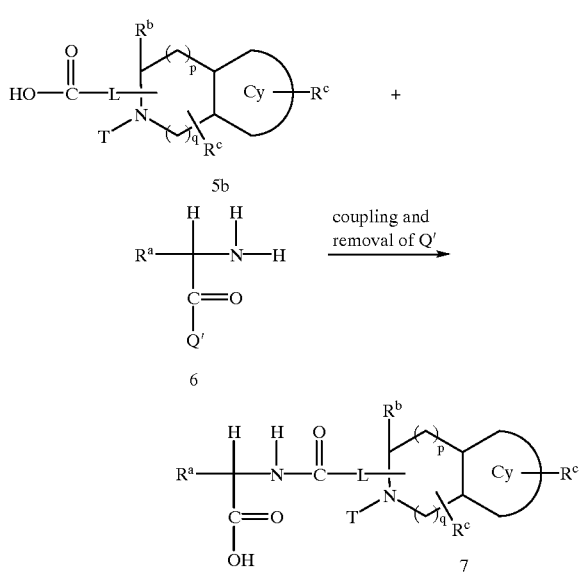

As shown in Scheme 6, compounds of Formula I are obtained by coupling intermediates of Formula 7 (T=amino protecting group or a non-H $R^e$ group) to piperidines of formula 2 under standard peptide coupling reaction conditions, followed by the removal of the amino protecting group, if necessary.

SCHEME 6

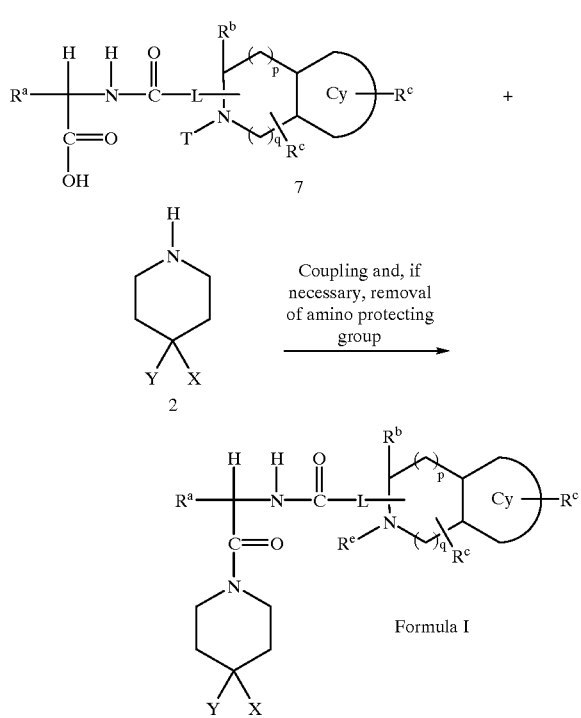

The compounds of the present invention may also be prepared from a variety of substituted natural and unnatural amino acids of formula 8a.

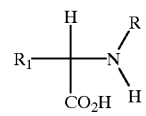

The preparation of many of these acids is described in U.S. Pat. No. 5,206,237, which is incorporated by reference herein in its entirety. The preparation of these intermediates in racemic form is accomplished by classical methods familiar to those skilled in the art (Williams, R. M. "Synthesis of Optically Active α-Amino Acids" Pergamon Press: Oxford, 1989). Several methods exist to resolve (DL)-amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereoisomers either by chromatographic techniques or by crystallization followed by hydrolysis of the chiral amide furnishes resolved amino acids. Similarly, amino protected intermediates may be converted to a mixture of chiral diastereoisomeric esters and amides. Separation of the mixture using methods described above and hydrolysis of the individual diastereoisomers provides (D)- and (L)-amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("Asymmetric Synthesis, Chiral Catalysis; Morrison, J. D., Ed; Academic Press: Orlando, Fla., 1985; Vol 5), and (6) enzymatic syntheses (*Angew. Chem. Int. Ed. Engl.* 1978, 17, 176).

For example, as illustrated in Scheme 7, alkylation of the enolate of diphenyloxazinone 9 (*J. Anm. Chtem. Soc.* 1991, 113, 9276) with p-trifluoromethoxybenzyl bromide in the presence of sodium bis(trimethylsilyl)amide proceeds smoothly to afford 10 which is converted into the desired (D)-amino acid 11 by removing the N-t-butyloxycarbonyl group with trifluoroacetic acid and hydrogenation over a $PdCl_2$ catalyst.

SCHEME 7

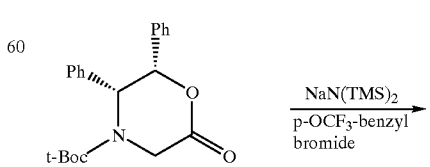

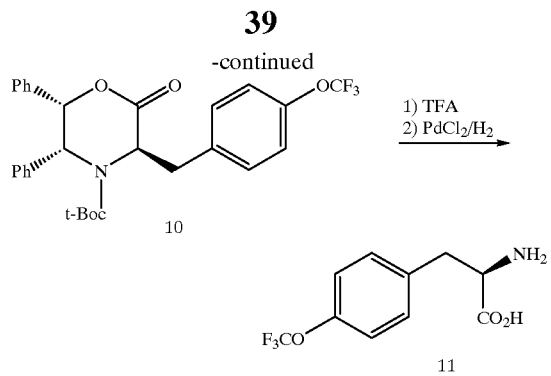

Piperidines of Formula 2 may be prepared according to the methods described below. These piperidines can be further elaborated to melanocortin receptor compounds of the present invention using chemistry that is detailed in Schemes 1–7 above.

SCHEME 8

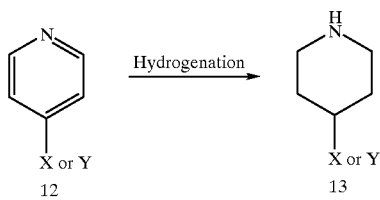

4-Substituted piperidines of formula 13 can be prepared by the reduction of pyridine derivatives or their salts by hydrogenation in a suitable solvent such as water, acetic acid, alcohol, e.g. ethanol, or their mixture, in the presence of a noble metal catalyst such as platinum or an oxide thereof on a support such as activated carbon, and conveniently at room temperature and atmospheric pressure or under elevated temperature and pressure. 4-Monosubstituted piperidines can also be prepared by modification of the X or Y moiety of the existing 4-monosubstituted piperidines.

SCHEME 9

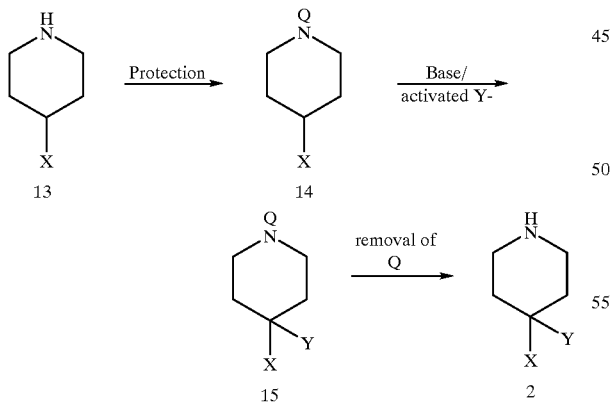

Illustrated in Scheme 9 is a general way to prepare di-substituted piperidines. Compounds of Formula 13 wherein X is an electron-withdrawing group such as —CN, —$CO_2R^d$, where $R^d$ is alkyl, aryl, and ($C_1$–$C_4$alkyl)aryl are known compounds or may be prepared by methods analogous to those used for the preparation of such known compounds. The secondary amine of compounds of Formula 13 may be first protected by a protecting group Q such as BOC and CBZ using the conventional techniques. Introduction of the Y substitution can be achieved by first reacting compounds of Formula 14 with a strong base such as lithium bis(trimethylsilyl)amide, lithium diisopropylamide following by addition of alkylating or acylating reagents such as alkyl halides, aryl alkyl halides, acyl halides, and haloformates in a inert solvent such as THF at temperatures from −100° to room temperature. The halides used in these reactions are either commercially available or known compounds in the literature or may be prepared by methods analogous to those used for the preparation of known compounds. The protecting group Q in compounds of formula 15 may be removed with conventional chemistry to give compounds of Formula 2.

A second synthesis of piperidines of formula 2, wherein X=$CO_2Et$, involves alkylation of ethyl arylacetate 16 with a protected bis(chloroethyl)amine 17 (*J. Pharm. Sci.* 1972, 61, pp 1316–1317) to afford piperidines of formula 18. This reaction requires two equivalents of a strong base such as sodium hydride or lithium diisopropylamide and is carried out conveniently in aprotic solvents such as THF. The Q protecting group can be removed and elaborated to ester-based melanocortin receptor agonists of the present invention. Alternatively, the ester group can be hydrolyzed to acid 19 and converted to amides of formula 20 by standard chemical methods (see Scheme 10).

SCHEME 10

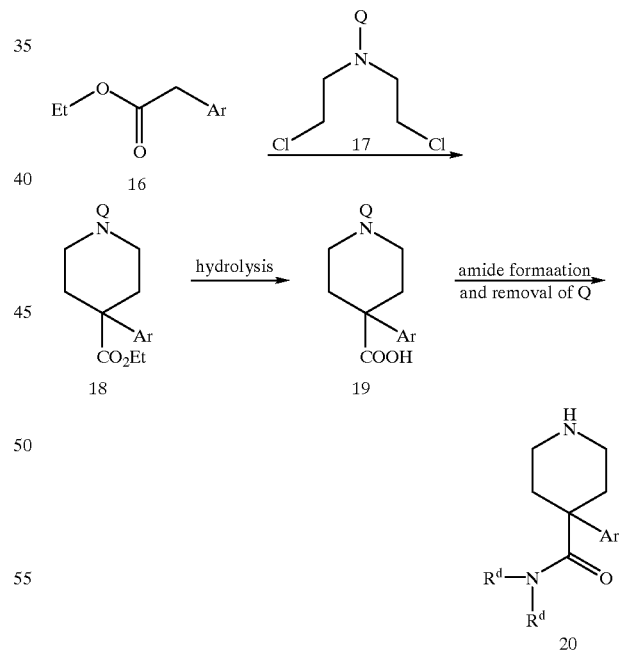

As illustrated in Scheme 11, intermediates such as 18 and 20 can be hydrogenated with Pt/C or Rh/alumina as catalysts in solvents such as methanol, ethanol or acetic acid to afford cyclohexyl derivatives 21 and 22. High pressures are often required to carry out this hydrogenation reaction. The Q protecting group can be removed by standard methods as discussed above.

SCHEME 11

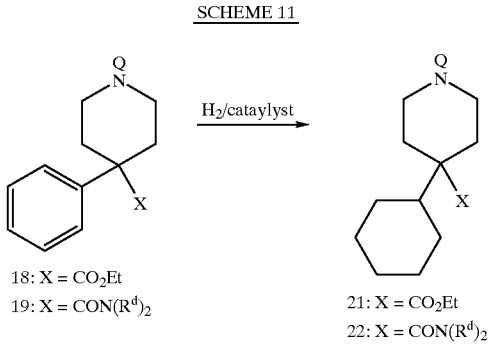

18: X = CO$_2$Et
19: X = CON(R$^d$)$_2$

21: X = CO$_2$Et
22: X = CON(R$^d$)$_2$

The X and Y functionalities in compounds of general structure 18 and 21 may be further elaborated to provide groups not accessible by direct alkylation as illustrated in Scheme 12. For example, in compound 21 the carboxylic acid can be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.*, 57, 7194–7208 (1992). These methods may be repeated to provide an X substituent of the desired alkylene chain length. The protecting group Q may be removed through conventional chemistry.

SCHEME 12

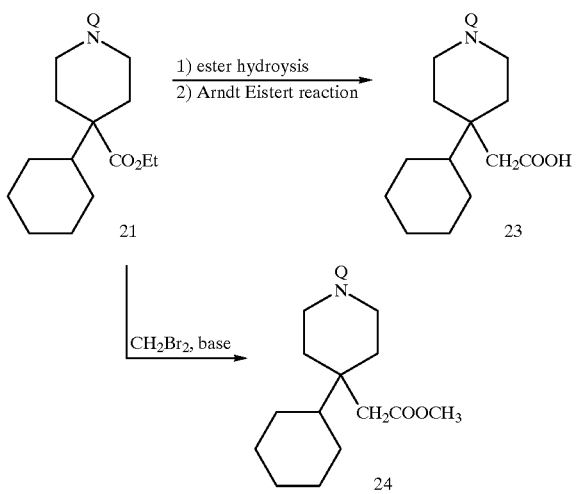

As illustrated in Scheme 13, the ester functionality in compounds such as 21 can be reduced to alcohol 25 with the reagents such as DIBALH or lithium aluminum hydride in solvents such THF or diethyl ether. Mesylation of the alcohol affords 26 which can be reacted further with anions of heterocycles such as triazole, imidazole, tetrazole to afford heterocyclic piperidines 27 (P=heterocycle). Piperidines of formula 27 where P is a heterocycle can also be prepared directly from alcohol 25 via a Mitsunobu reaction.

Displacement of the mesylate 26 with sodium cyanide or sodium azide affords piperidine wherein P is CN or N$_3$, respectively. In compounds of formula 27 where P is N$_3$, the azido functionality can be reduced to an amino group with the use of triphenylphosphine in THF-water or Pd/C-mediated hydrogenation. The amine functionality may be converted to amides, sulfonamides, ureas, etc. by standard chemical methods. The protecting group Q can be removed and elaborated to compounds of the present invention using chemistry described in Schemes 1–8.

SCHEME 13

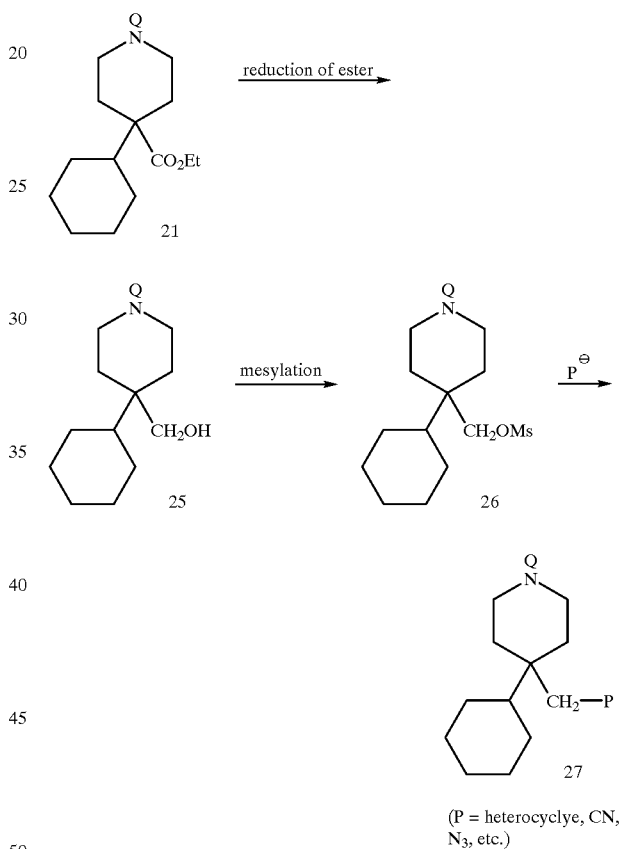

(P = heterocyclye, CN, N$_3$, etc.)

As illustrated in Scheme 14 compounds in which an oxygen atom is directly attached to the piperidine ring may be conveniently prepared by addition of an activated form of an alkyl, aryl, alkylaryl group, such as lithium reagent, Grignard reagents, and the like with a ketone 28, which is commercially available. The resulting hydroxy group may be further derivatized by acylation, sulfonylation, alkylation, and the like using conventional chemistry. Removal of the Q protecting group may be carried out under the usual conditions to give compounds of general formula 31.

SCHEME 14

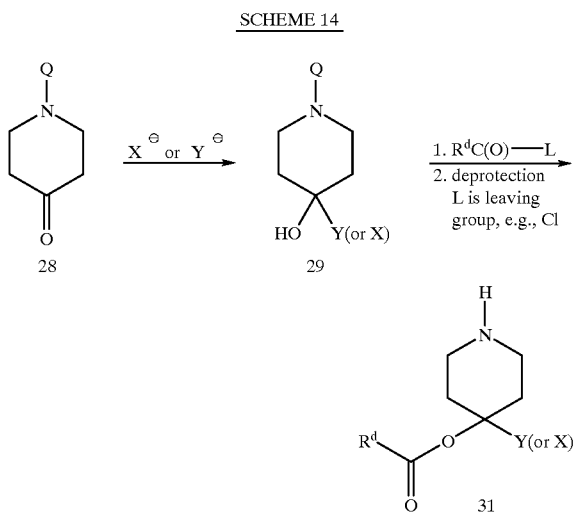

As illustrated in Scheme 15, compounds where a nitrogen atom is directly attached to the piperidine ring may be conveniently prepared via the Curtius rearrangement. For example, acid 25 is converted to the corresponding acyl azide, which is refluxed in an organic solvent to afford the isocyanate 32. Addition of amines or alcohols to the isocyanate gives ureas or carbamates, respectively. Hydrolysis of the isocyanate provides amine 33, which may be further derivatized by acylation, sulfonylation, alkylation, and the like through conventional chemistry. Removal of the protecting group Q may be accomplished as described previously.

SCHEME 15

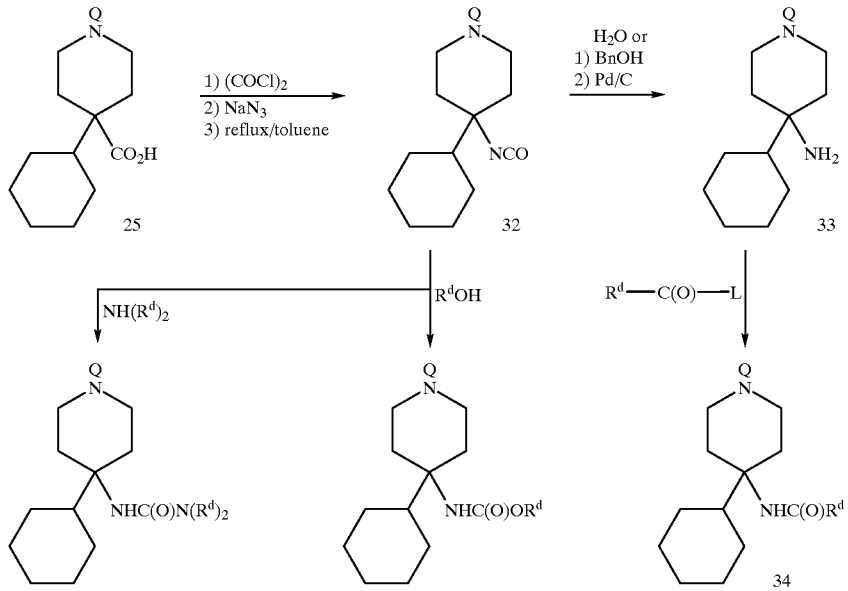

Compounds of the general formula 2 in which X and Y are not identical are generally obtained as a racemic mixture. Resolution of the two enantiomers can be conveniently achieved by classical crystallization methods by using a chiral acid such as L- or D-tartaric acid, (+) or (−)-10-camphorsulfonic acid in a suitable solvent such as acetone, water, alcohol, ether, acetate or their mixture. Alternatively, a racemic amine 2 can be reacted with a chiral auxiliary such as (R)- or (S)-O-acetylmandelic acid followed by chromatographic separation of the two diastereoisomers, and removal of the chiral auxiliary by hydrolysis. Alternatively asymmetric alkylation can also be utilized for the synthesis of an optically active intermediate by introducing a removable chiral auxiliary in X or in place of L with subsequent chromatographic separation of diastereoisomers.

Piperidines 2 containing a sulfide substituent may be converted to the corresponding sulfoxide or sulfone using oxidizing agents such as sodium periodate, m-chloroperbenzoic acid or Oxone in a solvent such as dichloromethane, alcohol, water or a mixture thereof.

Protected amino acids of formula 5, wherein L is a suitable protecting group such as Boc or CBZ, can by conveniently synthesized by methods well documented in the literature.

5

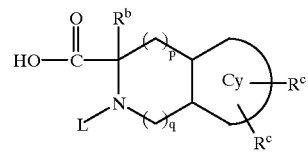

For example, as shown in Scheme 16, a substituted phenylalanine derivative 35 can be treated with aqueous formaldehyde in concentrated hydrochloric acid to afford, after protection of the amino functionality in a second step by well-documented methods, the tetrahydroisoquinoline compound 37. This reaction can also be effected with heterocyclic amino acids such as 2- and 3-thienyl alanine. Since the above chemistry works generally with retention of stereochemistry, D- and L-acids of general formula 5 can be prepared from D- and L- amino acids, respectively.

SCHEME 16

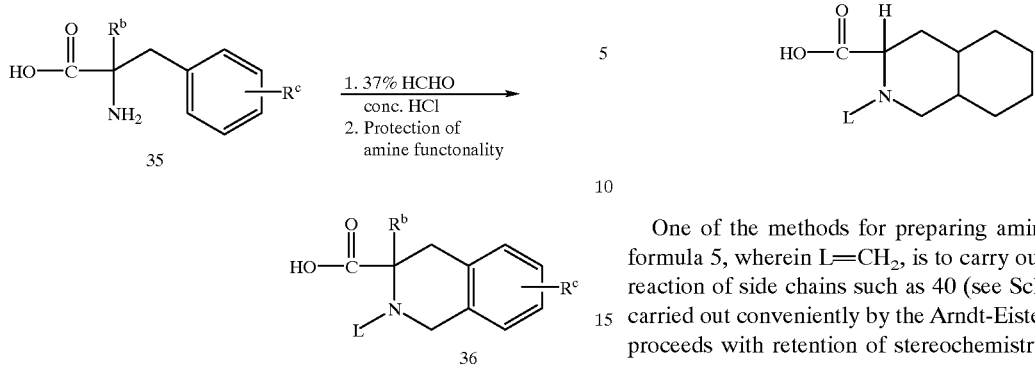

As shown in Scheme 17, a second method to prepare compounds of formula 5 includes alkylation of a dihalide (L=Br, Cl, I) of formula 37 with dimethylacetamidomalonate in the presence of a strong base such as NaH in DMF to afford alkylated material of formula 38. Treatment of esters of formula 38 with alkali leads to formation of the corresponding mono carboxylic acid which can be treated with refluxing hydrochloric to affect hydrolysis of the acetamide derivative to provide amino acid of formula 39. Once again, standard protection of the amino functionality provides intermediates of formula 40.

SCHEME 17

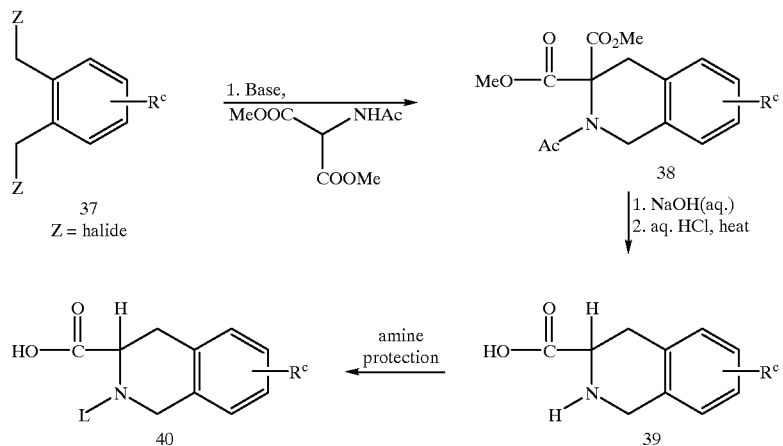

Saturated amino side chains of formula 41 can be prepared by hydrogenating compounds of formula 40 in the presence of rhodium or platinum catalysts. For example, following the method of Omstein and coworkers (Ornstein, P. L.; Arnold, M. B.; Augenstein, N. K.; Paschal, J. W. *J. Org. Chem.* 1991, 56, 4388), compound 40 can be hydrogenated in the presence of 5% Rh on alumina to give compound 41. Individual diastereoisomers of 41 can be resolved via classical resolution methods.

One of the methods for preparing amino side chains of formula 5, wherein L=$CH_2$, is to carry out a homologation reaction of side chains such as 40 (see Scheme 18). This is carried out conveniently by the Arndt-Eistert reaction which proceeds with retention of stereochemistry. Other methods involve require reduction of the acid or its ester derivative to an alcohol, conversion of the alcohol to a leaving group such as a mesylate or halide, displacement of it with cyanide anion and hydrolysis of the nitrile to the carboxylic acid by well documented literature methods.

SCHEME 18

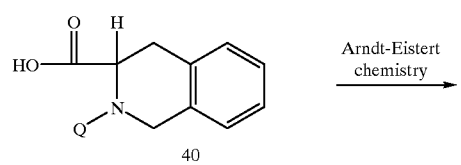

-continued

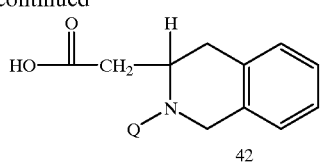

Side chains such as 44 can be prepared by a one carbon homologation reaction of isoquinoline carboxylic acid of formula 43 as described above. Partial reduction of the pyrido portion of 43 (Scheme 19) with a hydrogenation catalyst such as platinum oxide or Pt/C in an alcoholic solvent affords tetrahydroisoquinoline 44. Protection of the amino functionality affords side chains that can used to prepare compounds of Formula I.

SCHEME 19

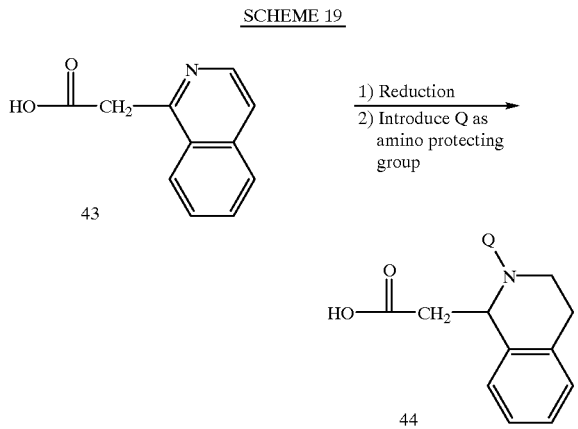

It is understood that in some cases the order of carrying out the foregoing reaction schemes may be varied to facilitate the reaction or to avoid unwanted reaction products.

PREPARATION OF INTERMEDIATES

Compounds of the present invention may be prepared using commercially available starting materials, or intermediates that are synthesized from commercially available materials by methods well known to one skilled in the art. The following section provides illustrative procedures for preparing intermediates useful in the preparation of present compounds; it will be appreciated that the choice of reagents, choice of solvents, reaction conditions and the like may be varied, and the selection of such variables is within the skills of one of ordinary skill in the art.

INTERMEDIATE 1

4,4-DISUBSTITUTED PIPERIDINES

Intermediate 1a(i): Ethyl 4-cyclohexyl-4-piperidinecarboxylate

Ethyl 4-phenyl-4-pipeiidinecarboxylate HCl (Aldrich, 3.56 g, 13.2 mmol) was dissolved in a mixture of 10 mL concentrated HCl and 40 ML of methanol. Platinum(IV) oxide (0.60 g, 2.64 mmol) was added slowly in a hydrogenation vehicle. The bottle was placed on a shaker and the mixture was shaken for 4 days under hydrogen (45 psi) at room temperature. The catalyst was removed by filtration and solid was washed with methanol (3×20 mL). The volatiles were emoved to provide the desired title compound (3.44 g).

Intermediate 1a(ii): Ethyl 4-(4-tetrahydropyranyl)-4-pipeiidinecarboxylate HCl

Step A: Ethyl 1-BOC4-(4-hydroxy-4-tetrahydropyranyl)-4-piperidinecarboxylate

To a solution of ethyl N-Boc-4-piperidinecarboxylate (2.57 gm; 10.0 mmol) in 100 mL of dry THF was added 6.0 mL (2.0 M) of LDA at −78° C. The mixture was stirred at −78° C. for half hour, and then a solution of tetrahydro-4H-pyran-4-one (2.0 gm; 20.0 mmol) in 5.0 mL dry THF was added thereto. The resultant mixture was stirred at −78° C. for two hours and then warmed up to room temperature and kept for overnight. Saturated ammonium chloride (200 mL) was added and the aqueous layer was extracted with ethyl acetate (3×150 mL). The organic layer was washed with brine and dried over magnesium sulfate, filtered and then concentrated. The crude product was purified by flash chromatography (hexane/ethyl acetate 2:1) to give 1.47 gm of the desired product.

Step B: Ethyl 4-(5,6-dihydro-2H-4-pyranyl)-4-piperidinecarboxylate

Methanesulfonic acid (1.48 gm; 15.4 mmol) was add to the alcohol of Step A (1.07 gm; 2.99 mmol) in TMF at 0° C. The reaction mixture was then warmed to 60° C. and stirred overnight. Water was added and 1N NaOH was added until mixture turned to basic. The aqueous layer was extracted with ethyl acetate (3×100 mL). The organic layer was washed with brine and then dried over magnesium sulfate, filtered and then concentrated to give 0.47 gm of the title compound.

Step C: Ethyl 4-(4-tetrahydropyranyl)-4-piperidinecarboxylate HCl

To a suspension of platinum oxide (0.24 gm; 0.87 mmol) in ethanol (40 mL) and conc HCl (10 mL) was added the compound from Step B (0.41 gm; 1.71 mmol). The reaction mixture was purged with hydrogen and then shaken under a hydrogen atmosphere (50 psi) for 20 hours. The mixture was purged with nitrogen and filtered through celite and washed with EtOH and concentrated to give the title compound (0.36 gm) as a white solid.

Intermediate 1a(iii): Ethyl 4-(n-butyl)-4-piperidinecarboxylate trifluoroacetate salt To a solution of ethyl N-Boc-4-piperidinecarboxylate (2.3 g, 9 mmol) in THF (60 mL) at −78° C. was added LDA (2.0M in heptane/THF/ethylbenzene) (5.1 mL, 9.9 mmol). The solution was stirred at −78° C. for 45 min. n-Butyliodide (1.53 mL, 13.5 mmol) was added dropwise and the reaction allowed to warm to rt over 1 hr. Volatiles were removed in vacuo and the residue partitioned between EtOAc (150 mL) and water (150 mL). The organic phase was washed with 0.5M HCl, saturated aqueous $NaHCO_3$ and brine, dried over $Na_2SO_4$ and concentrated. Chromatography over silica eluting with 1:9 EtOAc/hexane afforded the N-BOC protected title compound as a clear colourless oil (1.93 g, 6.15 mmol, 68%).

A solution of the protected title compound (1.4 g, 4.5 mmol) in $CH_2Cl_2$ (160 mL) and TFA (40 mL) was stirred at rt for 1 hr. Volatiles were removed in vacuo to afford the title compound as a clear colourless gum (1.46 g, 4.5 mmol, quant.). ESI-MS calcd for $C_{17}H_{31}NO_4$: 313; found 256 (M-$^t$Bu).

Intermediate 1b(i): 1-Boc-4-cyclohexyl-4-piperidinemethanol

To a stirred suspension of lithium aluminium hydride (3 g, 80 mmol) in THF (100 mL) at 0° C. was added a solution of ethyl 4-cyclohexyl-4-piperidine-carboxylate (4.8 g, 20 mmol) in THF (200 mL). The reaction mixture was allowed to warm to rt, stirred for a further 90 hours, then recooled to 0° C. and quenched with saturated aqueous $NH_4Cl$. The resultant grey emulsion was diluted with 3:10:87 $Et_3N$/MeOHEtOAc (500 mL) and filtered through a short pad of celite, rinsing with EtOAc (250 mL). The filtrate was washed with brine, dried over $Na_2SO_4$ and evaporated in vacuo to afford a white solid. NMR analysis of the crude product showed it to be a mixture of aldehyde and alcohol (1.5:1).

The crude product was dissolved in 1:9 $Et_3N$/MeOH (150 mL). Di-tert-butyldicarbonate (6.5 g, 30 mmol) was added and the solution stirred at rt for 4 hr. Volatiles were removed in vacuo, the residue was dissolved in EtOAc (200 mL), washed successively with saturated aqueous NaHCO$_3$, water and brine, dried over Na$_2$SO$_4$ and concentrated to afford a clear colourless oil. Crude chromatography through silica eluting with 1:1 EtOAc/hexane afforded a mixture of BOC-protected aldehyde and alcohol (1.5:1) as a clear colourless oil.

To a solution of this mixture in MeOH (200 mL) at 0° C. was added NaBH$_4$ (378 mg, 10 mmol). The reaction was stirred at 0° C. for 30 min. Solvent was removed in vacuo and the residue partitioned between saturated aqueous NH$_4$Cl (200 mL) and EtOAc (200 mL). The aqueous phase was extracted with EtOAc (200 mL). The combined organic phases were washed with water and brine, dried over Na$_2$SO$_4$ and evaporated to afford the title alcohol as a white solid (4.97 g, 16.7 mmol, 84%). ESI-MS calcd for C$_{17}$H$_{31}$NO$_3$: 297; found 297 (M).

Intermediate 1b(ii): 1-Boc-4-phenyl-4-piperidinemethanol

To a stirred solution of N-Boc-4-phenyl-4-piperidinecarboxylic acid (4.6 g, 15 mmol) in TBF (200 mL) at 0° C. was added borane-dimethylsulfide complex (10M in THF) (6 mL, 60 mmol). The reaction mixture was allowed to warm to rt and stirred for 3 hr before recooling to 0° C. H$_2$O$_2$ (30% aqueous) (20 mL) followed by 1M NaOH (80 mL) were added dropwise and the resultant solution stirred for 10 min at 0° C. and then for a further 30 min at rt. The reaction mixture was poured into EtOAc (500 mL), washed successively with water, saturated aqueous NH$_4$Cl, saturated aqueous NaHCO$_3$ and brine, dried over Na$_2$SO$_4$ and evaporated to afford a clear colourless oil. Chromatography over silica eluting with 2:3 EtOAc/hexane furnished the title compound as a clear colourless gum (3.3 g, 11.3 mmol, 76%). ESI-MS calcd for C$_{17}$H$_{25}$NO$_3$: 291; found 291 (M).

Intermediate 1c: 1-Boc-4-(azidomethyl)-4-cyclohexylpiperidine

An oven dried, 50-mL, three-necked, round-bottomed flask was purged under nitrogen and then charged with Intermediate 1b(i) (0.400 g, 1.35 mmol), 20 mL of methylene chloride, ZnN$_6$. 2 pyridine (0.828 g, 2.69 mmol), triphenylphosphine (1.42 g, 5.40 mmol), and imidazole (0.368 g, 5.40 mmol). The resulting mixture was then cooled at 0° C. in an ice-water bath and then DEAD (0.85 mL, 5.40 mmol) was added dropwise via syringe. The mixture was stirred at 0° C. for 5 min, warmed to room temperature, and stirred for 23 h. The resulting cloudy mixture was transferred to a 100-mL round-bottomed flask, concentrated, and then purified by column chromatography (1:4 ethyl acetate-hexane) to give the title compound (0.169 g) as a clear oil.

Intermediate 1d: 1-Boc-4-cyclohexyl-4-[(methanesulfonyloxy)methyl]piperidine

To a solution of Intermediate 1b(i) (4.97 g, 16.7 mmol) and Et$_3$N (4.7 mL, 33.4 mmol) in CH$_2$Cl$_2$ at 0° C. was added methanesulfonyl chloride (2.6 mL, 33.4 mmol). The resultant pale yellow solution was allowed to warm to rt and stirred for a further 45 min. Volatiles were removed in vacuo and the residue partitioned between water (150 mL) and EtOAc (150 mL). The aqueous phase was extracted with EtOAc (150 mL) and the combined organic layers washed with brine, dried over Na$_2$SO$_4$ and concentrated to afford the title compound as an off-white solid.

Intermediate 1e: 4-cyclohexyl-4-(isopropylthiomethyl)piperidine trifluoroacetate To a stirred solution of Intermediate 1d (4 mmol) in DMF (25 mL) at rt was added sodium 2-methyl-2-propanethiolate (2 g, 20 mmol). The resultant suspension was stirred at rt for 18 hr then poured into water (75 mL) and extracted with EtOAc (2×75 mL). The combined organic extracts were washed with brine, dried over Na$_2$SO$_4$ and concentrated. Chromatography over silica eluting with 5:95 EtOAc/hexane furnished the N-protected product as a clear colourless oil. The N-Boc-protected sulfide was dissolved in CH$_2$Cl$_2$ (120 mL) and TFA (30 mL) was added. The resultant solution was stirred at rt for 1 hr. Volatiles were removed in vacuo to furnish the title compound as a clear colourless gum (1.34 g, 3.8 mmol). ESI-MS calcd for C$_{15}$H$_{29}$NS: 255; found 297 (M+H+MeCN).

Intermediate 1f: 4-cyclohexyl-4-[(1,2,4-triazol-1-yl)methyl]piperidine trifluoroacetate To a solution of Intermediate 1d (12 mmol) in DMF (75 mL) was added the sodium salt of 1,2,4-triazole (5.5 g, 60 mmol). The resultant suspension was heated at 100–110° C. for 40 hr. After cooling the reaction mixture was poured into water (200 mL) and extracted with EtOAc (2×200 mL). The combined extracts were washed with brine, dried over Na$_2$SO$_4$ and evaporated to afford a clear colorless oil. Chromatography through silica eluting with 2:3 hexanes/ EtOAc furnished the BOC-protected amine as a clear colourless oil. The protected compound was dissolved in CH$_2$Cl$_2$ (180 mL) and TFA (45 mL) was added. The resultant solution was stirred at rt for 1 hr. Volatiles were removed in vacuo to furnish the title compound as a white foam (3.35 g, 9.6 mmol). ESI-MS calcd for C$_{14}$H$_{24}$N$_4$: 248; found 249 (M+H).

Intermediate 1g: 4-cyclohexyl-4-(methoxymethyl) piperidine HCl

To a solution of Intermediate 1d (1.51 gm; 5.07 mmol) in 50 mL of dimethylformamide was added 0.51 gm (12.8 mmol; 60% in mineral oil) of NaH slowly at 0° C. After stirred in ice bath for half hour the mixture was allowed to warmed up to room temperature and 0.91 gm (6.41 mmol) of iodomethane was added and stirred overnight at room temperature. Water (100 mL) was added and the aqueous layer was extracted with ethyl acetate (3×100 mL). The organic layer was washed with 1N HCl and saturated aqueous sodium bicarbonate solution and brine and then dried over magnesium sulfate, filtered and then concentrated. The crude product was purified by flash chromatography (hexane/ethyl acetate 4:1) to give the Boc-protected ether (1.37 gm).

The product was dissolved in ethyl acetate and treated with 5.0 mL of 4.0M HCl in dioxane. The volatiles were removed and provide 0.84 gm of the desired title compound as a colorless solid.

Intermediate 1h: N-methyl-4-cyclohexyl-4-piperidinecarboxamide

To a solution of 1-Boc-4-cyclohexyl-4-piperidinecarboxylic acid (0.934 gm; 3.00 mmol) in 50 mL of dichloromethane was added 6.0 mL (12.0 mmol; 2N in THF) of methylamine, 0.449 gm (3.30 mmol) of HOAt, 1.25 gm (3.30 mmol) of HATU, and stirred at room temperature for 18 h. The reaction mixture was diluted 10 with dichloromethane and washed with 1N HCl and saturated aqueous sodium bicarbonate solution and brine. The organic layer was dried over MgSO$_4$ and evaporated to give an intermediate that was chromatographed on silica gel using hexane-ethyl acetate (2:1) as the eluent to give the coupled product.

The product above was dissolved in 2.0 mL of ethyl acetate and treated with 5.0 mL of 4.0M HCl in dioxane. The volatiles were removed and provide 616.6 nmg of the desired title compound.

Intermediate 1i: N-methyl-N-[(1-Boc-4-cyclohexyl-4-piperidyl)methyl]-methanesulfonamide
Step A: 1-Boc-4-cyclohexyl-4-(aminomethyl)piperidine A 25-mL, round-bottomed flask was charged with Intermediate 1c (0.259 g, 0.803 mmol), 8 mL of THF, and triphenylphosphine (0.32 g, 0.884 mmol). The mixture was stirred at room temperature for 3.5 h and then 0.10 mL of water was added. The resulting reaction mixture was stirred at room temperature for 66 h, and then diluted with ethyl acetate and water. The layers were separated, and the organic phase was washed with water and saturated sodium chloride solution, dried over potassium carbonate, filtered and concentrated. The crude product was purified by column chromatography (gradient elution: 1:4 ethyl acetate-hexane, 9:1 ethyl acetate-methanol, and then 100% methanol) to give the free amine (0.063 g) as a clear oil.

Step B: N-[(1-Boc-4-cyclohexyl-4-piperidyl)methyl]methanesulfonamide

A 15-mL, round-bottomed flask was purged with nitrogen and then charged with the amine from Step A (0.063 g, 0.213 mmol), 1.7 mL of methylene chloride, and triethylamine (0.045 mL, 0.320 mmol). The reaction mixture was cooled at 0° C. in an ice-water bath and then methanesulfonyl chloride (0.018 mL, 0.23 mmol) was added dropwise via syringe. The resulting mixture was stirred at 0° C. for 50 min, warmed to room temperature, and stirred for 16.5 h. The reaction mixture was then diluted with methylene chloride and washed with two portions of 1N HCl solution, saturated sodium bicarbonate solution, water, and saturated sodium chloride solution, dried over sodium sulfate, filtered, and concentrated. The crude product was purified by column chromatography (1:1 methylene chloride-acetone) to give the desired product (0.074 g) as a white solid.

Step C: N-methyl-N-[(1-Boc-4-cyclohexyl-4-piperidyl)methyl]methane sulfonamide

A 10-mL, round-bottomed flask was purged with nitrogen and then charged with a 60% sodium hydride dispersion in mineral oil (0.005 g, 0.125 mmol), and the flask was cooled at 0° C. in an ice-water bath. A solution of the sulfonamide from Step B (0.040 g, 0.107 mmol) in 0.8 mL of dimethylformamide was then added dropwise via syringe. The resulting mixture was stirred at 0° C. for 17 min, warmed to room temperature, and stirred for 10 min. The resulting thick mixture was then charged with methyl iodide (0.033 mL, 0.535 mmol), and the clear mixture was then stirred at room temperature for 5 days. The reaction mixture was then diluted with ethyl acetate and washed with two portions of 1 N HCl solution, saturated sodium bicarbonate solution, water, and saturated sodium chloride solution, dried over sodium sulfate, filtered, and concentrated to give the title compound (0.030 g) as a light yellow oil.

Intermediate 1j(i): 4-phenyl-4-(acetylamino)piperidine HCl salt

Concentrated sulfuric acid (9.25 mL, 174 mmol) was slowly added to a stirred solution of 1-CBZ-4-hydroxy-4-phenylpiperidine (2.52 gm, 8.09 mmol) in acetonitrile (12 mL) at 20° while maintaining reaction temperature at 25°–30° C. using an ice/water bath. Addition was complete after 20 min and the reaction mixture was warmed to r.t., and stirred at r.t. for 1.5 hours. The reaction mixture was then poured into 100 mL ice and neutralized with 5N NaOH (70 mL) and extracted with ethyl acetate (3×, 35 mL). The combined organic layers were washed With brine (50 mL), dried over MgSO$_4$, filtered and concentrated in vacuo to provide 2.5 g (88%) of the N-CBZ protected title compound as a clear, colorless oil.

To a stirred solution of the N-CBZ protected title compound (1.0 gm) in methanol (15 mL) was added conc. HCl (0.3 mL) and Pd(OH)$_2$/C (0.2 gm). The mixture was stirred vigorously under an H$_2$ atmosphere for 2 hr. The reaction mixture was filtered through celite and the solvent removed in vacuo to provide 0.85 gm of the white solid. ESI-MS calc. for $C_{13}H17NO$: 203; Found 204 (M+H).

Intermediate 1i(ii): 1-CBZ-4-phenyl-4-[(N-methyl)acetylamino]piperidine HCl

To a stirred solution of the N-CBZ protected Intermediate 1j(i) (0.59 gm, 1.80 mmol) in tetrahydrofuran (5 mL) at 0° C. was added sodium hydride (86.5 mg, 3.61 mmol) and the mixture stirred 30 min. Iodomethane (512 mg, 3.61 mmol) was added via syringe and the reaction mixture allowed to warm to r.t. while stirring was continued an additional 2 hr. The mixture was concentrated and partitioned between ethyl acetate and 2N HCl. The organic layer was washed with brine, dried over MgSO$_4$, filtered and concentrated in vacuo to afford 413 mg of the the title compound as a clear colorless oil. ESI-MS calc. for $C_{22}H_{32}N_2O_3$: 366; Found 367 (M+H).

Intermediate 1i(iii): 4-cyclohexyl-4-(acetylamino)piperidine HCl

To a stirred solution of Intermediate 1j(i) (2.0 gm, 7.85 mmol) in acetic acid (50 mL) was suspended PtO$_2$-C (1.0 gm). The reaction mixture was stirred under H$_2$ atmosphere at 65° C. for 3 hr, filtered through celite, concentrated, and taken up in minimum amount of methanol. Saturated HCl-EtOAc was added and the mixture was stirred; solvent was removed in vacuo to provide 2.25 gm of the title compound as colorless viscous oil. ESI-MS calc. for $C_{13}H_{25}ClN_2O$: 260; Found 261(M+H).

Intermediate 1ji(iv): 4-(3-phenylpropyl)-4-(acetylamino)piperidine HCl

The title compound was prepared in a similar manner as Intermediate 1j(i). ESI-MS calculated for $C_{16}H_{23}NO$:245; Found 245 (M+H), 263 (M+H+NH$_4$).

Intermediate 1i(v): 4-(cyclohexylmethyl)-4-(acetylamino)piperidine HCl

The title compound was prepared in a similar manner as Intermediate 1j(iii). ESI-MS: 239 (M+H)

Intermediate 1j(vi): 4-cyclohexyl-4-[(N-methyl)acetylamino]piperidine HCl

The title compound was prepared in a similar manner as Intermediate 1j(iii). ESI-MS: 239 (M+H)

Intermediate 1k: ethyl 4-cycloheptyl-4-piperidinecarboxylate trifluoroacetate
Step A: ethyl 1-Boc-4-(1-hydroxycycloheptyl)-4-piperidinecarboxylate To a solution of ethyl N-Boc 4-piperidinecarboxylate (2 g, 7.78 mmole) in tetrahydrofuran (40 ml) was added LDA (5.7 ml, 1.5 M solution in cyclohexane, 8.56 mmole) under nitrogen at −78° C. The mixture was stirred for half an hour. Cycloheptanone (1.01 ml, 8.56 mmole) was added. Then the reaction mixture was stirred at −78° C. for 3 hours and slowly warmed up to room temperature. The mixture was diluted with ethyl acetate (20 ml) and quenched by 6% aqueous acetic acid (30 ml). The organic layer was separated and the aqueous phase was extracted with ethyl acetate. The combined organic extract was washed with water, dried over MgSO$_4$ and concentrated to give a yellow oil (3.2 g), which was purified by column chromatography (hexane:ethyl acetate=4:1) to give colorless oil (2.0 g) of the title compound. ESI-MS calc. for $C_{20}H_{35}NO_5$: 369; Found: 370 (M+H), 411 (M+CH$_3$CN).

Step B: ethyl 4-cycloheptenyl-4-piperidinecarboxylate trifluoroacetate

A mixture of the product of Step A (0.5 g, 1.35 mmole) and trifluoroacetic acid (5 ml) was heated at 60° C. overnight. The reaction mixture was concentrated to give a yellow oil (0.51 g). ESI-MS-calc. for $C_{15}H_{25}NO_2$: 251; Found: 252(M+H), 293 (M+CH$_3$CN).

Step C: ethyl 4-cycloheptyl-4-piperidinecarboxylate trifluoroacetate

To a solution of the product of Step B (0.45 g) in THF was added Pd-C (0.3 g). The mixture was hydrogenated at 55 psi for two days. The catalyst was filtered off and the solvent was removed in vacuo to provide an oil (0.45 g). ESI-MS calc. for $C_{15}H_{27}NO_2$: 253; Found: 254(M+H), 295 (M+CH$_3$CN).

Intermediate 2: 1-(substituted phenylalanyl)-4,4-disubstituted piperidines

Intermediate 2a: ethyl 1-(D-4-chlorophenylalanyl)-4-(4-tetrahydropyranyl)-4-piperidinecarboxylate HCl To a stirred solution of Intermediate 1a(ii) (0.36 gm, 1.30 mmol), N-Boc-D-4-chlorophenylalanine (0.47 gm, 1.56 mmol), HOBt (0.21 gm, 1.56 mmol) and EDC (0.30 gm, 1.56 mmol) in dichloromethane, 10 mL was added NMM (0.50 mL, 4.55 mmol). The mixture was stirred for 16 hr at room temperature and diluted with ethyl acetate and washed with 1N HCl and saturated aqueous sodium bicarbonate solution and brine. The organic layer was dried over anhydrous magnesium sulfate and concentrated to give an intermediate that was chromatographed on silica gel using hexane-ethyl acetate (1:1) as the eluent to give the coupled product.

The product was dissolved in 2.0 mL of ethyl acetate and treated with 5.0 mL of 4.0M HCl in dioxane. The volatiles were removed to provide 0.41 gm of the desired title compound.

Intermediate 2b: ethyl 1-(D-4-chlorophenylalanyl)-4-cyclohexyl-4-[(1,2,4-triazol-1-yl)methyl]piperidine trifluoroacetate To a solution of Intermediate 1f (3.35 g, 9.6 mmol) in CH$_2$Cl$_2$ (200 mL) was added BOC-D-4-chlorophenylalanine (4.9 g, 16.3 mmol), HOBt (2.1 g, 15.4 mmol), EDC (2.9 g, 15.4 mmol) and NMM (4.75 mL, 43.2 mmol). The resultant solution was stirred at rt for 18 hr. The reaction mixture was poured into EtOAc (1L) and washed successively with 0.5M HCl, saturated aqueous NaHCO$_3$ and brine, dried over Na$_2$SO$_4$ and evaporated in vacuo. Chromatography over silica eluting with 1:2 acetone/CH$_2$Cl$_2$ furnished the N-BOC protected amine as a white foam. The coupled product was dissolved in CH$_2$Cl$_2$ (140 mL) and TFA (35 mL) was added. The resultant solution was stirred at rt for 1 hr. Volatiles were removed in vacuo and the residue precipitated from CH$_2$Cl$_2$ with Et$_2$O/hexane to furnish the title compound as a fine white powder (3.2 g, 5.9 mmol, 62%). ESI-MS calcd for $C_{23}H_{32}ClN_5O$: 429; found 430 (M+H).

Intermediates 2c-2mm:

Following the procedure described for Intermediates 2a and/or 2b, and using an appropriate 4,4-disubstituted piperidine and an appropriate phenylalanine derivative, the following compounds were prepared:

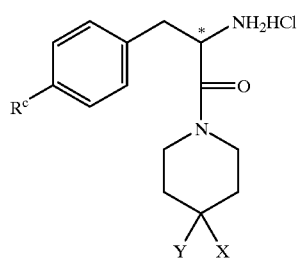

| Interm. | Y | X | R$^c$ | * |
|---|---|---|---|---|
| 2c | Ph | COCH$_2$CH$_3$ | Cl | R |
| 2d | Ph | CO(CH$_2$)$_2$CH$_3$ | Cl | R |
| 2e | Ph | CH$_2$NHSO$_2$CH$_3$ | Cl | R |
| 2f | Ph | N-pyrrolidinecarbonyl | Cl | R |
| 2g | Ph | N-piperidinylcarbonyl | Cl | R |
| 2h | Ph | CO$_2$CH$_2$CH$_3$ | Cl | R |
| 2i | Ph | CON(CH$_3$)$_2$ | Cl | R |
| 2j | Ph | CON(CH$_2$CH$_3$)$_2$ | Cl | R |
| 2k | Ph | CONHCH$_2$CH$_3$ | Cl | R |
| 2l | Ph | COCH$_3$ | Cl | R |
| 2m | Ph | 1-piperazinylcarbonyl | Cl | R |
| 2n | Ph | CN | Cl | R |
| 2o | Ph | CONH-c-propyl | Cl | R |
| 2p | Ph | CH$_2$S—CH(CH$_3$)$_2$ | Cl | R |
| 2q | Ph | CH$_2$-1,2,4-triazol-1-yl | Cl | R |
| 2r | c-hex | CH$_2$OCH$_3$ | Cl | R |
| 2s | c-hex | CO$_2$H | Cl | R |
| 2t | c-hex | CONHCH$_3$ | Cl | R |
| 2u | c-hex | CON(CH$_3$)$_2$ | Cl | R |
| 2v | c-hex | N-pyrrolidinecarbonyl | Cl | R |
| 2w | c-hex | N-piperidinylcarbonyl | Cl | R |
| 2x | c-hex | N-morpholinylcarbonyl | Cl | R |
| 2y | c-hex | CO$_2$CH$_2$CH$_3$ | Cl | S |
| 2z | c-hex | CO$_2$CH$_2$CH$_3$ | OCH$_3$ | R |
| 2aa | c-hex | CO$_2$CH$_2$CH$_3$ | Cl | R |
| 2bb | c-hex | CONH-c-propyl | Cl | R |
| 2cc | c-hex | CONHCH$_2$-c-propyl | Cl | R |
| 2dd | c-hex | CH$_2$S—CH(CH$_3$)$_2$ | Cl | R |
| 2ee | c-hex | CH$_2$N$_3$ | Cl | R |
| 2ff | c-hex | CH$_2$N$_3$ | Cl | S |
| 2gg | c-hex | CH$_2$N(CH$_3$)SO$_2$CH$_3$ | Cl | R |
| 2hh | n-bu | CH$_2$-1,2,4-triazol-1-yl | Cl | R |
| 2ii | c-hep | CO$_2$CH$_2$CH$_3$ | Cl | R |
| 2jj | c-hep | CH$_2$S—CH(CH$_3$)$_2$ | Cl | R |
| 2kk | c-pen | CO$_2$CH$_2$CH$_3$ | Cl | R |
| 2ll | c-hex | CH$_2$-1,2,4-triazol-1-yl | OCH$_3$ | R |
| 2mm | pip* | CONH$_2$ | Cl | R |

*pip = 4-piperidyl

Intermediate 2nn: 1-(N-Boc-D-4-chlorophenylalanyl)-4-acetylamino-4-cyclohexylpiperidine To a stirred solution of Intermediate 1j(iii) (345 mg, 1.21 mmol), Boc-p-Cl-D-Phe-OH (364 mg, 1.21 mmol), PyBrop (570 mg, 1.21 mmol) and DMAP (90 mg, 0.73 mmol) in dichloromethane (2.5 mL) was added DIEA (470 mg, 3.64 mmol). The solution was stirred for 16 hr, concentrated and chromatographed directly (SiO$_2$, 19:1 EtOAc/methanol) to provide 0.59 gm of the title compound as a white solid. ESI-MS calc. for $C_{27}H_{40}ClN_3O_4$: 505; Found 526 (M+H), 406 (M+H-Boc), 526 (M+H+Na).

Intermediate 3: "Acid intermediates"

Intermediates 3a/3b:

[3R(3α,4aα,8aα)]-N-Boc-decahydro-3-isoquinolinecarboxylic acid and

[3R(3α,4aβ,8aβ)]-N-Boc-decahydro-3-isoquinolinecarboxylic acid by resolution using (R)-α-methylbenzylamine and (S)-α-methylbenzylamine

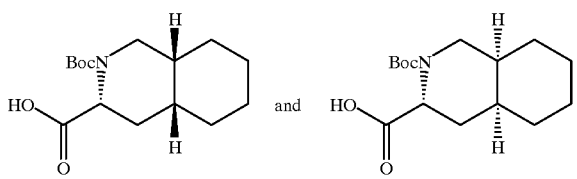

Step A: Preparation of N-Boc-(D)-Tic methyl ester

A 250-mL, round-bottomed flask was charged with commercially available N-Boc-(D)-Tic (10.02 g, 36.1 mmol) and 100 mL of DMF and then purged under nitrogen. Potassium carbonate (5.99 g, 43.3 mmol) was then added followed by the addition of methyl iodide (11.7 mL, 187.7 mmol). The mixture was stirred at room temperature for 22 h and then diluted with $H_2O$ and EtOAc. The aqueous layer was separated and extracted with EtOAc, and the combined organic phases were washed with brine, dried over $Na_2SO_4$, filtered, and concentrated to give a yellow oil. The crude product was purified by column chromatography (3:1 hexane/ethyl acetate) to give N-Boc-(D)-Tic methyl ester (10.52 g) as a clear oil. ESI-MS calcd for $C_{16}H_{21}NO_4$: 291; Found: 292 (M+1).

Step B: Preparation of methyl 3R-N-Boc-3-decahydroisoquinolinecarboxylate

A solution of N-Boc-(D)-Tic methyl ester (10.52 g, 36.1 mmol) and 100 mL of MeOH was charged with 5% Rh/$Al_2O_3$ (5.26 g) and then heated at 60° C. under 40 psi of hydrogen for 36 h. The reaction mixture was filtered through Celite using MeOH and concentrated. The residue was dissolved in EtOAc, dried over $MgSO_4$, filtered, and concentrated to give methyl 3R-N-Boc-3-decahydroisoquinoline-carboxylate (10.73 g) as a clear oil. ESI-MS calcd for $C_{16}H_{27}NO_4$: 297; Found: 298 (M+1).

Step C: Preparation of 3R-N-Boc-3-decahydroisoquinolinecarboxylic acid

Methyl 3R-N-Boc-3-decahydroisoquinoline carboxylate (10.73 g) was dissolved in 120 mL of MeOH and cooled at 0° C. in an ice-$H_2O$ bath. An aqueous 1N NaOH solution (73 mL) was added and then the reaction mixture was stirred at 0° C. for 15 min, warmed to room temperature and stirred overnight. The clear mixture was then concentrated and the resulting cloudy residue was cooled at 0° C. in an ice-$H_2O$ bath. The pH was then adjusted using 1N HCl until pH=2–4 (95 mL), and the aqueous phase was extracted with EtOAc. The combined organic phases were washed with brine, dried over $Na_2SO_4$, filtered, and concentrated to give 3R-N-Boc-3-decahydroisoquinolinecarboxylic acid (10.13 g) as a frothy white oil. ESI-MS calcd for $C_{15}H_{25}NO_4$: 283; Found: 284 (M+1).

Step D: Resolution of 3R-N-Boc-3-decahydroisoquinolinecarboxylic acid using (R)-α-methylbenzylamine 3R-N-Boc-3-decahydroisoquinolinecarboxylic acid (4.67 g, 16.46 mmol) was dissolved in 150 mL of EtOAc and then (R)-α-methylbenzylamine (2.12 mL, 16.46 mmol) was added via syringe. The resulting mixture sat at room temperature under nitrogen overnight, and then the precipitate was filtered and rinsed with EtOAc. The solid was then recrystallized (EtOAc-EtOH) to give [3R(3α,4aα,8aα)]-N-Boc-decahydro-3-isoquinolinecarboxylic acid, (R)-α-methylbenzylamine salt or [3R(3α,4aβ,8aβ)]-N-Boc-decahydro-3-isoquinoline-carboxylic acid, (R)-α-methylbenzylamine salt (2.196 g) as a white solid. The product (0.120 g, 0.297 mmol) was diluted with 10 mL of EtOAc and 1N HCl, stirred for 5 min, and then separated. The organic phase was washed with 1N HCl and brine, dried over $MgSO_4$, filtered and concentrated. The resultant acid is hereinafter referred to as Intermediate 3a.

3R-N-Boc-3-decahydroisoquinolinecarboxylic acid was treated with (S)-α-methylbenzylamine, followed by 1N HCl as described above to provide an acid product hereinafter referred to as Intermediate 3b.

Intermediate 3c:

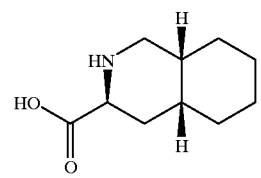

The general procedure for Intermediate 3a/3b was followed using N-Boc-(L)-Tic as the starting material and using (R)-α-methylbenzylamine as the resolving agent to provide [3S(3α,4aα,8aα)]-N-Boc-decahydro-3-isoquinoline-carboxylic acid.

Intermediate 3d:

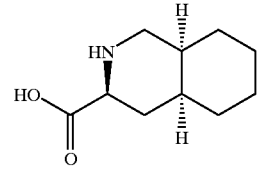

A 25-mL, round-bottomed flask equipped with a reflux condenser was charged with commercially available [3S(3α, 4aβ,8aβ)]-N-tert-butyldecahydro-3-isoquinoline carboxamide (1.0 g, 4.19 mmol) and 10 mL of aqueous 6 N HCl solution. The solution was heated at 80° C. for 23 h and then cooled to 0° C. and diluted with 12 mL of 5 N NaOH solution (pH=13). The aqueous solution was extracted with ethyl acetate and then transferred to a 100-mL, round-bottomed flask and diluted with 25 mL of dioxane. Di-tert-butyl dicarbonate (1.0 g, 4.61 mmol) was then added and the mixture was stirred at room temperature for 23.5 h while occasionally adjusting the pH using 5 N NaOH solution (pH=10). The resulting mixture was diluted with ethyl acetate and water and the layers were separated. The aqueous layer was cooled at 0° C. in an ice-water bath and then 1 N HCl solution was added portionwise until pH=2. The aqueous layer was extracted with three portions of ethyl acetate, and the combined organic phases were washed with saturated sodium chloride solution, dried over sodium sulfate, filtered, and concentrated to give [3S(3α,4aβ,8aβ)]-N-Boc-decahydro-3-isoquinoline-carboxylic acid (0.427 g) as a white solid.

Intermediate 3e:

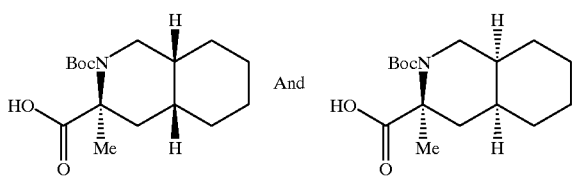

The general procedure described in Steps A and B of Intermediate 3a/3b was followed using N-Boc-α-methyl-(L)-Tic (prepared following standard literature procedures) as the starting material to provide methyl 3S-N-Boc-α-methyl-3-decahydroisoquinolinecarboxylate.

A 25-mL, round-bottomed flask was charged with 3S-N-Boc-α-methyl-3-decahydroisoquinolinecarboxylate (0.863 g, 2.77 mmol) and 9 mL of ethanol. An aqueous 2 N LiOH solution (4.5 mL) was then added and the resulting mixture was placed in a 80° C. oil bath and heated for 48 h. The mixture was then cooled to room temperature and concentrated, and the resulting residue was dissolved in water and cooled at 0° C. in an ice-water bath. The pH was then adjusted using 1 N HCl to pH=2, and the cloudy mixture was diluted with ethyl acetate. The aqueous layer was separated and extracted with two portions of ethyl acetate, and the combined organic phases were washed with saturated sodium chloride solution, dried over sodium sulfate, filtered, and concentrated to give 3S-N-Boc-3-methyl-3-decahydroisoquinolinecarboxylic acid (0.763 g) as a white solid. ESI-MS calcd for $C_{16}H_{27}NO_4$: 297; Found: 298 (M+1).

The following Examples are provided to illustrate the invention, and are not to be construed as limiting the scope of the invention in any manner.

EXAMPLE 1

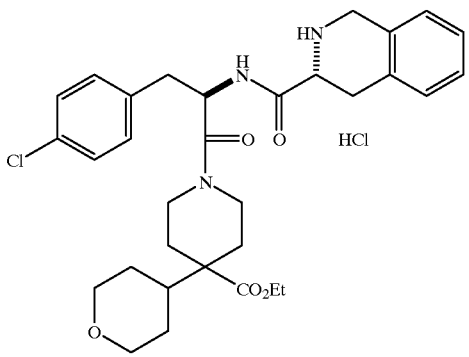

A 25-mL, round-bottomed flask was charged with a solution of Intermediate 2a (112 mg, 0.244 mmol) in 10 mL dichloromethane and then Boc-D-Tic (83.2 mg, 0.300 mmol), NMM (0.10 mL, 0.910 mmol), HOBt. $H_2O$ (40.7 mg, 0.300 mmol), and EDC. HCl (57.5 mg, 0.300 mmol) were added. The resulting mixture was stirred at room temperature for 22 h, and was then diluted with methylene chloride and washed with two portions of 1 N HCl solution, saturated sodium bicarbonate solution, water, and saturated sodium chloride solution, dried over sodium sulfate, filtered, and concentrated. The crude product was purified by flash chromatography (2:1 methylene chloride:acetone) to give the N-Boc protected title compound as a white solid.

A 25-mL, round-bottomed flask was charged with the N-Boc protected title compound and 2.0 mL of methylene chloride. Trifluoroacetic acid (1.0 mL) was then added and the mixture was stirred at room temperature for an hour. The mixture was diluted with toluene and concentrated, and the resulting oil was diluted with toluene again and concentrated. The residue was dissolved in ethyl acetate and washed with 1 N NaOH solution, and the combined organic phases were dried over potassium carbonate, filtered, and concentrated to give a clear oil. The free amine was then dissolved in 1.0 mL of ethyl acetate and 0.5 mL of a 1 N HCl solution in ether was added dropwise via syringe. The mixture was diluted with ether and the precipitate was then filtered to give the title compound (68.1 mg) as a white powder. ESI-MS calcd for $C_{32}H_{40}ClN_3O_5$: 581: Found: 582 (M+1).

EXAMPLE 2

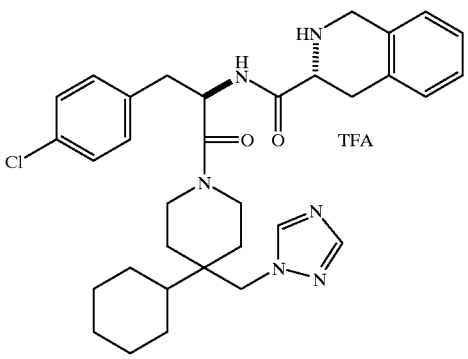

To a solution of Intermediate 2b (1.63 g, 3 mmol) in $CH_2Cl_2$ (60 mL) was added BOC-D-TIC (1.41 g, 5.1 mmol), HOBt (650 mg, 4.8 mmol), EDC (920 mg, 4.8 mmol) and NMM (1.5 mL, 13.5 mmol). The resultant solution was stirred at rt for 18 hr. The reaction mixture was poured into EtOAc (400 mL) and washed successively with 0.5M HCl, saturated aqueous $NaHCO_3$ and brine, dried over $Na_2SO_4$ and evaporated in vacuo. Chromatography over silica eluting with 1:2 acetone/ $CH_2Cl_2$ furnished the title compound as a white foam.

The coupled product was dissolved in $CH_2Cl_2$ (48 mL) and TFA (12 mL) was added. The resultant solution was stirred at rt for 1 hr. Volatiles were removed in vacuo and the residue precipitated from $CH_2Cl_2$ with $Et_2O$/hexane to furnish the title compound as a fine white powder (1.57 g, 2.2 mmol, 74%). ESI-MS calcd for $C_{33}H_{41}ClN_6O_2$ 588; found 589 (M+H).

EXAMPLES 3–54

The general procedures described in Example 1 and Example 2 were followed using an appropriate Intermediate 3 (or a commercially available acid) and an appropriate Intermediate 2 to provide the following compounds:

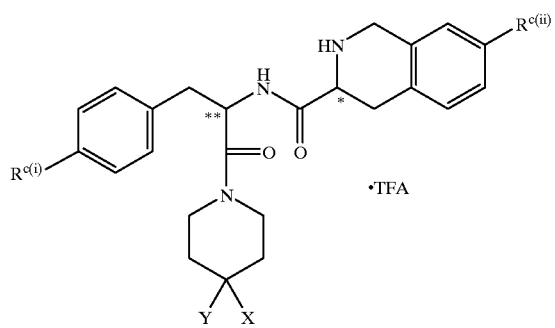

| Ex. | Acid | Interm | Y | X | $R^{c(i)}$ | $R^{c(ii)}$ | EI-MS |
|---|---|---|---|---|---|---|---|
| 3 | L-Tic | 2c | Ph | COCH$_2$CH$_3$ | Cl | H | 558 (M + 1) |
| 4 | L-Tic | 2d | Ph | CO(CH$_2$)$_2$CH$_3$ | Cl | H | 572 (M + 1) |
| 5 | L-Tic(OH) | 2e | Ph | CH$_2$NHSO$_2$CH$_3$ | Cl | OH | 625 (M + 1) |
| 6 | L-Tic | 2f | Ph | CO—N-pyrrolidinyl | Cl | H | 599 (M + 1) |
| 7 | L-Tic | 2g | Ph | CO—N-piperidinyl | Cl | H | 613 (M + 1) |
| 8 | L-Tic | 2p | Ph | CH$_2$S—CH(CH$_3$)$_2$ | Cl | H | 590 (M + 1) |
| 9 | D-Tic | 2p | Ph | CH$_2$S—CH(CH$_3$)$_2$ | Cl | H | 590 (M + 1) |
| 10 | L-Tic | 2q | Ph | CH$_2$-1,2,4-triazol-1-yl | Cl | H | 583 (M + 1) |
| 11 | D-Tic | 2q | Ph | CH$_2$-1,2,4-triazol-1-yl | Cl | H | 583 (M + 1) |
| 12 | L-Tic | 2r | c-hex | CH$_2$OCH$_3$ | Cl | H | 552 (M + 1) |
| 13 | L-Tic | 2s | c-hex | CO$_2$H | Cl | H | 552 (M + 1) |
| 14 | D-Tic(OH) | 2aa | c-hex | CO$_2$CH$_2$CH$_3$ | Cl | OH | 596 (M + 1) |
| 15 | L-Tic | 2y | c-hex | CO$_2$CH$_2$CH$_3$ | Cl | H | 580 (M + 1) |
| 16 | L-Tic | 2z | c-hex | CO$_2$CH$_2$CH$_3$ | OMe | H | 576 (M + 1) |
| 17 | D-Tic | 2dd | c-hex | CH$_2$S—CH(CH$_3$)$_2$ | Cl | H | 596 (M + 1) |
| 18 | L-Tic | 2dd | c-hex | CH$_2$S—CH(CH$_3$)$_2$ | Cl | H | 596 (M + 1) |
| 19 | L-Tic | 2b | c-hex | CH$_2$-1,2,4-triazol-1-yl | Cl | H | 589 (M + 1) |
| 20 | D-Tic | 2ll | c-hex | CH$_2$-1,2,4-triazol-1-yl | OMe | H | 585 (M + 1) |
| 21 | L-Tic | 2ll | c-hex | CH$_2$-1,2,4-triazol-1-yl | OMe | H | 585 (M + 1) |
| 22 | D-Tic | 2hh | n-bu | CH$_2$-1,2,4-triazol-1-yl | Cl | H | 563 (M + 1) |
| 23 | L-Tic | 2hh | n-bu | CH$_2$-1,2,4-triazol-1-yl | Cl | H | 563 (M + 1) |

*stereoconfiguration same as the Tic starting material
**(R) unless otherwise specified Examples 12 and 15 are HCl salts; in Example 15 the α-carbon of the phenylalanyl moiety has the (S) configuration.

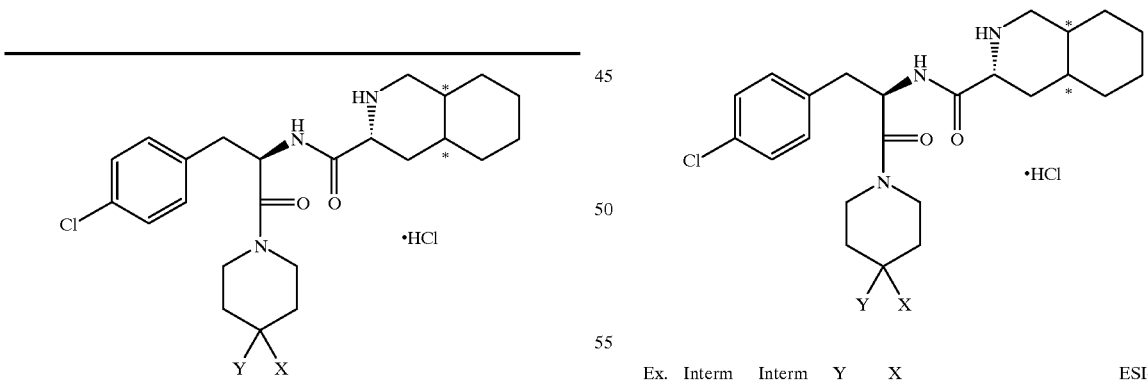

| Ex. | Interm | Interm | Y | X | ESI-MS |
|---|---|---|---|---|---|
| 24 | 3a | 2aa | c-hex | CO$_2$CH$_2$CH$_3$ | 586 (M + 1) |
| 25 | 3b | 2b | c-hex | CH$_2$-1,2,4-triazol-1-yl | 595 (M + 1) |
| 26 | 3a | 2h | Ph | CO$_2$CH$_2$CH$_3$ | 580 (M + 1) |
| 27 | 3b | 2h | Ph | CO$_2$CH$_2$CH$_3$ | 580 (M + 1) |
| 28 | 3b | 2aa | c-hex | CO$_2$CH$_2$CH$_3$ | 586 (M + 1) |
| 29 | 3a | 2i | Ph | C(O)N(CH$_3$)$_2$ | 579 (M + 1) |
| 30 | 3b | 2i | Ph | C(O)N(CH$_3$)$_2$ | 579 (M + 1) |
| 31 | 3a | 2j | Ph | C(O)N(CH$_2$CH$_3$)$_2$ | 607 (M + 1) |
| 32 | 3b | 2j | Ph | C(O)N(CH$_2$CH$_3$)$_2$ | 607 (M + 1) |
| 33 | 3b | 2bb | c-hex | C(O)NH(c-pr) | 597 (M + 1) |
| 34 | 3b | 2u | c-hex | C(O)N(CH$_3$)$_2$ | 585 (M + 1) |
| 35 | 3b | 2cc | c-hex | C(O)NH(CH$_2$-c-pr) | 611 (M + 1) |

*Cis-ring junction, relative stereochemistry unknown

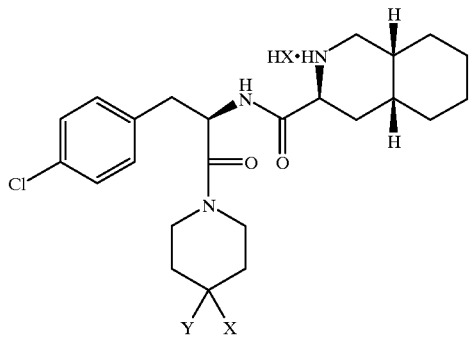

| Ex. | Interm | Salt | R | R¹ | ESI-MS |
|---|---|---|---|---|---|
| 36 | 2aa | TFA | c-hex | $CO_2CH_2CH_3$ | 586 (M + 1) |
| 37 | 2h | TFA | Ph | $CO_2CH_2CH_3$ | 580 (M + 1) |
| 38 | 2k | TFA | Ph | $C(O)NHCH_2CH_3$ | 579 (M + 1) |
| 39 | 2l | TFA | Ph | $C(O)CH_3$ | 550 (M + 1) |
| 40 | 2mm | .2TFA | pip* | $C(O)NH_2$ | 558 (M + 1) |
| 41 | 2m | .2HBr | Ph | C(O)piperazine | 620 (M + 1) |
| 42 | 2i | TFA | Ph | $C(O)N(CH_3)_2$ | 579 (M + 1) |
| 43 | 2j | TFA | Ph | $C(O)N(CH_2CH_3)_2$ | 607 (M + 1) |
| 44 | 2g | TFA | Ph | C(O)piperidine | 619 (M + 1) |
| 45 | 2bb | TFA | c-hex | C(O)NH(c-pr) | 597 (M + 1) |
| 46 | 2u | TFA | c-hex | $C(O)N(CH_3)_2$ | 585 (M + 1) |
| 47 | 2cc | TFA | c-hex | $C(O)NH(CH_2\text{-c-pr})$ | 611 (M + 1) |
| 48 | 2aa | HCl | c-hex | $CO_2CH_2CH_3$ | 582 (M + 1) |
| 49 | 2n | TFA | Ph | CN | 533 (M + 1) |
| 50 | 2e | TFA | PH | $CH_2NHSO_2CH_3$ | 615 (M + 1) |
| 51 | 2b | TFA | c-hex | $CH_2$-1,2,4-triazol-1-yl | 595 (M + 1) |

*pip = 4-piperidyl

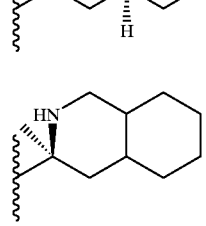

| Ex. | Acid | R | Salt | EI-MS |
|---|---|---|---|---|
| 52 | Interm. 3d | 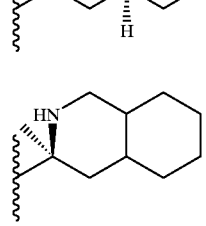 | TFA | 586 (M + 1) |
| 53 | Interm. 3e | | HCl | 600 (M + 1) |

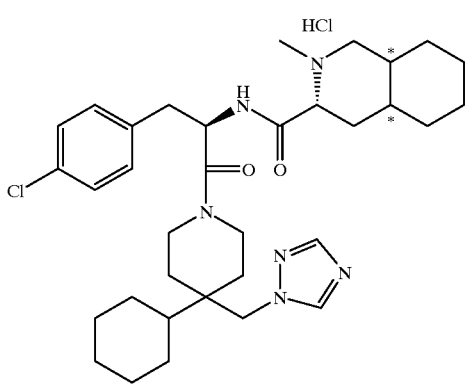

| Ex. | Acid | R | Salt | EI-MS |
|---|---|---|---|---|
| 54 | Boc-(L)-OIC | | TFA | 573 (M + 1) |

EXAMPLE 55

* = cis juncture; absolute configuration not determined

The N-Boc protected compound of Example 25 (0.331 g, 0.477 mmol) was dissolved in 1.20 mL of $CH_2Cl_2$ and 1.20 mL of trifluoroacetic acid, and the mixture was stirred at room temperature for 30 min. The mixture was diluted with toluene and concentrated, and the resulting oil was diluted again with toluene and concentrated to give a white solid (0.340 g). This TFA salt (0.135 g, 0.190 mmol) was dissolved in 0.95 mL of methanol and purged under nitrogen. Sodium acetate (0.078 g, 0.950 mmol) was then added followed by the addition of aqueous formaldehyde (0.068 mL, 0.912 mmol). The resulting mixture was stirred at room temperature for 30 min, and then sodium cyanoborohydride (0.61 mL, 0.608 mmol) was added dropwise via syringe. The reaction mixture was stirred at room temperature overnight and then concentrated. The residue was diluted with ethyl acetate and washed with 1 N NaOH solution and brine, dried over magnesium sulfate, filtered, and concentrated. The crude product was purified by column chromatography (9:1 to 1:1 $CH_2Cl_2$/Acetone) to give a white solid (0.098 g). The amine was dissolved in EtOAc and 1 N HCl in $Et_2O$ (0.19 mL, 0.19 mmol) was added. The mixture was diluted with Et$_2$O and the precipitate was then filtered under nitrogen to give the title compound (0.097 g) as a white solid. ESI-MS calcd for C$_{34}$H$_{49}$N$_6$O$_2$Cl: 608; Found: 609 (M+1).

EXAMPLE 56

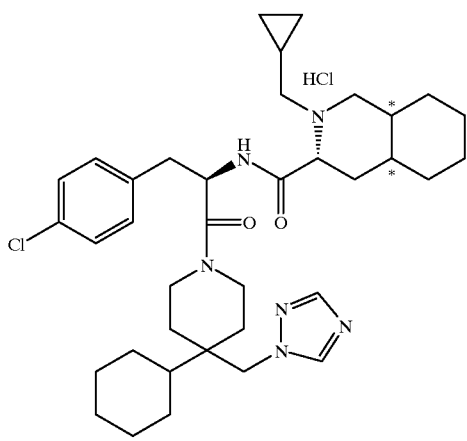

* = cis juncture; absolute stereochemistry not determined

The general procedure described in Example 55 was followed using cyclopropanecarboxaldehyde to provide the title compound. ESI-MS: 649 (M+1).

EXAMPLE 57

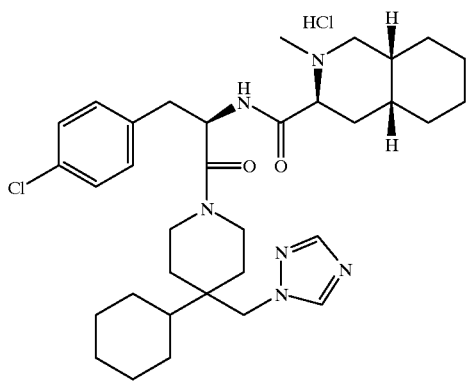

Following the general procedure of Example 55 using the compound of Example 51 (0.060 g, 0.085 mmol), the title compound was obtained. ESI-MS calcd for C$_{34}$H$_{49}$N$_6$O$_2$Cl: 608; found: 609 (M+1).

EXAMPLE 58

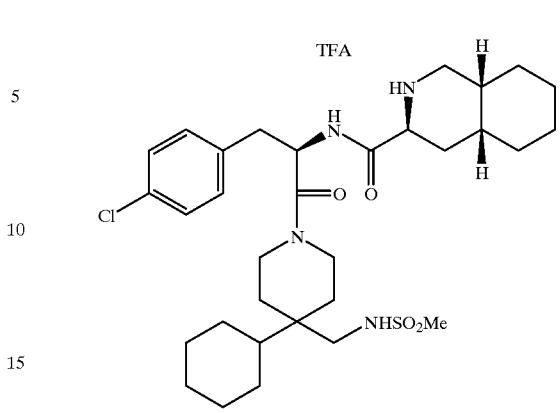

Step A:

To N-Boc-protected Intermediate 2ee (0.105 g, 0.208 mmol) and 0.55 mL of methylene chloride was added trifluoroacetic acid (0.55 mL) and the mixture was stirred at room temperature for 30 min. The mixture was diluted with toluene and concentrated twice to give an oil. The resulting oil was dissolved in 1.2 mL of methylene chloride, and then [3S(3α,4aα,8aα)]-N-Boc-decahydro-3-isoquinoline-carboxylic acid (0.65 g, 0.229 mmol), NMM (0.10 mL, 0.900 mmol), HOBt. H$_2$O (0.031 g, 0.229 mmol), and EDC. HCl (0.044 g, 0.229 mmol) were added. The resulting mixture was stirred at room temperature for 18 h, and then diluted with methylene chloride and washed with two portions of 1 N HCl solution, saturated sodium bicarbonate solution, water, and saturated sodium chloride solution, dried over sodium sulfate, filtered, and concentrated. The crude product was purified by column chromatography (1:1 ethyl acetate-hexane) to give N-Boc coupled azide intermediate (0.114 g) as a white solid.

Step B:

A 25-mL, round-bottomed flask was charged with the product of Step A (0.114 g, 0.170 mmol), 1.7 mL of THF, and triphenylphosphine (0.049 g, 0.187 mmol). The mixture was stirred at room temperature for 2 h and then 0.07 mL of water was added. The resulting reaction mixture was stirred at room temperature for 22.5 h and then diluted with ethyl acetate and water. The layers were separated, and the organic phase was washed with water and saturated sodium chloride solution, dried over potassium carbonate, filtered and concentrated. The crude product was purified by column chromatography (gradient elution: 1:4 ethyl acetate-hexane, 9:1 ethyl acetate-methanol, and then 100% methanol) to give the corresponding N-Boc amine intermediate (0.054 g) as a white solid.

Step C:

A 15-mL, round-bottomed flask was purged with nitrogen and then charged with the amine intermediate of Step B (0.054 g, 0.084 mmol), 0.6 mL of methylene chloride, and triethylamine (0.018 mL, 0.126 mmol). The reaction mixture was cooled at 0° C. in an ice-water bath and then methanesulfonyl chloride (0.007 mL, 0.092 mmol) was added dropwise via syringe. The resulting mixture was stirred at 0° C. for 40 min, warmed to room temperature, and stirred for 18 h. The reaction mixture was then diluted with methylene chloride and washed with two portions of 1 N HCl solution, saturated sodium bicarbonate solution, water, and saturated sodium chloride solution, dried over sodium sulfate, filtered, and concentrated. The crude product was purified by column chromatography (1:1 methylene chloride-acetone) to give N-Boc protected title compound (0.046 g) as a white solid.
Step D:

A 10-mL, round-bottomed flask was charged with N-Boc protected title compound (0.046 g, 0.064 mmol) and 0.20 mL of methylene chloride. Trifluoroacetic acid (0.20 mL) was then added and the mixture was stirred at room temperature for 30 min. The mixture was diluted with toluene and concentrated twice, and then the oil was diluted with ether and concentrated to afford the title compound (0.042 g) as a white powder. ESI-MS calcd for $C_{32}H_{49}N_4O_4SCl$: 620; Found: 621 (M+1).

EXAMPLE 59

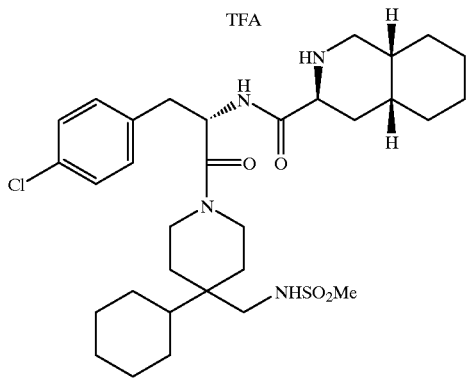

Using Intermediate 2ff, and following the general procedure described in Example 58, the title compound was obtained. ESI-MS calcd for $C_{32}H_{49}N_4O_4SCl$: 620; Found: 621 (M+1).

EXAMPLE 60

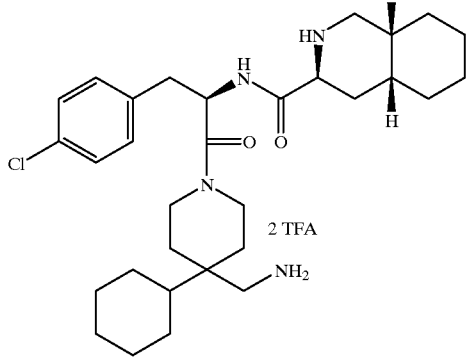

A 10-mL, round-bottomed flask was charged with N-Boc protected title compound (0.014 g, 0.022 mmol) (prepared as illustrated in Example 58, Step B) and 0.10 mL of methylene chloride. Trifluoroacetic acid (0.10 mL) was then added and the mixture was stirred at room temperature for 30 min. The mixture was diluted with toluene and concentrated twice, and then the oil was diluted with ether and concentrated to afford the title compound as a white powder. ESI-MS calcd for $C_{31}H_{47}N_4O_2Cl$: 542; Found: 543 (M+1).

EXAMPLE 61

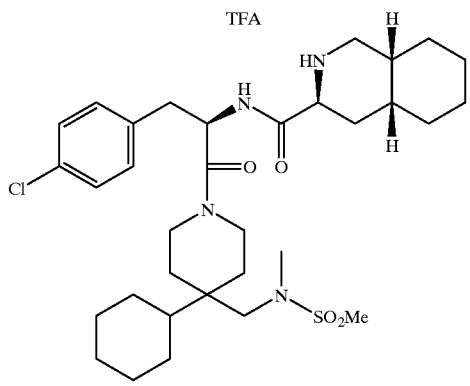

The title compound was prepared from Intermediate 2gg in a similar fashion to the procedure described in Example 58. ESI-MS calcd for $C_{33}H_{51}N_4O_4SCl$: 635; Found: 636 (M+1).

EXAMPLE 62

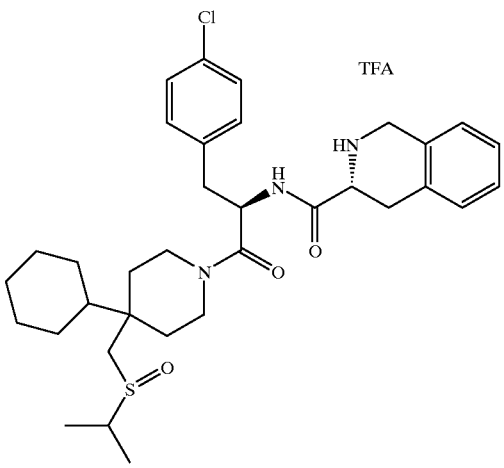

To a stirred solution of compound of Example 17 (128 mg, 0.18 mmol) in EtOH (4.5 mL) was added a solution of $NaIO_4$ (116 mg, 0.54 mmol) in water (4.5 mL) the resultant faintly cloudy solution was stirred at rt for 30 min. Volatiles were removed in vacuo. The residue was extracted with $CH_2Cl_2$ (3×10 mL). The combined extracts were filtered through a short pad of celite and concentrated. Precipitation with $Et_2O$/hexane furnished the title compound as a fine off-white powder (120 mg, 0.17 mmol, 92%). ESI-MS calcd for $C_{34}H_{46}ClN_3O_3S$: 611; found 612 (M+H).

EXAMPLE 63

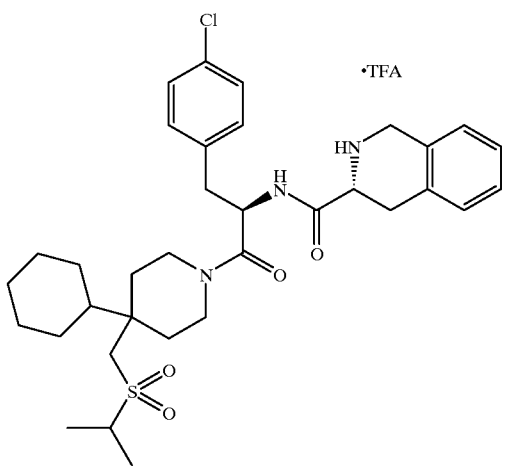

To a stirred solution of compound of Example 17 (75 mg, 0.11 mmol) in EtOH (3.3 mL) was added a solution of oxone (202 mg, 0.33 mmol) in water (3.3 mL) the resultant cloudy solution was stirred at rt for 1.5 hr. Volatiles were removed in vacuo. The residue was extracted with $CH_2Cl_2$ (3×10 mL). The combined extracts were filtered through a short pad of celite and concentrated. Precipitation with $Et_2O$/hexane furnished the title compound as a fine pale pink powder (81 mg, 0.109 mmol, 99%). ESI-MS calcd for $C_{34}H_{46}ClN_3O_4S$: 627; found 628 (M+H).

EXAMPLES 64–69

Following the general procedures of Examples 62 and 63, the following sulfoxides and sulfones were prepared:

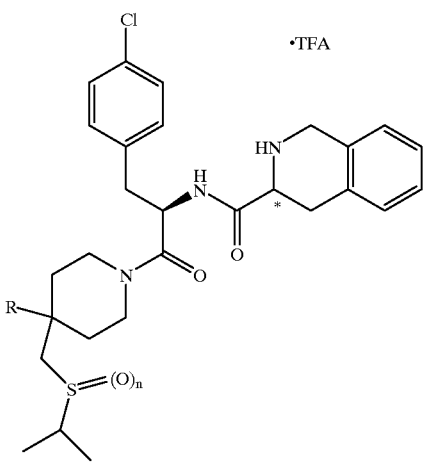

| Ex. | Starting Material | n | R | * | EI-MS |
|---|---|---|---|---|---|
| 64 | Ex. 17 | 1 | c-Hex | S | 612 (M + H) |
| 65 | Ex. 8 | 1 | Ph | S | 606 (M + 1) |
| 66 | Ex. 9 | 1 | Ph | R | 606 (M + 1) |
| 67 | Ex. 17 | 2 | c-Hex | S | 628 (M + 1) |

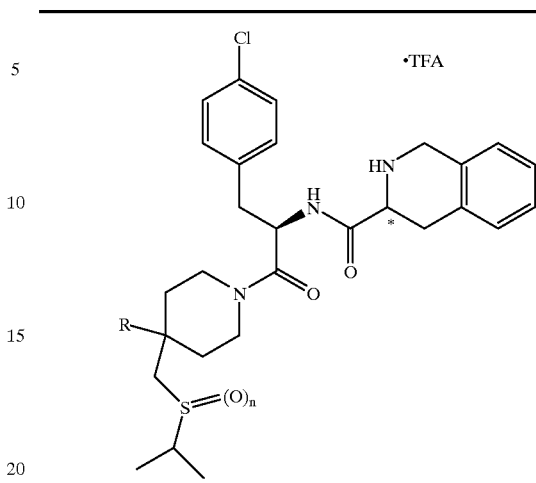

| Ex. | Starting Material | n | R | * | EI-MS |
|---|---|---|---|---|---|
| 68 | Ex. 8 | 2 | Ph | S | 622 (M + 1) |
| 69 | Ex. 9 | 2 | Ph | R | 622 (M + 1) |

EXAMPLE 70

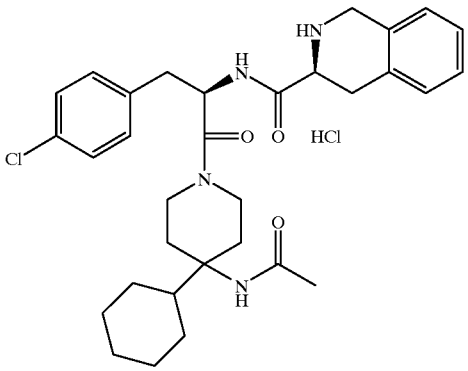

To a stirred solution of Intermediate 1j(iii) (125 mg, 0.44 mmol), N-(4-chloro-D-phenylalanyl) 2-Boc-1,2,3,4-(L)-tetrahydroisoquinolinecarboxamide (202 mg, 0.44 mmol), PyBrop (205 mg, 0.44 mmol) and DMAP (32 mg, 0.26 mmol) in dichloromethane (1.5 mL) was added DIEA (0.23 mL, 1.32 mmol). The solution was stirred for 16 hr, concentrated and chromatographed directly ($SiO_2$,19:1 EtOAc/methanol) to provide 100 mg of N-Boc protected title compound as a white solid. ESI-MS caic. for $C_{37}H_{49}ClN_4O_5$: 665; Found (M+H), 682 (M+NH_4).

To a stirred solution of N-Boc protected title compound (95 mg, 0.14 mmol) in methanol (0.5 mL), HCl-EtOAc was added (5 mL). The reaction was stirred for 20 minutes and the solvent was removed in vacuo to afford 0.86 mg of the title compound. ESI-MS calc. for $C_{32}H_{42}Cl_2N_4O_3$: 600; Found (M+H).

EXAMPLES 71–75

The following compounds were prepared from the appropriate Boc-protected N-(substituted phenylalanyl)-Tic carboxamide in an analogous manner to the one described in Example 70.

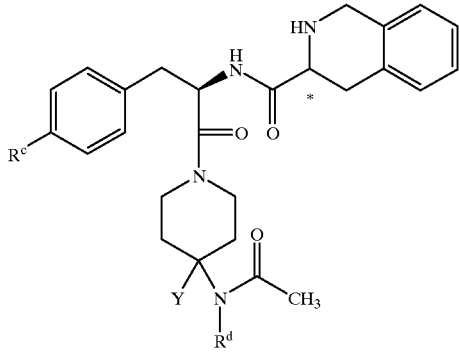

| Ex. | Interm. | * | Y | R^c | R^d | Salt | ESI-MS |
|---|---|---|---|---|---|---|---|
| 71 | 1j (iv) | D-Tic | $(CH_2)_3Ph$ | Cl | H | HCl | 601 (M + H) |
| 72 | 1j (i) | D-Tic | Ph | Cl | H | HCl | 559 (M + H) |
| 73 | 1j (iii) | D-Tic | c-Hex | $CH_3O$ | H | HCl | 561 (M + H) |
|  |  |  |  |  |  |  | 582 (M + H + Na) |
| 74 | 1j (vi) | L-Tic | c-Hex | Cl | $CH_3$ | HCl | 579 (M + H) |
|  |  |  |  |  |  |  | 596 (M + $NH_4$) |
| 75 | 1j (v) | L-Tic | $(CH_2)$-Hex | Cl | H | TFA | 579 (M + H) |
|  |  |  |  |  |  |  | 596 (M + $NH_4$) |

EXAMPLE 76

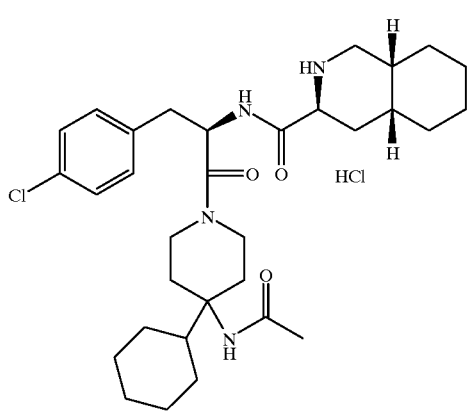

To a stirred solution of Intermediate 2nn (150 mg, 0.34 mmol), 3S-N-Boc-3-decahydroisoquinolinecarboxylic acid (106 mg, 0.34 mmol), PyBrop (158 mg, 0.34 mmol) and DMAP (25 mg, 0.20 mmol) in dichloromethane (1.5 mL) was added DIEA (0.18 mL, 1.02 mmol). The solution was stirred 16 hr, concentrated and the residue purified by preparative HPLC (Cl8, 50–90% acetonitrile/water, 30 min.) to provide 140 mg of N-Boc protected title compound as a white solid. ESI-MS calc. for $C_{37}H_{55}ClN_4O_5$: 670; Found 671(M+H).

To a stirred solution of the N-Boc protected title compound (132 mg, 0.14 mmol) in methanol (0.5 mL), HCl-EtOAc was added (5 mL). The reaction was stirred for 20 minutes and the solvent was removed in vacuo to afford 125 mg of the title compound. ESI-MS calc. for $C_{32}H_{47}ClN_4O_3$: 570; Found 571(M+H)

EXAMPLE 77

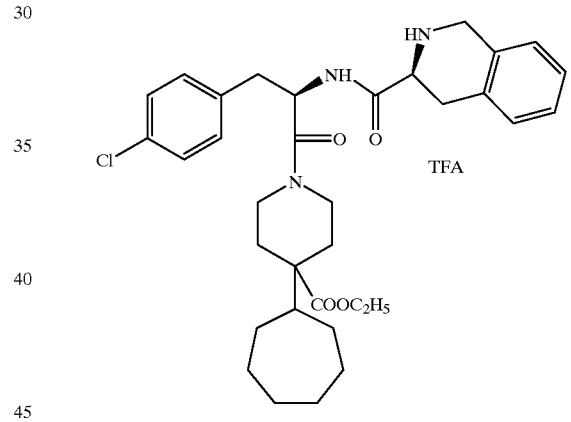

To a solution of Intermediate 2ii (100 mg, 0.182 mmole) in dichloromethane (5 ml) was added 4-methylmorpholine (0.03 ml, 0.273 mmole), Boc-L-Tic (56 mg, 0.200 mmole), HOBt (27 mg, 0.20 mmole) and EDC (52 mg, 0.273 mmole). The reaction mixture was stirred at room temperature for 18 hrs. Water (3 ml) was added and solvent was removed in vacuo. The aqueous phase was extracted with ethyl acetate. The combined organic extract was washed with water, dried over $MgSO_4$ and concentrated to provide yellow oil (120 mg), which was purified by preparative TLC to give N-Boc protected title compound as a white solid (50 mg). ESI-MS calc. for $C_{39}H_{52}ClN_3O_6$: 694; Found: 695 (M+H).

To a solution of the N-Boc protected title compound (50 mg ) in dichloromethane (1.5 ml) was added trifluoroacetic acid (0.5 ml). The reaction mixture was stirred at room temperature for 20 minutes and the solvent was removed in vacuo to afford the title compound (45 mg). ESI-MS calc. for $C_{34}H_{44}ClN_3O_4$: 594; Found: 595 (M+H).

EXAMPLES 78–80

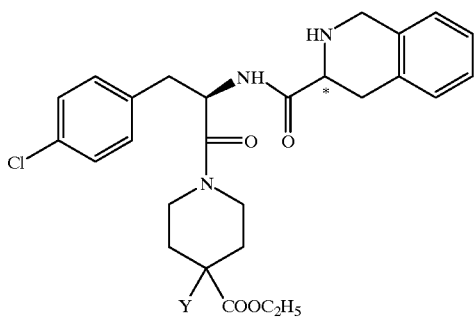

\* stereoconfiguration same as the Tic starting material

The following compounds were prepared from an appropriate Intermediate 2 and Tic in an analogous manner to the one described in Example 77.

| Ex. | Acid | Interm | Y | ESI-MS |
|---|---|---|---|---|
| | D-Tic | 2ii | c-hep | 595 (M + H) |
| | D-Tic | 2kk | c-pen | 566 (M + H) |
| | | | | 588 (M + Na) |
| | L-Tic | 2kk | c-pen | 566 (M + H) |
| | | | | 588 (M + Na) |

EXAMPLE 81

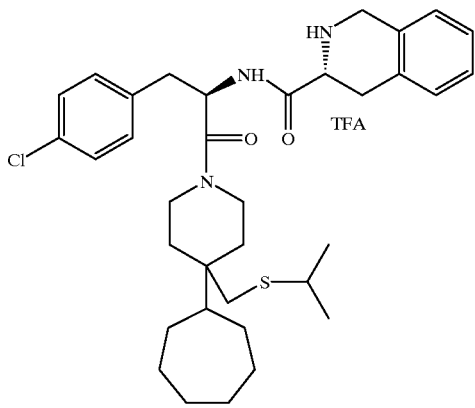

Following the procedure of Example 77, the title compound was prepared using Intermediate 2jj. ESI-MS: 610 (M+H).

EXAMPLES 82–83

Following the procedures described in Examples 62 and 63 and using the compound of Example 81, the following compounds were prepared:

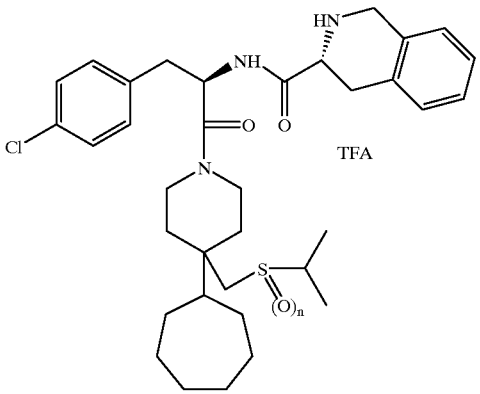

| Ex. | n | ESI-MS |
|---|---|---|
| 82 | 1 | 626 (M + H) |
| 83 | 2 | 642 (M + H) |

EXAMPLE 84

Example 2 is representative of the compounds of the present invention which are selective agonists of the human MC-4R and active in the models of penile erection. The in vitro pharmacological properties of Example 2 were evaluated. $IC_{50}$'s were determined in a competition binding assay with $^{125}I$-NDP-alpha-MSH as ligand using crude membranes prepared from cell lines expressing the appropriate MC-R. Functional $EC_{50}$'s were determined by application of compound to intact cells followed by direct measurement of cAMP as described in the Biological Assays section above. In the Binding Assay, Example 2 was greater than 2200-fold selective for the human MC-4R over the human MC-1R receptor; greater than 10,000-fold selective for the human MC-4R over the human MC-2R receptor; greater than 580-fold selective for the human MC-4R over the human MC-3R receptor; and greater than 250-fold selective for the human MC-4R over the human MC-5R receptor (Table 1).

TABLE 1.

| In vitro pharmacology of Example 2* | |
|---|---|
| Binding Activity $IC_{50}$ (nM) | Example 2 Human[1] |
| MC-1R | 2100 |
| MC-2R | >10000 |
| MC-3R | 540 |
| MC-4R | 0.92 |
| MC-5R | 230 |
| Functional Activity $EC_{50}$ (nM) | Example 2 Human[1] |
| MC-1R | 1300, 84% |
| MC-2R | 0% @ 10 μM |
| MC-3R | 1200, 29% |
| MC-4R | 2.1, 96% |
| MC-5R | 530, 58% |

\*$IC_{50}$ and $EC_{50}$ values are the average of at least 3 determinations, and have been rounded to 2 significant figures.

Example 2 was effective in significantly increasing the number of erections in a conscious rat model of reflexogenic erections (Table 2) when administered either by the intravenous (IV) route or by the oral (PO) route. In this non-random crossover model, rats were placed in the supine position with the preputial sheath retracted to initiate a reflex arc. The number of erections was counted in the 15 minute period following the first erection. Both apomorphine and sildenafil citrate were effective in this model.

TABLE 2.

Effects of Example 2 on penile erections in Rats

| Dose and Route of Example 2 (mg/kg) | Minutes after Dosing Rats Placed Supine | % Increase from Vehicle or Baseline | Number of Rats |
| --- | --- | --- | --- |
| 0.3 IV | 60 | 15* | 6 |
| 1.0 IV | 0, 60 | 31*, 35* | 5, 6 |
| 5.0 IV | 60 | 50** | 6 |
| 10 IV | 0, 60 | 45**, 38** | 6, 6 |
| 20 PO | 60 | 24** | 6 |
| 20 μG ICV | 0 | 41* | 6 |

*P = 0.05
**P = 0.01

EXAMPLE 85

As a specific embodiment of an oral composition of a composition of the present invention, 5 mg of Example 2 is formulated with sufficient finely divided lactose to provide a total amount of 580 to 590 mg to fill a size O hard gelatin capsule.

EXAMPLE 86

As another specific embodiment of an oral composition of a compound of the present invention, 2.5 mg of Example 2 is formulated with sufficient finely divided lactose to provide a total amount of 580 to 590 mg to fill a size O hard gelatin capsule.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the patient being treated for erectile dysfunction. Likewise, the specific pharmacological responses observed may vary according to and depending upon the particular active compound or combination selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound having the formula I:

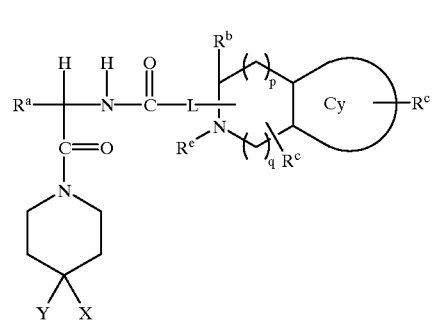

or a pharmaceutically acceptable salt thereof; wherein
Cy is
  (1) aryl,
  (2) 5- or 6-membered heteroaryl,
  (3) 5- or 6-membered heterocyclyl, or
  (4) 5- to 7-membered carbocyclyl;
L is $(CR^b R^b)_m$;
m is 0, 1 or 2;
n is 0, 1, 2, or 3;
p is 0, 1 or 2;
q is 0, 1 or 2;
$R^a$ is
  (1) hydrogen,
  (2) $C_{1-8}$ alkyl,
  (3) $(CHR^b)_n$—$C_{3-7}$cycloalkyl,
  (4) $(CHR^b)_n$aryl,
  (5) $(CHR^b)_n$heteroaryl, or
  (6) $(CHR^b)_n$—$O(CHR^b)$aryl;
  in which alkyl is optionally substituted with from 1 to 3 groups independently selected from Rg; aryl, heteroaryl and cycloalkyl are optionally substituted with 1 to 3 groups independently selected from $R^f$;
$R^b$ is
  (1) hydrogen,
  (2) $C_{1-8}$alkyl,
  (3) $(CH_2)_n C_{3-7}$cycloalkyl, or
  (4) $(CH_2)_n$-aryl;
$R^c$ is
  (1) hydrogen or
  (2) a group selected from $R^f$;
$R^d$ is
  (1) hydrogen,
  (2) $C_{1-8}$alkyl,
  (3) $(CH_2)_n$-aryl,
  (4) $(CH_2)_n C_{3-7}$cycloalkyl or
  (5) $(CH_2)_n$-heteroaryl;
  wherein alkyl and cycloalkyl are optionally substituted with 1 to 3 groups selected from Rg; and cycloalkyl, aryl and heteroaryl are optionally substituted with 1 to 3 groups selected from $R^f$; or two $R^d$ groups together with the atoms to which they are attached form a 5- or 6-membered ring optionally containing an additional heteroatom selected from O, S, and $NR^b$;
$R^e$ is
  (1) a group selected from $R^d$,
  (2) $COR^d$,
  (3) $SO_2R^d$, or (4) COC($R^b$)($R^b$)N($R^d$)($R^d$);
$R^f$ is
  (1) a group selected from Rg, or
  (2) $C_{1-8}$ alkyl;
Rg is
  (1) $(CH_2)_n$-aryl,
  (2) $(CH_2)_nC_{3-7}$cycloalkyl,
  (3) $(CH_2)_n$-heteroaryl,
  (4) halo,
  (5) $OR^b$,
  (6) $NHSO_2R^b$,
  (7) $N(R^b)_2$,
  (8) C≡N,
  (9) $CO_2R^b$,
  (10) $C(R^b)(R^b)N(R^b)_2$,
  (11) $NO_2$,
  (12) $SO_2N(R^b)_2$,
  (13) $S(O)_mR^b$,
  (14) $CF_3$, or
  (15) $OCF_3$;
X is
  (1) hydrogen,
  (2) $C_{1-8}$alkyl,
  (3) $(CH_2)_nC_{3-8}$cycloalkyl,
  (4) $(CH_2)_n$aryl,
  (5) $(CH_2)_n$heteroaryl,
  (6) $(CH_2)_n$heterocyclyl,
  (7) C≡N,
  (8) $(CH_2)_nCON(R^dR^d)$,
  (9) $(CH_2)_nC(O)OR^d$,
  (10) $(CH_2)_nNR^dC(O)R^d$,
  (11) $(CH_2)_nNR^dC(O)OR^d$,
  (12) $(CH_2)_nNR^dC(O)N(R^d)_2$,
  (13) $(CH_2)_nNR^dSO_2R^d$,
  (14) $(CH_2)_nS(O)mR^d$,
  (15) $(CH_2)_nSO_2N(R^d)(R^d)$,
  (16) $(CH_2)_nOR^d$,
  (17) $(CH_2)_nOC(O)R^d$,
  (18) $(CH_2)_nOC(O)OR^d$,
  (19) $(CH_2)_nOC(O)N(R^d)_2$,
  (20) $(CH_2)_nN(R^d)(R^d)$,
  (21) $(CH_2)_nNR^dSO_2N(R^d)(R^d)$;
  wherein the cycloalkyl, aryl and heteroaryl groups are optionally substituted with 1 to 3 groups selected from $R^f$; the heterocyclyl group is optionally substituted with 1 to 3 groups selected from $R^f$ and oxo; and the $(CH_2)_n$ and alkyl groups are optionally substituted with 1 to 3 groups selected from Rg; and
Y is
  (1) hydrogen,
  (2) $C_{1-8}$alkyl,
  (3) $(CH_2)_nC_{3-8}$cycloalkyl,
  (4) $(CH_2)_n$aryl,
  (5) $(CH_2)_n$heterocyclyl, or
  (6) $(CH_2)_n$heteroaryl;
  wherein the cycloalkyl, aryl and heteroaryl groups are optionally substituted with 1 to 3 groups selected from $R^f$; heterocyclyl group is optionally substituted with 1 to 3 groups selected from Rf and oxo; and the alkyl group is optionally substituted with 1 to 3 groups selected from Rg;
with the proviso that X and Y are not both hydrogen.

2. The compound of claim 1 wherein Cy is selected from the group consisting of benzene, pyridine, pyrazine, piperidine, imidazole and cyclohexane.

3. The compound of claim 2 wherein Cy is benzene, pyrazine, or cyclohexane.

4. The compound of claim 1 wherein L is $(CH_2)_m$ wherein m is 0, 1 or 2.

5. The compound of claim 1 wherein $R^a$ is $CH(R^b)$-arl, $CH(R^b)$—$OCH_2$aryl, or $CH(R^b)$-heteroaryl wherein aryl or heteroaryl is optionally substituted with one or two Rg groups.

6. The compound of claim 5 wherein $R^a$ is benzyl optionally substituted with one or two groups selected from halogen, $C_{1-4}$ alkyl, $C_{1-4}$ alkoxy, $CF_3$, and $OCF_3$.

7. The compound of claim 6 wherein $R^a$ is 4-chlorobenzyl or 4-fluorobenzyl.

8. The compound of claim 1 wherein $R^b$ attached to the bicyclic ring of formula I is H or $CH_3$.

9. The compound of claim 1 wherein X is $C_{1-8}$alkyl, $(CH_2)_n$—$C_{3-7}$cycloalkyl, $(CH_2)_n$-aryl, $(CH_2)_n$-heteroaryl, $(CH_2)_n$-heterocyclyl, $(CH_2)_nC(O)N(R^d)(R^d)$, $(CH_2)_nC(O)OR^d$, $(CH_2)_nOR^d$, $(CH_2)_nNHC(O)Rd$, $(CH_2)_nN(R^d)SO_2R^d$, or $(CH_2)_nSR^d$, wherein the cycloalkyl, aryl and heteroaryl groups are optionally substituted with 1 to 3 groups selected from $R^f$; heterocyclyl is optionally substituted with 1 to 3 groups selected from $R^f$ and oxo; and the $(CH_2)_n$ and alkyl groups are optionally substituted with 1 to 3 groups selected from $R^b$, halo, $S(O)mR^b$, $N(Rb)_2$, and $OR^b$.

10. The compound of claim 9 wherein X is $CH_2$-heteroaryl, $CH_2$-heterocyclyl, $NHC(O)R^d$, $C(O)OR^d$, $CH_2N(R^d)SO_2R^d$ or $C(O)N(R^d)(R^d)$, wherein heteroaryl is optionally substituted with 1 to 3 group selected from $R^f$; heterocyclyl is optionally substituted with 1 to 3 groups selected from $R^f$ and oxo; and wherein $R^d$ is each independently selected from H and $C_{1-6}$ alkyl optionally substituted with $OR^b$, $SR^b$, or $N(R^b)_2$, or 2 $R^d$ groups together with the nitrogen to which they are attached form a 5- or 6-membered ring optionally having an additional heteroatom selected from O, S and $NR^b$.

11. The compound of claim 10 wherein heteroaryl is selected from pyridyl, pyrazinyl, pyrimidinyl, triazolyl, tetrazolyl, thiadiazolyl, oxadiazolyl, pyrazolyl, and imidazolyl.

12. The compound of claim 1 wherein Y is $(CH_2)_nC_{3-7}$ cycloalkyl, $(CH_2)_n$-aryl, $(CH_2)_n$-heterocyclyl or $(CH_2)_n$-heteroaryl wherein cycloalkyl, aryl and heteroaryl are optionally substituted with 1 to 3 groups selected from $R^f$, and heterocyclyl is optionally substituted with 1 to 3 groups selected from $R^f$ and oxo.

13. The compound of claim 12 wherein Y is cyclohexyl, cycloheptyl, cyclopentyl, cyclobutylmethyl, hexyl, tetrahydropyranyl, phenyl, naphthyl, pyridyl, thienyl or furanyl.

14. The compound of claim 13 wherein Y is cyclohexyl, tetrahydropyranyl, or phenyl.

15. The compound of claim 1 of formula Ia:

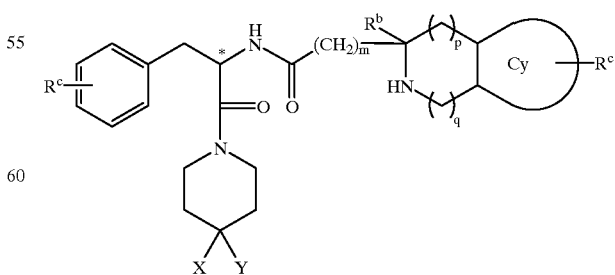

Ia or a pharmaceutically acceptable salt thereof; wherein
Cy is (1) phenyl,
(2) pyridyl,
(3) piperidinyl,
(4) imidazolyl,
(5) cyclohexyl, or
(6) pyrazinyl;

m is 0 or 1;
n is 0 or 1;
p is 0 or 1;
q is 1 or 2;

$R^b$ is
(1) hydrogen,
(2) $C_{1-8}$alkyl, or
(3) $C_{3-6}$cycloalkyl;

$R^c$ is
(1) hydrogen,
(2) halo,
(3) $C_{1-8}$alkyl, or
(4) $C_{3-6}$cycloalkyl,
(5) $OR^b$,
(6) $CF_3$,
(7) $OCF_3$,
(6) $S(O)_m R^b$, or
(7) $N(R^b)(R^b)$;

$R^d$ is
(1) hydrogen,
(2) $C_{1-5}$alkyl, optionally substituted with $OR^b$, $NR^bR^b$, or $SR^b$,
(3) aryl,
(4) heteroaryl,
(5) $C_{5-6}$cycloalkyl, or
two $R^d$ together with the atoms to which they are attached form a 5- or 6-membered ring optionally containing an additional heteroatom selected from O, S and $NR^b$;

X is
(1) hydrogen,
(2) $C(O)OR^d$,
(3) $C(O)N(R^d)(R^d)$,
(4) $NHC(O)R^d$,
(5) $NHC(O)NHR^d$,
(6) $NHC(O)OR^d$,
(7) $NHSO_2R^d$,
(8) $OC(O)R^d$,
(9) $C_{1-6}$alkyl,
(10) $CH_2$—$C_{3-7}$cycloalkyl,
(11) $(CH_2)_n$-aryl, optionally substituted with 1 to 3 groups selected from halogen, $C(O)OR^b$, and tetrazole,
(12) $(CH_2)_n$-heteroaryl, optionally substituted with $C_{1-3}$alkyl, $N(R^b)(R^b)$ or $OR^b$,
(13) $(CH_2)_n$-heterocyclyl optionally substituted with 1 to 3 groups selected from $C_{1-3}$ alkyl and oxo,
(14) $CH_2$—$OR^d$,
(15) $(CH_2)_nS(O)_mR^d$,
(16) $(CH_2)_nN(Rd)SO_2R^d$,
(17) $(CH_2)_nC(O)R^d$, or
(18) S-heteroaryl;

Y is
(1) hydrogen,
(2) $C_{1-8}$alkyl,
(3) $C_{3-7}$cycloalkyl,
(4) $(CH_2)_n$aryl,
(5) $(CH_2)_n$heteroaryl, or
(6) $(CH_2)_n$heterocyclyl;
wherein the cycloalkyl, aryl, heteroaryl, or heterocyclyl group is optionally substituted with one or two halo groups;
with the proviso that X and Y are not both hydrogen.

16. The compound of claim 15 wherein the carbon atom marked with * has the R configuration.

17. The compound of claim 15 wherein X is selected from the group consisting of:

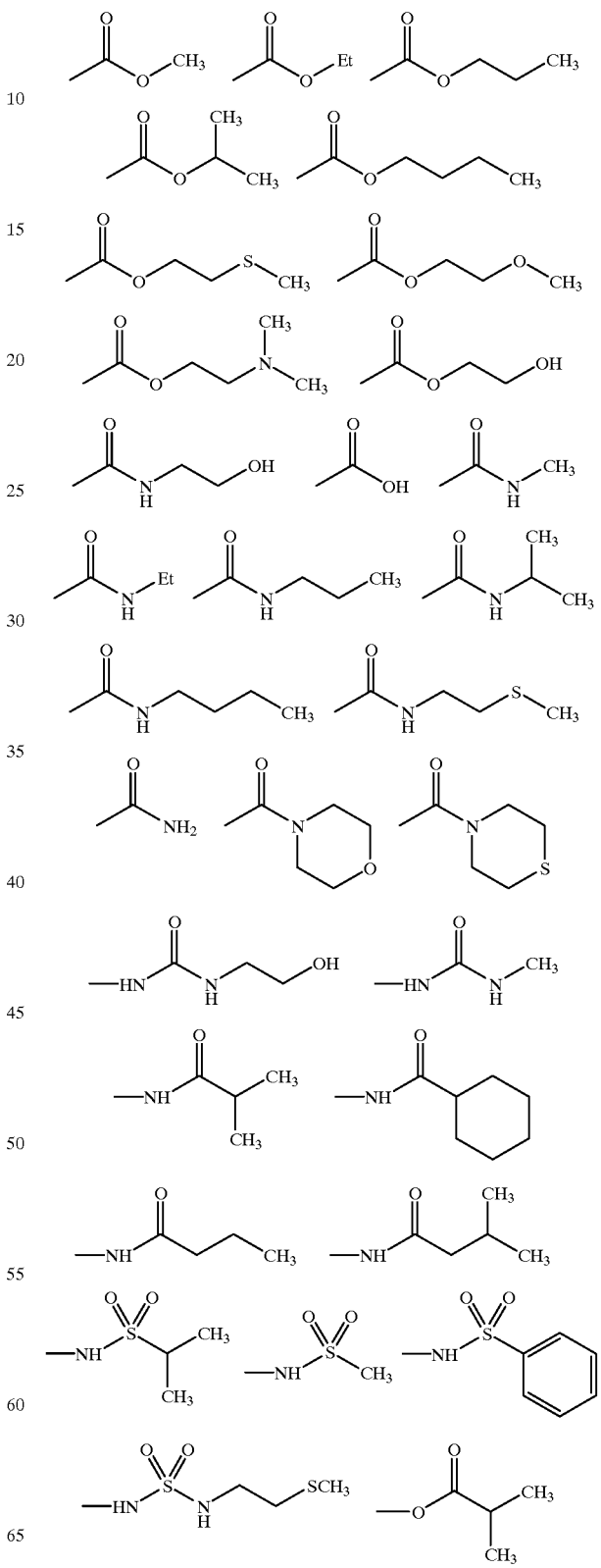

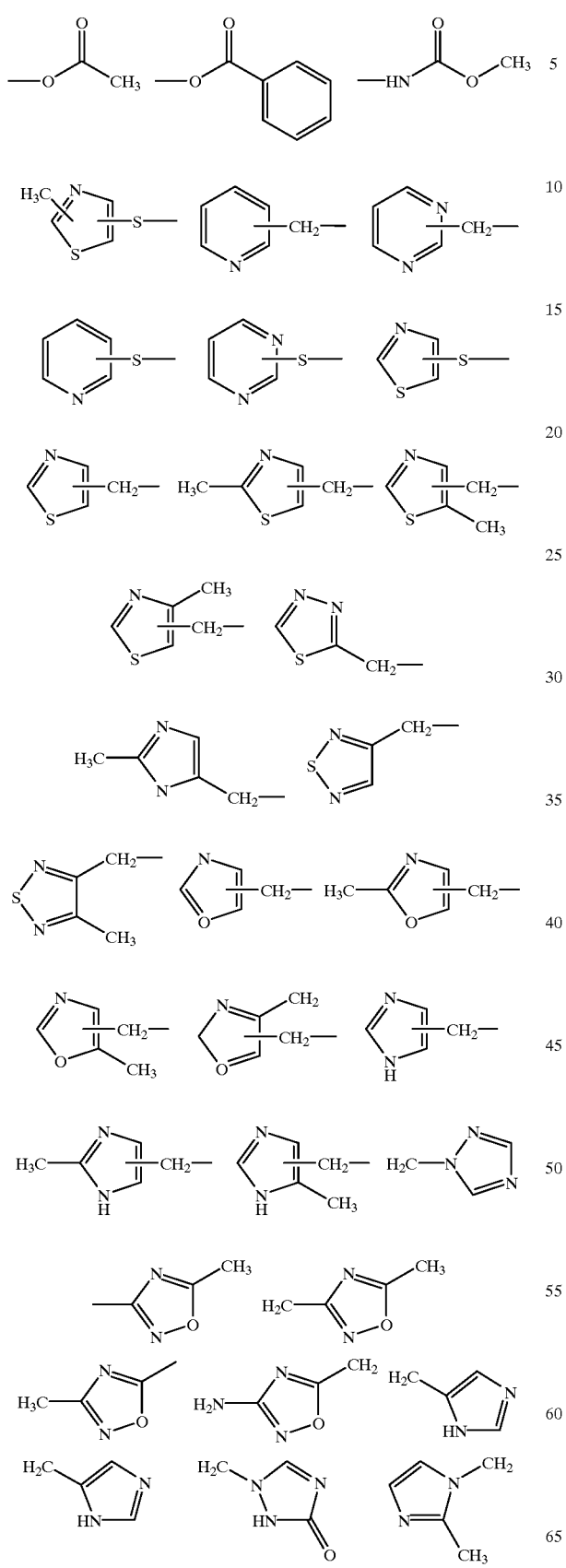
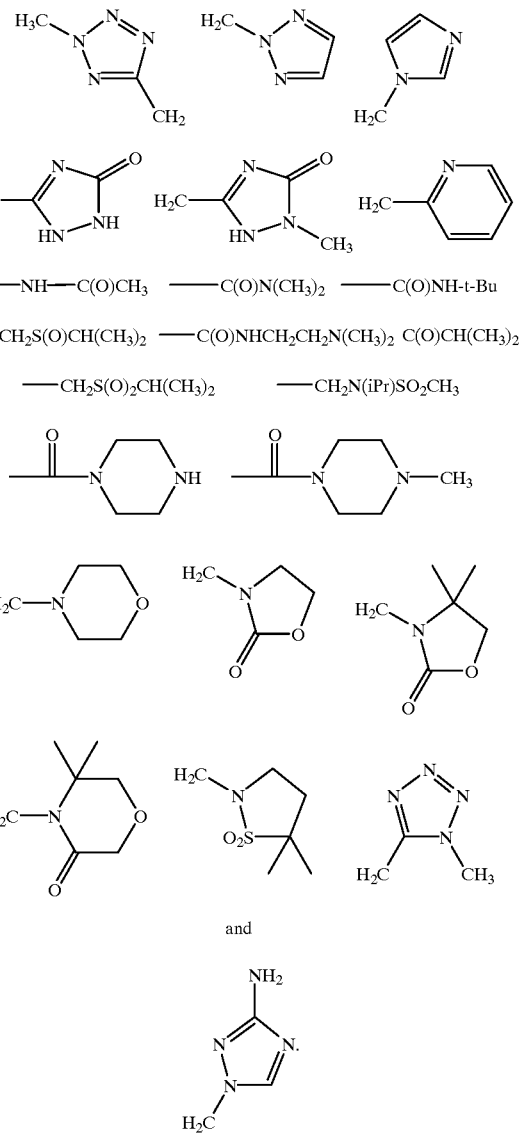
18. The compound of claim 15 selected from the group consisting of:
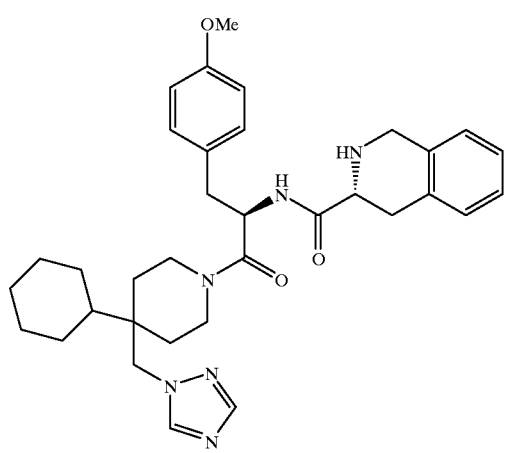

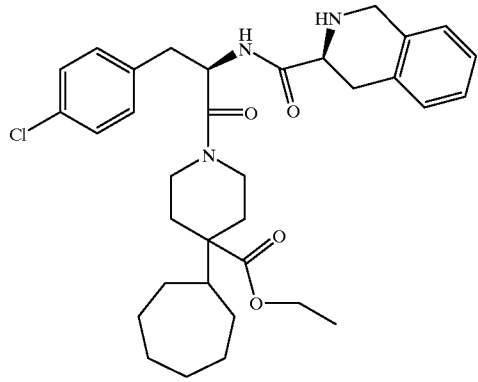
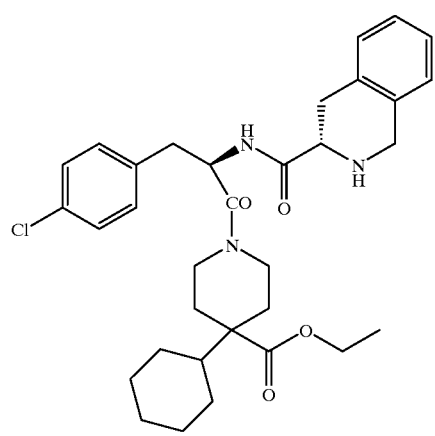
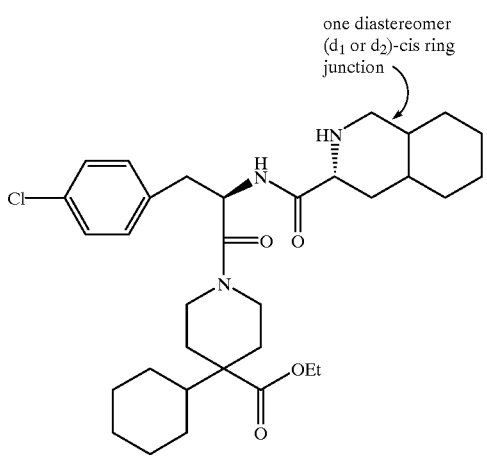
one diastereomer (d₁ or d₂)-cis ring junction
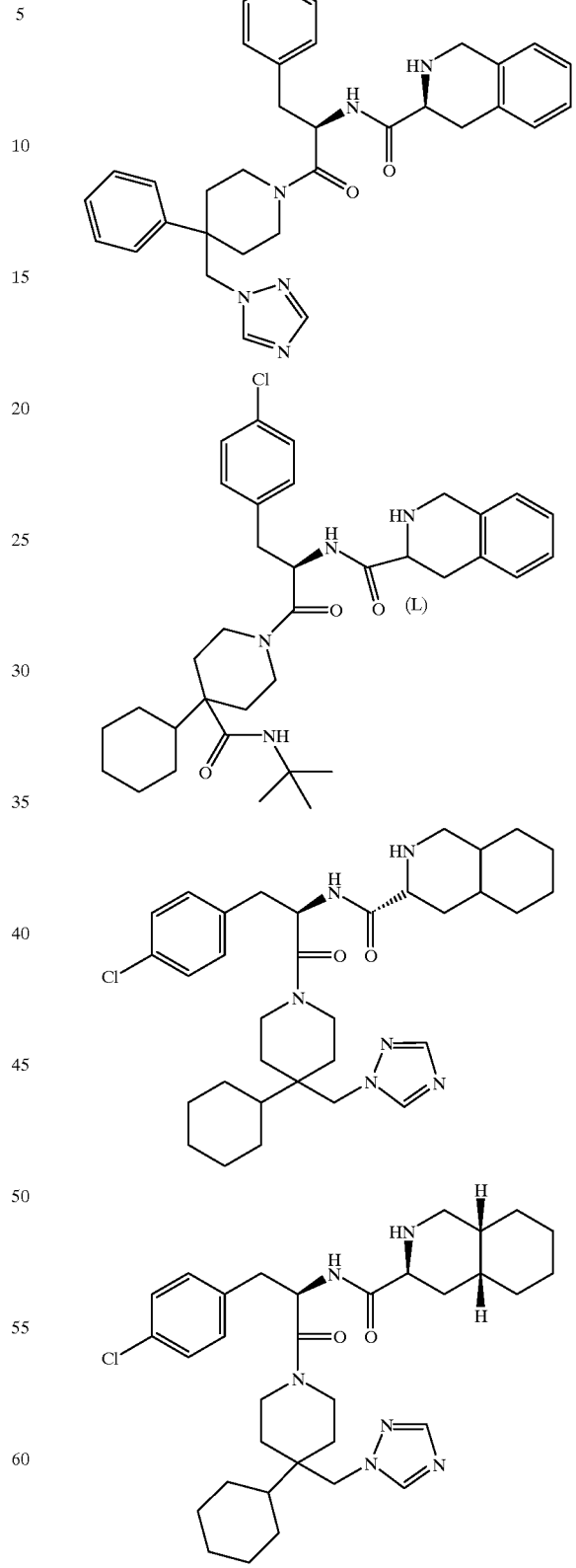

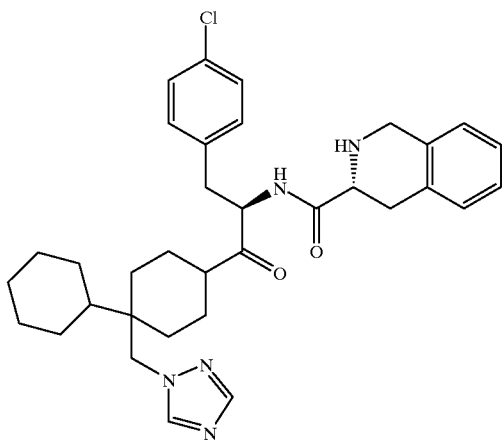
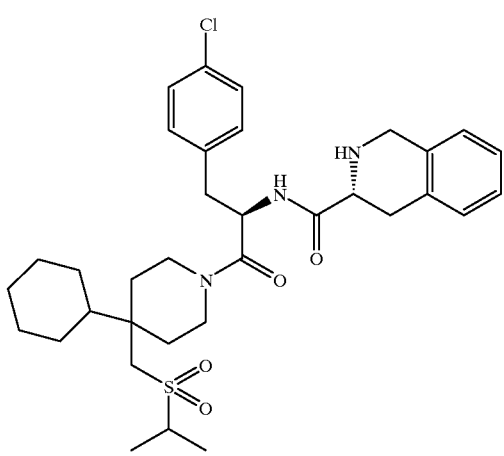
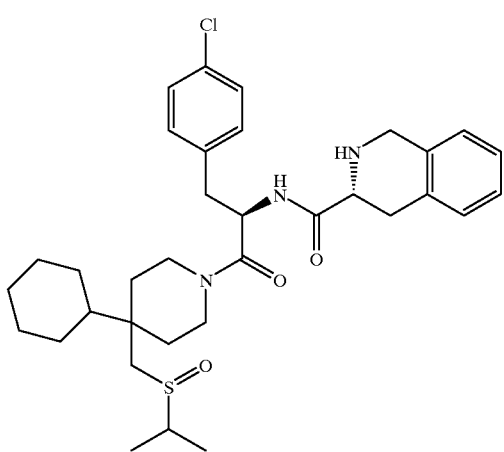
d₁+d₂ diastereomeric at sulfur
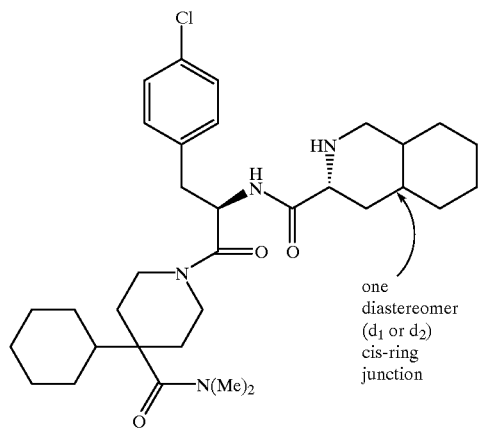
one diastereomer (d₁ or d₂) cis-ring junction
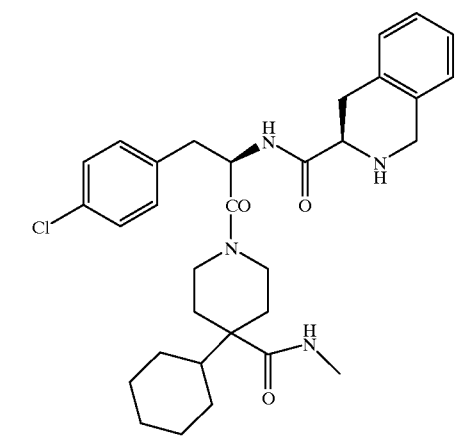
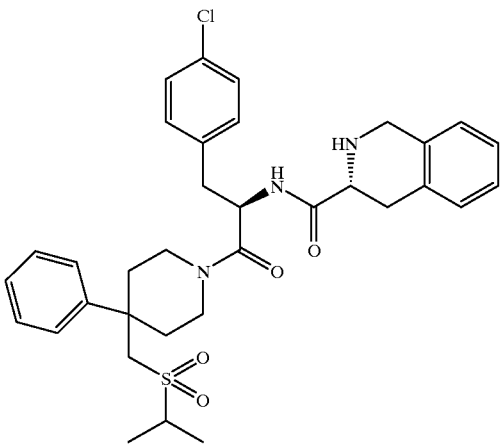

85
-continued
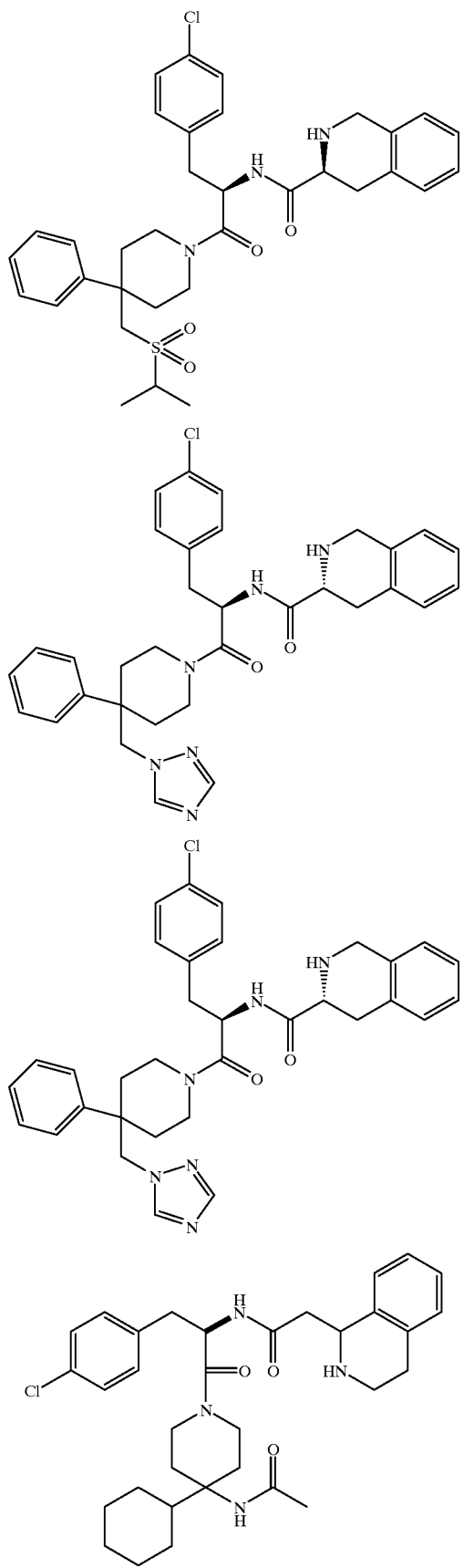
86
-continued
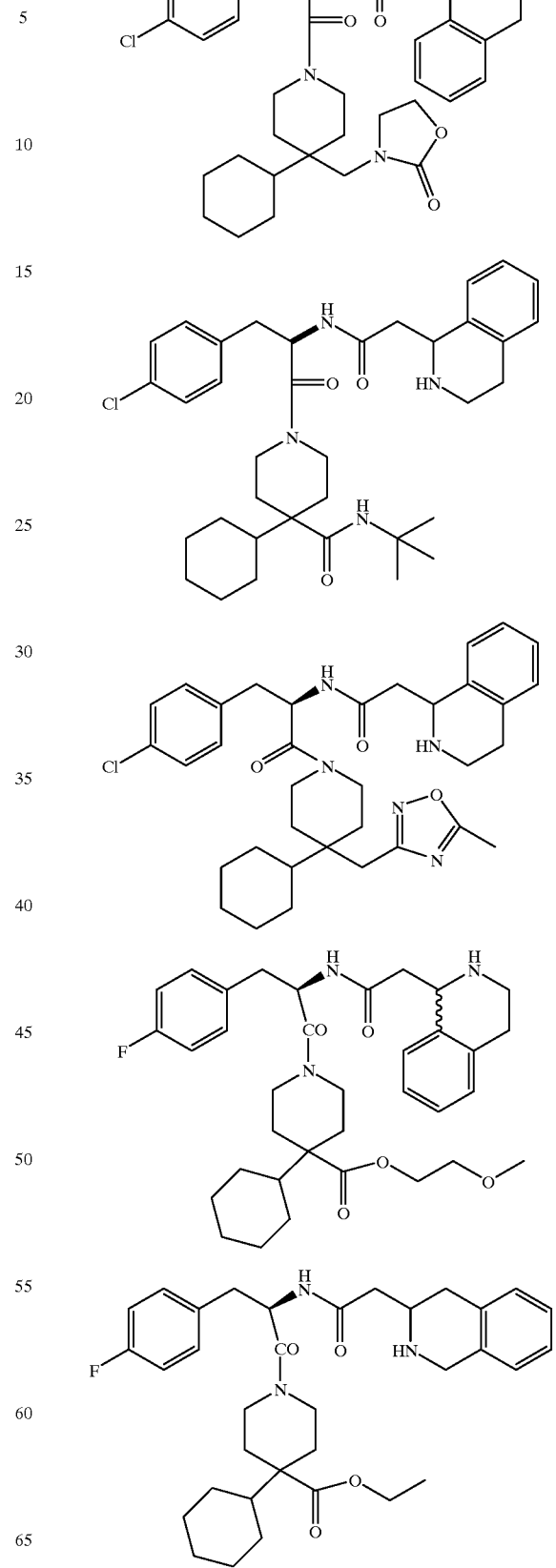

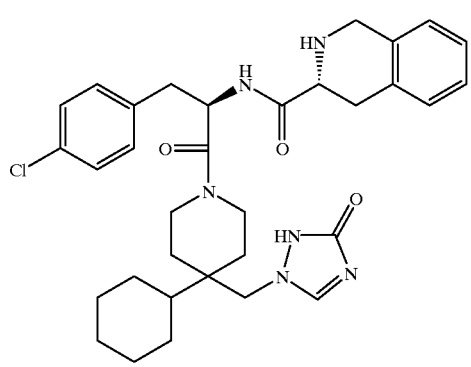
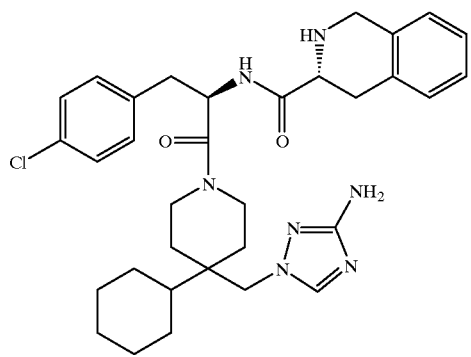
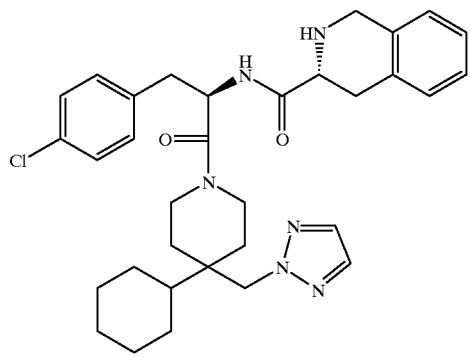
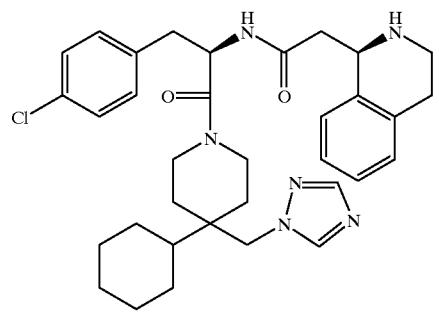
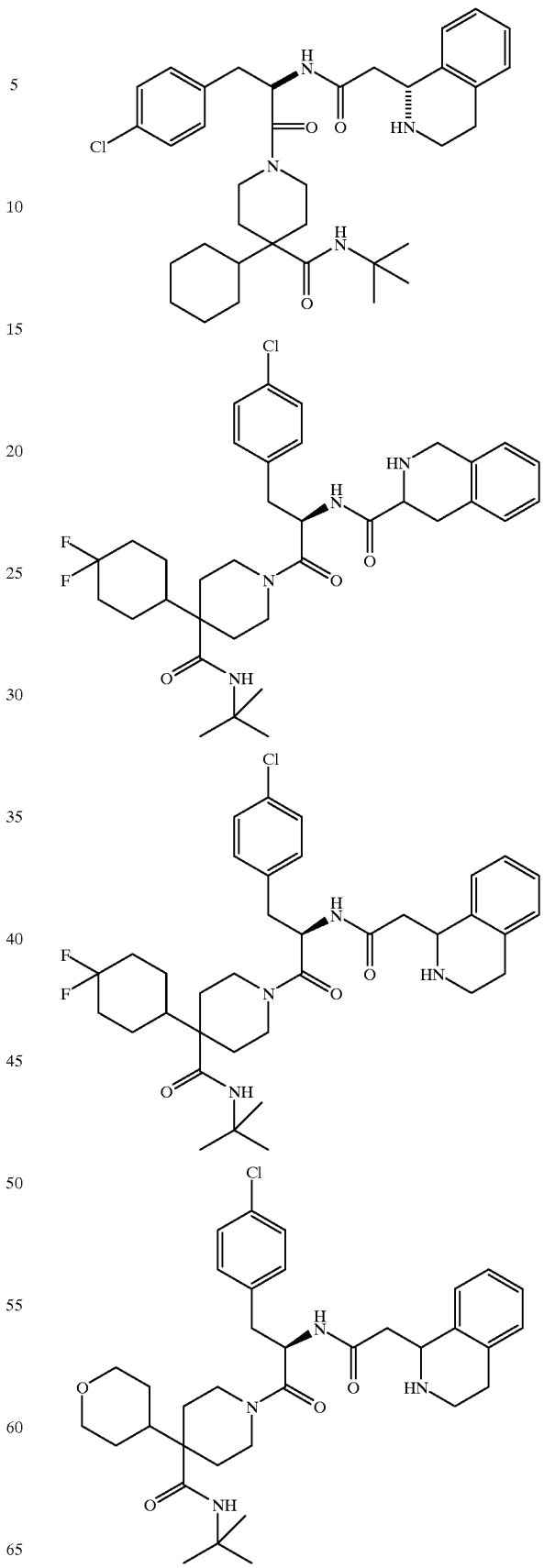

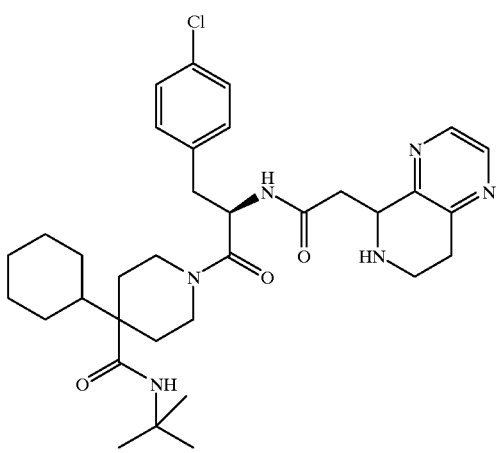

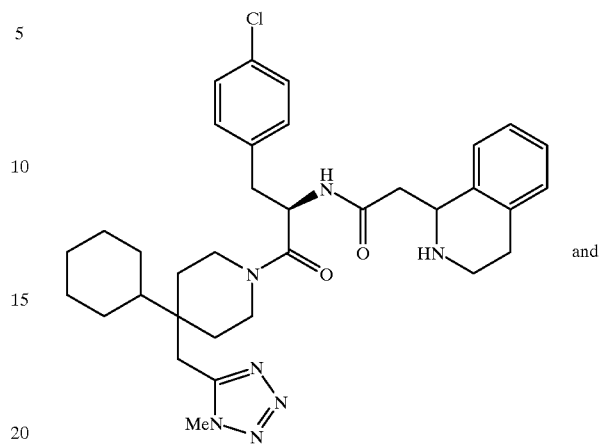 and

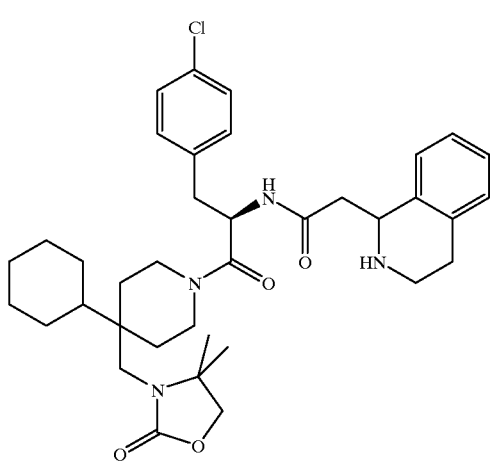

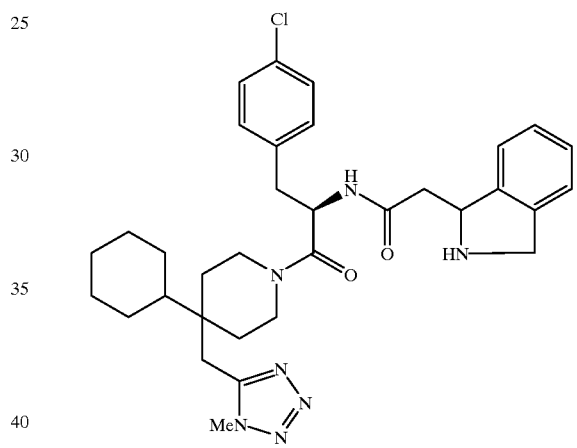

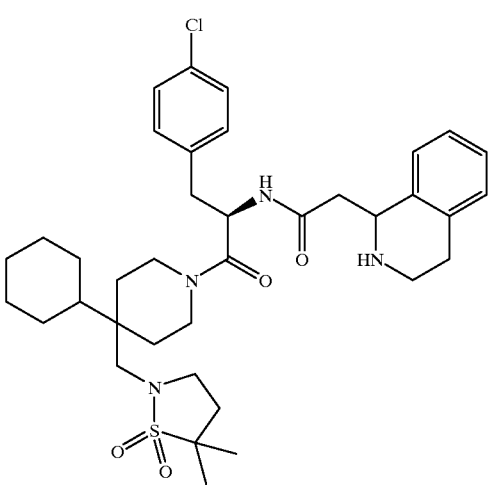

19. A method for the treatment or prevention of obesity which comprises administering to a subject in need of such treatment or prevention an effective amount of a compound of claim 1.

20. A method for the treatment or prevention of diabetes mellitus which comprises administering to a subject in need of such treatment or prevention an effective amount of a compound of claim 1.

21. A method for the treatment or prevention of male or female sexual dysfunction which comprises administering to a subject in need of such treatment or prevention an effective amount of a compound of claim 1.

22. A method for the treatment or prevention of erectile dysfunction which comprises administering to a subject in need of such treatment or prevention an effective amount of a compound of claim 1.

23. A method for the treatment or prevention of female sexual dysfunction which comprises administering to a subject in need of such treatment or prevention an effective amount of a compound of claim 1.

24. A pharmaceutical composition which comprises a compound of claim 1 and a pharmaceutically acceptable carrier.

25. The pharmaceutical composition of claim 24 further comprising a second active ingredient selected from the group consisting of an insulin sensitizer, an insulin mimetic, a sulfonylurea, an α-glucosidase inhibitor, an HMG-CoA reductase inhibitor, a sequestrant cholesterol lowering agent, a β3 adrenergic receptor agonist, a neuropeptide Y antagonist, a type V cyclic-GMP-selective phosphodiesterase inhibitor, an $\alpha_2$-adrenergic receptor antagonist, and a dopamine receptor agonist.

* * * * *